United States Patent [19]

Uchida et al.

[11] Patent Number: 4,540,703
[45] Date of Patent: Sep. 10, 1985

[54] TETRAZOLE DERIVATIVES, ANTI-ULCER COMPOSITION CONTAINING THE SAME AND METHOD FOR TREATING ULCERS

[75] Inventors: Minoru Uchida, Komatsujima; Takao Nishi; Kazuyuki Nakagawa, both of Tokushima, all of Japan

[73] Assignee: Otsuka Pharmaceutical Company, Limited, Japan

[21] Appl. No.: 333,806

[22] Filed: Dec. 23, 1981

Related U.S. Application Data

[63] Continuation-in-part of Ser. No. 124,710, Feb. 26, 1980, abandoned.

[30] Foreign Application Priority Data

Sep. 7, 1978 [JP] Japan ................. 53-110446

[51] Int. Cl.³ .............. A61K 31/41; C07D 257/04
[52] U.S. Cl. ..................... 514/381; 548/251; 548/200; 548/215; 548/240; 548/276; 548/253; 544/333; 544/63; 544/132; 546/238; 546/276; 546/210
[58] Field of Search ............... 548/251; 724/269; 514/381

[56] References Cited

U.S. PATENT DOCUMENTS 3,473,646  7/1973  Buckler ............... 260/293.69
4,372,953  2/1983  Uchida et al. ............ 548/251

FOREIGN PATENT DOCUMENTS 0029183  11/1979  European Pat. Off. ........ 548/251
047620   4/1980   Japan .

OTHER PUBLICATIONS

Jacobson, *J. Org. Chem.*, 18, 1183–1189, 1953.
Jacobson, *J. Org. Chem.*, 21, 311–315, 1956.
La Forge, *J. Org. Chem.*, 21, 767–771, 1956.

*Primary Examiner*—Richard L. Raymond
*Assistant Examiner*—D. B. Springer
*Attorney, Agent, or Firm*—Berman, Aisenberg & Platt

[57] ABSTRACT

Tetrazole derivatives of the formula:

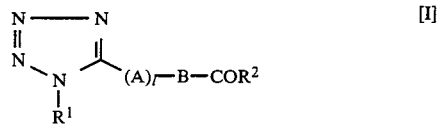

wherein $R^1$ is an optional defined substituent; A is sulfur or a lower alkylene-thio; l is 0 or 1; B is a lower alkylene; $R^2$ is hydroxy, a lower alkoxy, or a group:

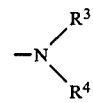

wherein $R^3$ and $R^4$ are optional defined substituents, or the $R^3$ and $R^4$ may combine together with the nitrogen atom to which they are joined to form a defined heterocyclic group, and a pharmaceutically acceptable salt thereof, which have prophylactic or therapeutic activities against peptic and/or duodenal ulcers and also anti-inflammatory activity and are useful as an anti-ulcer or anti-inflammatory drug; processes for the preparation of the tetrazole derivatives; and pharmaceutical composition containing said tetrazole derivatives.

52 Claims, No Drawings

TETRAZOLE DERIVATIVES, ANTI-ULCER COMPOSITION CONTAINING THE SAME AND METHOD FOR TREATING ULCERS

This application is a continuation-in-part application of U.S. Ser. No. 124,710 filed on Feb. 26, 1980, abandoned.

The present invention relates to novel tetrazole derivatives, a pharmaceutical composition for treating peptic and duodenal ulcers which contains as the essential ingredient the tetrazole derivatives, and a method for treating peptic and duodenal ulcers by administering the pharmaceutical composition.

The compounds of the present invention are tetrazole derivatives of the formula:

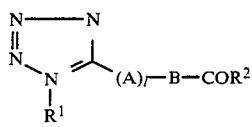

[I']

wherein $R^1$ is hydrogen, a lower alkyl, a cycloalkyl or phenyl; A is sulfur or a lower alkylene-thio; l is 0 or 1; B is a lower alkylene; $R^2$ is hydroxy, a lower alkoxy, or a group:

wherein $R^3$ and $R^4$ are the same or different and are each hydrogen, a lower alkyl, a cycloalkyl, phenyl, a cycloaklyl(lower)alkyl, a phenyl(lower)alkyl, a hydroxy(lower)alkyl, a saturated or unsaturated heterocyclic group containing one or two hetero atoms selected from the group consisting of nitrogen, oxygen and sulfur, or a lower alkyl substituted by said saturated or unsaturated heterocyclic group, or the $R^3$ and $R^4$ may combine together with the nitrogen atom to which they are joined with or without being intervened with oxygen or nitrogen to form a saturated or unsaturated heterocyclic group which may substituted with a lower alkyl or a lower alkanoyl; said cycloalkyl, phenyl and phenyl(lower)alkyl may have on the cycloalkyl or phenyl ring one or two substituents selected from the group consisting of a lower alkoxy, a lower alkyl, a halogen, an N,N-di(lower)alkylamino, nitro, aminosulfonyl, hydroxy and a lower alkanoyloxy, provided that when l is 0, B is $-CRR'-(CH_2)_p-$ (wherein R and R' are each hydrogen, methyl or ethyl, and p is 0 or 1) and $R^1$ is methyl, ethyl, n-butyl, cyclohexyl or an unsubstituted phenyl, $R^2$ is other than the groups selected from hydroxy and ethoxy, and when l is 0, B is $-CR''R'''-(CH_2)_q-$ (wherein R'' and R''' are each hydrogen or methyl, and q is 0 or 1) and $R^1$ is cyclohexyl, n-butyl or an unsubstituted phenyl, $R^2$ is other than the groups selected from a group: $-NR^{3'}R^{4'}$ (wherein one of $R^{3'}$ and $R^{4'}$ is hydrogen, methyl, ethyl or benzyl, and another one of them is hydrogen or ethyl and a heterocyclic group formed by combining $R^3$ and $R^4$ with nitrogen in $-NR^3R^4$ being morpholino, and a pharmaceutically acceptable salt thereof.

The present invention provides also a method for treating peptic and duodenal ulcers by administering a pharmaceutical composition which contains as an essential active ingredient a tetrazole derivative of the formula:

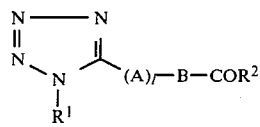

[I]

wherein $R^1$ is hydrogen, a lower alkyl, a cycloalkyl or phenyl; A is sulfur or a lower alkylene-thio; l is 0 or 1; B is a lower alkylene; $R^2$ is hydroxy, a lower alkoxy, or a group:

wherein $R^3$ and $R^4$ are the same or different and are each hydrogen, a lower alkyl, a cycloalkyl, phenyl, a cycloaklyl(lower)alkyl, a phenyl(lower)alkyl, a hydroxy(lower)alkyl, a saturated or unsaturated heterocyclic group containing one or two hetero atoms selected from the group consisting of nitrogen, oxygen and sulfur, or a lower alkyl substituted by said saturated or unsaturated heterocyclic group, or the $R^3$ and $R^4$ may combine together with the nitrogen atom to which they are joined with or without being intervened with oxygen or nitrogen to form a saturated or unsaturated heterocyclic group which may substituted with a lower alkyl or a lower alkanoyl; said cycloalkyl, phenyl and phenyl(lower)alkyl may have on the cycloalkyl or phenyl ring one or two substituents selected from the group consisting of a lower alkoxy, a lower alkyl, a halogen, an N,N-di(lower)alkylamino, nitro, aminosulfonyl, hydroxy and a lower alkanoyloxy, or a pharmaceutically acceptable salt thereof.

The compounds of the formulae [I] and [I'] of the present invention have prophylactic or therapeutic activities against peptic and/or duodenal ulcers, particularly stress ulcers, indomethacin-induced ulcers and acetic acid-induced ulcers, with less side effects, such as central nervous system activities, anti-cholinergic activity and the rate of gastric empting, and are useful as a medicine for treating such ulcers. The compounds also have anti-inflammatory activity and are useful as anti-inflammatory drugs.

In the present specification, the term "lower alkyl" denotes a straight or branched alkyl group having 1 to 6 carbon atoms and includes, for example, methyl, ethyl, propyl, isopropyl, butyl, tert-butyl, pentyl, and hexyl. The term "cycloalkyl" denotes a cycloalkyl group having 3 to 12 carbon atoms and includes, for example, cyclopropyl, cyclobutyl, cyclopentyl, cyclohexyl, cycloheptyl, cyclooctyl, cyclononyl, cyclodecanyl, cycloundecanyl, and cyclododecanyl. The term "lower alkylenethio" denotes a group formed by combining a straight or branched lower alkylene having 1 to 6 carbon atoms and a sulfur atom, wherein one terminal carbon atom of the lower alkylene is bonded to the carbon atom at 5-position of tetrazole ring and another terminal sulfur atom is bonded to the carbon atom at the terminal of the lower alkylene group "B" and includes, for example, methylenethio, ethylenethio, trimethylenethio, tetramethylenethio, pentamethylenethio, hexamethylenethio, 2-methyltrimethylenethio, 2,2-dimethyltrimethylenethio, and 1-methyltrimethylenethio. The term "lower alkylene" denotes a straight or branched alkylene having 1 to 6 carbon atoms and includes, for example, methylene, ethylene, trimethylene, tetramethylene, pentamethylene, hexamethylene, methylmethylene, 2-methyltrimethylene, 2,2-dimethyltrimethylene, and 1-methyltrimethylene.

The term "cycloalkyl(lower)alkyl" denotes a group formed by combining a straight or branched alkylene having 1 to 6 carbon atoms with a cycloalkyl having 3 to 8 carbon atoms and includes, for example, cyclopropylmethyl, cyclobutylmethyl, cyclopentylmethyl, cyclohexylmethyl, cycloheptylmethyl, cyclooctylmethyl, 2-cyclohexylethyl, 1-cyclohexylethyl, 3-cyclohexylpropyl, 1,1-dimethyl-2-cyclohexylethyl, 4-cyclohexylbutyl, 5-cyclohexylpentyl, and 6-cyclohexylhexyl. The term "phenyl(lower)alkyl" denotes a group formed by combining a straight or branched lower alkylene having 1 to 6 carbon atoms with a phenyl group and includes, for example, benzyl, 1-phenylethyl, 2-phenylethyl, 3-phenylpropyl, 4-phenylbutyl, 1,1-dimethyl-2-phenylethyl, 5-phenylpentyl, and 6-phenylhexyl. The term "hydroxy(lower)alkyl" denotes a group formed by combining a straight or branched lower alkyl having 1 to 6 carbon atoms with a hydroxy group and includes, for example, hydroxymethyl, 2-hydroxyethyl, 3-hydroxypropyl, 2-hydroxypropyl, 4-hydroxybutyl, 1,1-dimethyl-2-hydroxyethyl, 5-hydroxypentyl, and 6-hydroxyhexyl.

The term "heterocyclic group" denotes a 5- or 6-membered saturated or unsaturated heterocyclic group containing one or two hetero atoms selected from the group consisting of nitrogen, oxygen and sulfur and includes, for example, pyridyl, pyrrolyl, pyrrolidinyl, 3-pyrrolinyl, dihydropyridyl, piperidinyl, 2-pyrazolinyl, 2-imidazolinyl, imidazolyl, imidazolidinyl, pyrazolyl, pyrimidinyl, pyridazinyl, pyrazinyl, piperazinyl, oxazolyl, oxazolidinyl, isoxazolyl, 4H-1,4-oxazinyl, morpholinyl, thiazolyl, thiazolidinyl, isothiazolyl, 4H-1,4-thiazinyl, furyl, tetrahydrofuryl, 2H-pyranyl, 4H-pyranyl, 3,4-dihydro-2H-pyranyl, tetrahydropyranyl, thienyl, tetrahydrothienyl, thianyl, and 1,4-dithianyl.

The term "lower alkyl substituted by said saturated or unsaturated heterocyclic group" denotes a group formed by combining a straight or branched alkylene having 1 to 6 carbon atoms with a 5- or 6-membered saturated or unsaturated heterocyclic group containing one or two hetero atoms selected from the group consisting of nitrogen, oxygen and sulfur and includes, for example, 2-pyridylmethyl, 2-(3-pyridyl)ethyl, 4-(4-pyridyl)butyl, 2-thienylmethyl, 2-(3-thienyl)ethyl, 2-pyrimidinylmethyl, 2-tetrahydropyranylmethyl, 3-pyrrolylmethyl, 2-(2-pyrrolyl)ethyl, 3-pyrrolidinylmethyl, 2-(2-pyrrolidinyl)ethyl, 2-(3-pyrrolinyl)methyl, 4-piperidinylmethyl, 2-(2-piperidinyl)ethyl, 4-dihydropyridylmethyl, 3-piperidinylmethyl, piperidinomethyl, 2-pyrazinylmethyl, 3-pyrazolylmethyl, 2-(4-pyrazolyl)ethyl, 2-imidazolylmethyl, 4-(2-imidazolyl)butyl, 2-(4-imidazolyl)ethyl, 2-imidazolidinylmethyl, 3-(4-imidazolidinyl)propyl, 3-pyridazinylmethyl, 2-(4-pyridazinyl)ethyl, 2-pyrazinylmethyl, 4-(2-pyrazinyl)butyl, 2-(4-pyrimidinyl)ethyl, 6-(2-pyrimidinyl)hexyl, 2-pyrimidinylmethyl, 4-piperazinylmethyl, 3-(2-piperazinyl)propyl, piperazinomethyl, 2-oxazolylmethyl, 2-(4-oxazolyl)ethyl, 2-oxazolidinylmethyl, 4-isoxazolylmethyl, 2-(4H-1,4-oxazinyl)methyl, 3-morpholinylmethyl, morpholinomethyl, 2-thiazolylmethyl, 4-(4-thiazolyl)butyl, 2-thiazolidinylmethyl, 2-(4-thiazolidinyl)ethyl, 3-isothiazolylmethyl, 2-(4H-1,4-thiazinyl)methyl, furfuryl, 2-(3-furyl)-ethyl, 2-tetrahydrofurylmethyl, 2H-pyran-2-ylmethyl, 2H-pyran-4-ylmethyl, 4H-pyran-4-ylmethyl, 4H-pyran-3-ylmethyl, 2-(2-tetrahydropyranyl)ethyl, 2-(3-tetrahydropyranyl)ethyl, 4-(4-tetrahydropyranyl)butyl, 2-thienylmethyl, 2-(3-thienyl)ethyl, 2-(2-tetrahydrothienyl)ethyl, 3-thienylmethyl, 2-thianylmethyl, 2-(3-thianyl)ethyl, 4-thianylmethyl, and 1,4-dithian-2ylmethyl.

The "saturated or unsaturated heterocyclic group formed by combining the groups $R^3$ and $R^4$ together with the nitrogen atom to which they are joined with or without being intervened with oxygen or nitrogen" is a 5- or 6-membered saturated or unsaturated heterocyclic group and includes, for example, piperidino, pyrrolidino, piperazino, morpholino, 1-imidazolyl, 1-pyrazolyl, 4,5-dihydropyrazol-1-yl, 1-pyrrolyl, 4H-1,4-oxazin-4-yl, and 3-tetrahydrooxazolyl.

The term "lower alkoxy" donotes a straight or branched alkoxy group having 1 to 6 carbon atoms and includes, for example, methoxy, ethoxy, propoxy, isopropoxy, butoxy, tert-butoxy, pentyloxy, and hexyloxy. The term "halogen" includes fluorine, chlorine, bromine, and iodine. The term "N,N-di(lower)alkylamino" denotes an N,N-dialkylamino having 1 to 6 carbon atoms in each alkyl moiety and includes, for examle, N,N-dimethylamino, N,N-diethylamino, N-methyl-N-ethylamino, N,N-dipropylamino, N,N-diisopropylamino, N,N-dibutylamino, N-methyl-N-tert-butylamino, N,N-dipentylamino, and N,N-dihexylamino. The term "lower alkanoyloxy" denotes an alkanoyloxy group having 1 to 6 carbon atoms and includes, for example, acetyloxy, propionyloxy, butyryloxy, isobutyryloxy, pentanoyloxy, and hexanoyloxy. The term "lower alkanoyl" denotes an alkanoyl group having 1 to 6 carbon atoms and includes, for example, acetyl, propionyl, butyryl, isobutyryl, pentanoyl, and hexanoyl. The cycloalkyl, phenyl and phenyl(lower)alkyl having on the cycloalkyl or phenyl ring one or two substituents selected from the group consisting of a lower alkoxy, a lower alkyl, a halogen, an N,N-di(lower)alkylamino, nitro, aminosulfonyl, hydroxy or a lower alkanoyloxy include, for example, 2-hydroxycyclohexyl, 3-hydroxycyclohexyl, 4-hydroxycyclohexyl, 2,5-dihydroxycyclohexyl, 3,4-dihydroxycyclohexyl, 2-hydroxycyclopentyl, 4-hydroxycyclooctyl, 2-acetyloxycyclohexyl, 4-butyryloxycyclohexyl, 3,4-diacetyloxycyclohexyl, 2-methylcyclohexyl, 3-ethylcyclohexyl, 4-tert-butylcyclohexyl, 3,4-dimethylcyclohexyl, 2,5-dimethylcyclohexyl, 2-methoxycyclohexyl, 3-methoxycyclohexyl, 4-methoxycyclohexyl, 3,4-dimethoxycyclohexyl, 2,5-dimethoxycyclohexyl, 4-tert-butoxycyclohexyl, 3-methylcycloheptyl, 2-chlorocyclohexyl, 3-fluorocyclohexyl, 4-bromocyclohexyl, 3,4-difluorocyclohexyl, 2,5-dichlorocyclohexyl, 4-(N,N-dimethylamino)cyclohexyl, 3-(N,N-diethylamino)cyclohexyl, 2-nitrocyclohexyl, 3-nitrocyclooctyl, 4-nitrocyclohexyl, 3,5-dinitrocyclohexyl, 2-aminosulfonylcyclohexyl, 4-aminosulfonylcyclohexyl, 2-hydroxy-3-chlorocyclohexyl, 2-methyl-3-chlorocyclohexyl, 2-hydroxyphenyl, 3-hydroxyphenyl, 4-hydroxyphenyl, 2,5-dihydroxyphenyl, 3,4-dihydroxyphenyl, 2-acetyloxyphenyl, 4-isobutyryloxyphenyl, 3,4-diacetyloxyphenyl, 2-methylphenyl, 3-methylphenyl, 4-ethylphenyl, 3,4-dimethylphenyl, 2,5-diethylphenyl, 2-methoxyphenyl, 3-methoxyphenyl, 4-methoxyphenyl, 3,4-dimethoxyphenyl, 2,5-diethoxyphenyl, 4-isopropoxyphenyl, 2-chlorophenyl, 3-bromophenyl, 4-fluorophenyl, 2,5-dichlorophenyl, 3,4-dichlorophenyl, 4-(N,N-dimethylamino)phenyl, 2-(N,N-dimethylamino)phenyl, 3-(N,N-diethylamino)phenyl, 2-nitrophenyl, 3-nitrophenyl, 4-nitrophenyl, 2,4-dinitrophenyl, 2-aminosulfonylphenyl, 4-aminosulfonylphenyl, 2-hydroxy-3-chlorophenyl, 4-methoxy-2-chlorophenyl, 2-methyl-3-chlorophenyl, 2-hydroxybenzyl, 2-(4-hydroxyphenyl)ethyl, 4-(3-hydroxyphenyl)butyl, 2-(3,4-dihydroxyphenyl)ethyl, 1-(2,5-dihydroxyphenyl)ethyl, 2-acetyloxybenzyl, 2-(3-acetyloxyphenyl)ethyl, 2-(3,4-diacetyloxyphenyl)ethyl, 1,1-dimethyl-2-(3,4-diacetyloxyphenyl)ethyl, 2-methylbenzyl, 2-(4-methylphenyl)ethyl, 2-(3,4-dimethylphenyl)ethyl, 6-(2,5-dimethylphenyl)hexyl, 2-chlorobenzyl, 3-fluorobenzyl, 4-bromobenzyl, 2-(2-chlorophenyl)ethyl, 1-(4-chlorophenyl)ethyl, 2-(3,4-dichlorophenyl)ethyl, 5-(2,5-dichlorophenyl)pentyl, 4-(N,N-dimethylamino)benzyl, 2-[2-(N,N-dimethylamino)phenyl]ethyl, 2-nitrobenzyl, 2-(2,4-dinitrophenyl)ethyl, 1-(4-nitrophenyl)ethyl, 2-aminosulfonylbenzyl, 3-aminosulfonylbenzyl, 4-aminosulfonylbenzyl, 2-(4-aminosulfonylphenyl)ethyl, 2-hydroxy-3-chlorobenzyl, 4-methoxy-2-chlorobenzyl, 2-(2-methyl-3-chlorophenyl)ethyl, 2-methoxybenzyl, 4-methoxybenzyl, 2-(3,4-dimethoxyphenyl)ethyl, 1-(3,4-dimethoxyphenyl)ethyl, 2-(2,5-diethoxyphenyl)ethyl, 1,1-dimethyl-2-(3,4-dimethoxyphenyl)ethyl, and 6-(3,4-dimethoxyphenyl)hexyl.

Representative compounds of the present invention are as follows.

N-Ethyl-N-cyclohexyl-4-(1-methyl-1,2,3,4-tetrazol-5-yl)thio-butyramide

N-Butyl-N-cyclooctyl-4-(1-methyl-1,2,3,4-tetrazol-5-yl)thio-butyramide

N-Methyl-N-cyclopentyl-4-(1-methyl-1,2,3,4-tetrazol-5-yl)thio-butyramide

N-Isopropyl-N-cyclohexyl-4-(1-methyl-1,2,3,4-tetrazol-5-yl)thio-butyramide

N-Hexyl-N-cyclohexyl-4-(1-methyl-1,2,3,4-tetrazol-5-yl)thio-butyramide

N-Methyl-N-cyclododecanyl-4-(1-methyl-1,2,3,4-tetrazol-5-yl)thio-butyramide

N-Methyl-N-cyclohexyl-4-(1-ethyl-1,2,3,4-tetrazol-5-yl)thio-butyramide

N-Ethyl-N-cyclohexyl-4-(1-tert-butyl-1,2,3,4-tetrazol-5-yl)thio-butyramide

N-Methyl-N-cyclohexyl-4-(1-hexyl-1,2,3,4-tetrazol-5-yl)thio-butyramide

N-Cyclohexyl-4-(1-methyl-1,2,3,4-tetrazol-5-yl)thio-butyramide

N-Cyclododecanyl-4-(1-methyl-1,2,3,4-tetrazol-5-yl)thio-butyramide

N-Methyl-N-cyclohexyl-3-(1-methyl-1,2,3,4-tetrazol-5-yl)thio-propionamide

N-Methyl-N-cyclohexyl-2-(1-methyl-1,2,3,4-tetrazol-5-yl)thio-acetamide

N-Methyl-N-cyclohexyl-5-(1-methyl-1,2,3,4-tetrazol-5-yl)thio-valeramide

N-Methyl-N-cyclohexyl-7-(1-methyl-1,2,3,4-tetrazol-5-yl)thio-heptanamide

N-Methyl-N-cyclohexyl-4-(1-methyl-1,2,3,4-tetrazol-5-yl)thio-3-methylbutyramide

N-Ethyl-N-cyclohexyl-4-(1-ethyl-1,2,3,4-tetrazol-5-yl)thio-3,3-dimethylbutyramide N-Ethyl-N-cyclohexyl-4-(1-cyclohexyl-1,2,3,4-tetrazol-5-yl)thio-butyramide N-Ethyl-N-cyclohexyl-4-(1-cyclooctyl-1,2,3,4-tetrazol-5-yl)thio-butyramide N-Cyclohexyl-4-(1-cyclohexyl-1,2,3,4-tetrazol-5-yl)thio-butyramide N-Methyl-N-cyclohexyl-3-(1-cyclohexyl-1,2,3,4-tetrazol-5-yl)thio-propionamide N-Methyl-N-cyclohexyl-4-(1-cyclohexyl-1,2,3,4-tetrazol-5-yl)thio-3-methylbutyramide N-Methyl-N-cyclohexyl-4-(1-phenyl-1,2,3,4-tetrazol-5-yl)thio-butyramide N-Ethyl-N-cyclohexyl-3-(1-phenyl-1,2,3,4-tetrazol-5-yl)thio-propionamide N-Methyl-N-cyclohexyl-4-(1-phenyl-1,2,3,4-tetrazol-5-yl)thio-3-methylbutyramide N,N-Dicyclohexyl-4-(1-methyl-1,2,3,4-tetrazol-5-yl)thio-butyramide N-Cyclohexyl-N-cyclooctyl-4-(1-methyl-1,2,3,4-tetrazol-5-yl)thio-butyramide N,N-Dicyclohexyl-5-(1-phenyl-1,2,3,4-tetrazol-5-yl)thio-valeramide N,N-Dicyclohexyl-4-(1-cyclohexyl-1,2,3,4-tetrazol-5-yl)thio-butyramide N-Ethyl-N-cyclohexyl-4-[1-(4-hydroxycyclohexyl)-1,2,3,4-tetrazol-5-yl]thio-butyramide N-Methyl-N-cyclohexyl-4-[1-(3,4-dihydroxycyclohexyl)-1,2,3,4-tetrazol-5-yl]thio-butyramide N-Methyl-N-cyclohexyl-4-[1-(4-acetyloxycyclohexyl)-1,2,3,4-tetrazol-5-yl]thio-butyramide N-Methyl-N-cyclohexyl-4-[1-(4-methylcyclohexyl)-1,2,3,4-tetrazol-5-yl]thio-butyramide N-Methyl-N-cyclohexyl-4-[1-(2,5-dimethylcyclohexyl)-1,2,3,4-tetrazol-5-yl]thio-butyramide N-Methyl-N-cyclohexyl-4-[1-(2-methoxycyclohexyl)-1,2,3,4-tetrazol-5-yl]thio-butyramide N-Cyclohexyl-4-[1-(4-methoxycyclohexyl)-1,2,3,4-tetrazol-5-yl]thio-butyramide N-Methyl-N-cyclohexyl-4-[1-(3,4-dimethoxycyclohexyl)-1,2,3,4-tetrazol-5-yl]thio-butyramide N-Methyl-N-cyclohexyl-4-[1-(2-chlorocyclohexyl)-1,2,3,4-tetrazol-5-yl]thio-butyramide N-Ethyl-N-cyclohexyl-4-[1-(3-fluorocyclohexyl)-1,2,3,4-tetrazol-5-yl]thio-butyramide N-Ethyl-N-cyclohexyl-4-[1-(4-bromocyclohexyl)-1,2,3,4-tetrazol-5-yl]thio-butyramide N-Methyl-N-cyclohexyl-4-[1-(2,5-dichlorocyclohexyl)-1,2,3,4-tetrazol-5-yl]thio-butyramide N-Methyl-N-cyclohexyl-4-[1-(4-(N,N-dimethylamino)cyclohexyl)-1,2,3,4-tetrazol-5-yl]thio-butyramide N-Ethyl-N-cyclohexyl-4-[1-(2-nitrocyclohexyl)-1,2,3,4-tetrazol-5-yl]thio-butyramide N-Methyl-N-cyclohexyl-4-[1-(4-aminosulfonylcyclohexyl)-1,2,3,4-tetrazol-5-yl]thio-butyramide N-Ethyl-N-(2-hydroxycyclohexyl)-4-(1-methyl-1,2,3,4-tetrazol-5-yl)thio-butyramide N-Methyl-N-(3-hydroxycyclohexyl)-4-(1-methyl-1,2,3,4-tetrazol-5-yl)thio-butyramide N-Ethyl-N-(4-hydroxycyclohexyl)-4-(1-methyl-1,2,3,4-tetrazol-5-yl)thio-butyramide N-Methyl-N-(3,4-dihydroxycyclohexyl)-4-(1-methyl-1,2,3,4-tetrazol-5-yl)thio-butyramide N-Ethyl-N-(4-hydroxycyclohexyl)-4-(1-cyclohexyl-1,2,3,4-tetrazol-5-yl)thio-butyramide N-Methyl-N-(2-hydroxycyclohexyl)-4-(1-phenyl-1,2,3,4-tetrazol-5-yl)thio-butyramide N-Methyl-N-(4-hydroxycyclohexyl)-4-[1-(4-hydroxycyclohexyl)-1,2,3,4-tetrazol-5-yl]thio-butyramide N-(4-Hydroxycyclohexyl)-4-(1-methyl-1,2,3,4-tetrazol-5-yl)thio-butyramide N-(2-Hydroxycyclohexyl)-4-(1-cyclohexyl-1,2,3,4-tetrazol-5-yl)thio-butyramide N-(3-Hydroxycyclohexyl)-4-(1-phenyl-1,2,3,4-tetrazol-5-yl)thio-butyramide N-Methyl-N-(4-acetyloxycyclohexyl)-4-(1-ethyl-1,2,3,4-tetrazol-5-yl)thio-butyramide N-Ethyl-N-(3-acetyloxycyclohexyl)-4-(1-phenyl-1,2,3,4-tetrazol-5-yl)thio-butyramide N-Ethyl-N-(3-acetyloxycyclohexyl)-4-(1-cyclohexyl-1,2,3,4-tetrazol-5-yl)thio-butyramide N-Methyl-N-(3,4-diacetyloxycyclohexyl)-4-(1-methyl-1,2,3,4-tetrazol-5-yl)thio-butyramide N-(2-Acetyloxycyclohexyl)-4-(1-cyclohexyl-1,2,3,4-tetrazol-5-yl)thio-butyramide N,N-Di(4-hydroxycyclohexyl)-4-(1-methyl-1,2,3,4-tetrazol-5-yl)thio-butyramide N-Methyl-N-(2-methylcyclohexyl)-4-(1-methyl-1,2,3,4-tetrazol-5-yl)thio-butyramide N-Ethyl-N-(4-methylcyclohexyl)-4-(1-cyclohexyl-1,2,3,4-tetrazol-5-yl)thio-butyramide N-Methyl-N-(3-methylcyclohexyl)-4-(1-phenyl-1,2,3,4-tetrazol-5-yl)thio-butyramide N-Methyl-N-(3,4-dimethylcyclohexyl)-4-(1-methyl-1,2,3,4-tetrazol-5-yl)thio-butyramide N-Methyl-N-(4-methoxycyclohexyl)-4-(1-methyl-1,2,3,4-tetrazol-5-yl)thio-butyramide N-Ethyl-N-(2-methoxycyclohexyl)-4-(1-cyclohexyl-1,2,3,4-tetrazol-5-yl)thio-butyramide N-Methyl-N-(3-methoxycyclohexyl)-4-(1-phenyl-1,2,3,4-tetrazol-5-yl)thio-butyramide N-Methyl-N-(3,4-dimethoxycyclohexyl)-4-(1-methyl-1,2,3,4-tetrazol-5-yl)thio-butyramide N-(4-Methoxycyclohexyl)-4-(1-cyclohexyl-1,2,3,4-tetrazol-5-yl)thio-butyramide N-Methyl-N-(4-methoxycyclohexyl)-4-[1-(4-hydroxycyclohexyl)-1,2,3,4-tetrazol-5-yl]thio-butyramide N,N-Di(4-methoxycyclohexyl)-4-(1-methyl-1,2,3,4-tetrazol-5-yl)thio-butyramide N-Methyl-N-(2-chlorocyclohexyl)-4-(1-methyl-1,2,3,4-tetrazol-5-yl)thio-butyramide N-Methyl-N-(3-fluorocyclohexyl)-4-(1-cyclohexyl-1,2,3,4-tetrazol-5-yl)thio-butyramide N-Methyl-N-(4-bromocyclohexyl)-4-(1-phenyl-1,2,3,4-tetrazol-5-yl)thio-butyramide N-Methyl-N-(3,4-dichlorocyclohexyl)-4-(1-methyl-1,2,3,4-tetrazol-5-yl)thio-butyramide N-Methyl-N-[4-(N,N-dimethylamino)cyclohexyl]-4-(1-methyl-1,2,3,4-tetrazol-5-yl)thio-butyramide N-Methyl-N-(4-nitrocyclohexyl)-4-(1-methyl-1,2,3,4-tetrazol-5-yl)thio-butyramide N-Methyl-N-(4-aminosulfonylcyclohexyl)-4-(1-methyl-1,2,3,4-tetrazol-5-yl)thio-butyramide N-Methyl-N-(2-hydroxy-3-chlorocyclohexyl)-4-(1-methyl-1,2,3,4-tetrazol-5-yl)thio-butyramide N-Methyl-N-(2-hydroxyphenyl)-4-(1-methyl-1,2,3,4-tetrazol-5-yl)thio-butyramide N-(4-Hydroxyphenyl)-4-(1-methyl-1,2,3,4-tetrazol-5-yl)thio-butyramide N-Methyl-N-(2-acetyloxyphenyl)-4-(1-methyl-1,2,3,4-tetrazol-5-yl)thio-butyramide N-Ethyl-N-phenyl-4-(1-methyl-1,2,3,4-tetrazol-5-yl)thio-butyramide N-Methyl-N-phenyl-4-(1-phenyl-1,2,3,4-tetrazol-5-yl)thio-butyramide N-Methyl-N-phenyl-4-(1-cyclohexyl-1,2,3,4-tetrazol-5-yl)thio-butyramide N-Phenyl-4-(1-phenyl-1,2,3,4-tetrazol-5-yl)thio-butyramide N-Methyl-N-phenyl-5-(1-methyl-1,2,3,4-tetrazol-5-yl)thio-valeramide N-Methyl-N-(2-methylphenyl)-4-(1-methyl-1,2,3,4-tetrazol-5-yl)thio-butyramide N-(2-Methyl-3-chlorophenyl)-4-(1-methyl-1,2,3,4-tetrazol-5-yl)thio-butyramide N-Ethyl-N-(2-methylphenyl)-4-[1-(3,4-dihydroxyphenyl)-1,2,3,4-tetrazol-5-yl]thio-butyramide N-Methyl-N-(2,5-dimethylphenyl)-4-(1-methyl-1,2,3,4-tetrazol-5-yl)thio-butyramide N-Methyl-N-(2-methoxyphenyl)-4-(1-methyl-1,2,3,4-tetrazol-5-yl)thio-butyramide N-Methyl-N-(3-methoxyphenyl)-5-(1-phenyl-1,2,3,4-tetrazol-5-yl)thio-valeramide N-Methyl-N-(3,4-dimethoxyphenyl)-4-(1-methyl-1,2,3,4-tetrazol-5-yl)thio-butyramide N-Methyl-N-(3,4-dimethoxyphenyl)-4-[1-(4-hydroxycyclohexyl)-1,2,3,4-tetrazol-5-yl]thio-butyramide N-(2-Methoxyphenyl)-4-(1-methyl-1,2,3,4-tetrazol-5-yl)thio-butyramide N-(3,4-Dimethoxyphenyl)-4-(1-methyl-1,2,3,4-tetrazol-5-yl)thio-butyramide N-Methyl-N-(2-chlorophenyl)-4-(1-methyl-1,2,3,4-tetrazol-5-yl)thio-butyramide N-Methyl-N-(4-fluorophenyl)-4-(1-phenyl-1,2,3,4-tetrazol-5-yl)thio-butyramide N-(4-Chlorophenyl)-4-(1-methyl-1,2,3,4-tetrazol-5-yl)thio-butyramide N-[4-(N,N-Dimethylamino)phenyl]-4-(1-methyl-1,2,3,4-tetrazol-5-yl)thio-butyramide N-(4-Nitrophenyl)-4-(1-methyl-1,2,3,4-tetrazol-5-yl)thio-butyramide N-(4-Aminosufonylphenyl)-4-(1-methyl-1,2,3,4-tetrazol-5-yl)thio-butyramide N-Methyl-N-cyclohexyl-4-[1-(4-hydroxyphenyl)-1,2,3,4-tetrazol-5-yl]thio-butyramide N-Methyl-N-cyclohexyl-4-[1-(2-methoxyphenyl)-1,2,3,4-tetrazol-5-yl]thio-butyramide N-Ethyl-N-cyclohexyl-4-[1-(4-chlorophenyl)-1,2,3,4-tetrazol-5-yl]thio-butyramide N-Methyl-N-cyclohexyl-4-[1-(4-N,N-dimethylamino)phenyl-1,2,3,4-tetrazol-5-yl]thio-butyramide N-Methyl-N-cyclohexyl-4-[1-(4-aminosulfonylphenyl)-1,2,3,4-tetrazol-5-yl]thio-butyramide N-Methyl-N-cyclohexyl-4-[1-(4-nitrophenyl)-1,2,3,4-tetrazol-5-yl]thio-butyramide N,N-Dimethyl-4-(1-methyl-1,2,3,4-tetrazol-5-yl)thio-butyramide N,N-Diethyl-4-(1-methyl-1,2,3,4-tetrazol-5-yl)thio-butyramide N,N-Diisopropyl-4-(1-methyl-1,2,3,4-tetrazol-5-yl)thio-butyramide N,N-Dihexyl-4-(1-methyl-1,2,3,4-tetrazol-5-yl)thio-butyramide N-Methyl-N-ethyl-4-(1-methyl-1,2,3,4-tetrazol-5-yl)thio-butyramide N,N-Diethyl-5-(1-ethyl-1,2,3,4-tetrazol-5-yl)thio-valeramide N,N-Dimethyl-4-(1-methyl-1,2,3,4-tetrazol-5-yl)thio-3-methylbutyramide N,N-Diethyl-4-(1-cyclohexyl-1,2,3,4-tetrazol-5-yl)thio-butyramide N,N-Dimethyl-4-(1-phenyl-1,2,3,4-tetrazol-5-yl)thio-butyramide N,N-Diethyl-4-[1-(4-hydroxycyclohexyl)-1,2,3,4-tetrazol-5-yl]thio-butyramide N,N-Diethyl-3-[1-(2-hydroxyphenyl)-1,2,3,4-tetrazol-5-yl]thio-propionamide N,N-Diethyl-4-[1-(3,4-dimethoxyphenyl)-1,2,3,4-tetrazol-5-yl]thio-butyramide
N,N-Dimethyl-4-[1-(4-methylcyclohexyl)-1,2,3,4-tetrazol-5yl]thio-butyramide
N,N-Diethyl-4-[1-(2-chlorophenyl)-1,2,3,4-tetrazol-5-yl]thio-butyramide
N,N-Dimethyl-4-[1-(4-chlorocyclohexyl)-1,2,3,4-tetrazol-5-yl]thio-butyramide
N-tert-Butyl-4-(1-phenyl-1,2,3,4-tetrazol-5-yl)thio-butyramide
N-Ethyl-4-[1-(3,4-dimethoxyphenyl)-1,2,3,4-tetrazol-5-yl]thio-butyramide
4-(1-Methyl-1,2,3,4-tetrazol-5-yl)thio-butyramide
4-(1-Cyclohexyl-1,2,3,4-tetrazol-5-yl)thio-butyramide
N-Ethyl-N-cyclohexylmethyl-4-(1-methyl-1,2,3,4-tetrazol-5-yl)thio-butyramide
N-Ethyl-N-(2-cyclohexylethyl)-4-(1-cyclohexyl-1,2,3,4-tetrazol-5-yl)thio-butyramide
N-Methyl-N-cyclooctylmethyl-4-(1-phenyl-1,2,3,4-tetrazol-5-yl)thio-butyramide
N-Cyclohexylmethyl-4-(1-methyl-1,2,3,4-tetrazol-5-yl)thio-butyramide
N-Phenyl-N-cyclohexylmethyl-4-(1-methyl-1,2,3,4-tetrazol-5-yl)thio-butyramide
N,N-Dicyclohexylmethyl-4-(1-cyclohexyl-1,2,3,4-tetrazol-5-yl)thio-butyramide
N-Cyclohexyl-N-cyclohexylmethyl-4-(1-methyl-1,2,3,4-tetrazol-5-yl)thio-butyramide
N-Methyl-N-cyclohexylmethyl-4-[1-(4-hydroxycyclohexyl)-1,2,3,4-tetrazol-5-yl]thio-butyramide
N-Cyclohexylmethyl-N-(4-hydroxycyclohexyl)-4-(1-methyl-1,2,3,4-tetrazol-5-yl)thio-butyramide
N-Ethyl-N-benzyl-4-(1-methyl-1,2,3,4-tetrazol-5-yl)thio-butyramide
N,N-Dibenzyl-4-(1-methyl-1,2,3,4-tetrazol-5-yl)thio-butyramide
N-Methyl-N-benzyl-4-(1-cyclohexyl-1,2,3,4-tetrazol-5-yl)thio-butyramide
N-Ethyl-N-benzyl-4-(1-phenyl-1,2,3,4-tetrazol-5-yl)thio-butyramide
N-(1-Phenylethyl)-4-(1-methyl-1,2,3,4-tetrazol-5-yl)thio-butyramide
N-Cyclohexyl-N-benzyl-4-(1-methyl-1,2,3,4-tetrazol-5-yl)thio-butyramide
N-Phenyl-N-benzyl-4-(1-phenyl-1,2,3,4-tetrazol-5-yl)thio-butyramide
N-Methyl-N-benzyl-4-[1-(4-hydroxycyclohexyl)-1,2,3,4-tetrazol-5-yl]thio-butyramide
N-Ethyl-N-benzyl-4-[1-(3,4-dimethoxyphenyl)-1,2,3,4-tetrazol-5-yl]thio-butyramide
N-Ethyl-N-[2-(3,4-dimethoxyphenyl)ethyl]-4-(1-methyl-1,2,3,4-tetrazol-5-yl)thio-butyramide
N-Benzyl-N-[2-(3,4-dimethoxyphenyl)ethyl]-4-(1-methyl-1,2,3,4-tetrazol-5-yl)thio-butyramide
N-Methyl-N-[2-(4-methoxyphenyl)ethyl]-4-(1-methyl-1,2,3,4-tetrazol-5-yl)thio-butyramide
N-Methyl-N-[2-(3,4-dihydroxyphenyl)ethyl]-4-(1-methyl-1,2,3,4-tetrazol-5-yl)thio-butyramide
N-Cyclohexyl-N-(2-hydroxybenzyl)-4-(1-cyclohexyl-1,2,3,4-tetrazol-5-yl)thio-butyramide
N-Methyl-N-(2-acetyloxybenzyl)-4-(1-methyl-1,2,3,4-tetrazol-5-yl)thio-butyramide
N-Ethyl-N-[2-(3,4-diacetyloxyphenyl)ethyl]-4-(1-cyclohexyl-1,2,3,4-tetrazol-5-yl)thio-butyramide
N-Ethyl-N-(2-chlorobenzyl)-4-(1-methyl-1,2,3,4-tetrazol-5-yl)thio-butyramide
N-Cyclohexyl-N-[2-(3,4-dichlorophenyl)ethyl]-4-(1-methyl-1,2,3,4-tetrazol-5-yl)thio-butyramide
N-Methyl-N-(2-methylbenzyl)-5-(1-methyl-1,2,3,4-tetrazol-5-yl)thio-butyramide
N-Methyl-N-[2-(4-(N,N-dimethylamino)phenyl)ethyl]-4-(1-methyl-1,2,3,4-tetrazol-5-yl)thio-butyramide
N-Methyl-N-cyclohexyl-4-(1,2,3,4-tetrazol-5-yl)thio-butyramide
N,N-Dicyclohexyl-4-(1,2,3,4-tetrazol-5-yl)thio-butyramide
N-Methyl-N-phenyl-4-(1,2,3,4-tetrazol-5-yl)thio-butyramide
N-Methyl-N-cyclohexylmethyl-3-(1,2,3,4-tetrazol-5-yl)thio-propionamide
N,N-Dicyclohexylmethyl-4-(1,2,3,4-tetrazol-5-yl)thio-butyramide
N-Methyl-N-benzyl-4-(1,2,3,4-tetrazol-5-yl)thio-butyramide
4-(1,2,3,4-Tetrazol-5-yl)thio-butyramide
N-(2-Hydroxyethyl)-4-(1-methyl-1,2,3,4-tetrazol-5-yl)thio-butyramido
N-Cyclohexyl-N-(2-hydroxyethyl)-4-(1-methyl-1,2,3,4-tetrazol-5-yl)thio-butyramide
N-Methyl-N-(2-hydroxyethyl)-4-(1-methyl-1,2,3,4-tetrazol-5-yl)thio-butyramide
N-Cyclohexyl-N-(2-hydroxyethyl)-4-(1-cyclohexyl-1,2,3,4-tetrazol-5-yl)thio-butyramide
N-Ethyl-N-(2-hydroxyethyl)-4-(1-phenyl-1,2,3,4-tetrazol-5-yl)thio-butyramide
N-Phenyl-N-(2-hydroxyethyl)-4-(1-methyl-1,2,3,4-tetrazol-5-yl)thio-butyramide
N-Methyl-N-(4-hydroxybutyl)-4-(1-methyl-1,2,3,4-tetrazol-5-yl)thio-butyramide
N,N-Di(2-hydroxyethyl)-4-(1-methyl-1,2,3,4-tetrazol-5-yl)thio-butyramide
N-(2-Hydroxyethyl)-N-(4-hydroxycyclohexyl)-4-(1-methyl-1,2,3,4-tetrazol-5-yl)thio-butyramide
N-(2-Hydroxyethyl)-N-benzyl-4-(1-methyl-1,2,3,4-tetrazol-5-yl)thio-butyramide
N-(2-Hydroxyethyl)-N-cyclohexylmethyl-4-(1-cyclohexyl-1,2,3,4-tetrazol-5-yl)thio-butyramide
N-(2-Hydroxyethyl)-N-[2-(3,4-dimethoxyphenyl)ethyl]-4-(1-methyl-1,2,3,4-tetrazol-5-yl)thio-butyramide
5-(3-Morpholinocarbonylpropylthio)-1-methyl-1,2,3,4-tetrazole
5-(3-Piperidinocarbonylpropylthio)-1-methyl-1,2,3,4-tetrazole
5-(4-Pyrrolidinocarbonylbutylthio)-1-methyl-1,2,3,4-tetrazole
5-(3-Piperazinocarbonylpropylthio)-1-cyclohexyl-1,2,3,4-tetrazole
5-[3-(1-Imidazolyl)carbonylpropylthio]-1-methyl-1,2,3,4-tetrazole
5-[3-(1-Pyrazolyl)carbonylpropylthio]-1-methyl-1,2,3,4-tetrazole
5-[3-(1-pyrrolyl)carbonylpropylthio]-1-methyl-1,2,3,4-tetrazole
5-[3-(4-methylpiperazino)carbonylpropylthio]-1-methyl-1,2,3,4-tetrazole
5-[4-(1-Imedazolyl)carbonylbutylthio]-1-cyclohexyl-1,2,3,4-tetrazole
5-[3-(1-Pyrazolyl)carbonylpropylthio]-1-phenyl-1,2,3,4-tetrazole
5-[3-(4-Acetylpiperazino)carbonylpropylthio]-1-methyl-1,2,3,4-tetrazole
N-(2-Pyridyl)-4-(1-methyl-1,2,3,4-tetrazol-5-yl)thio-butyramide N-Ethyl-N-(2-pyridyl)-4-(1-methyl-1,2,3,4-tetrazol-5-yl)thio-butyramide
N-Cyclohexyl-N-(4-pyridyl)-4-(1-methyl-1,2,3,4-tetrazol-5-yl)thio-butyramide
N-Methyl-N-(3-pyridyl)-4-(1-cyclohexyl-1,2,3,4-tetrazol-5-yl)thio-butyramide
N-Methyl-N-(2-pyridylmethyl)-4-(1-methyl-1,2,3,4-tetrazol-5-yl)thio-butyramide
N-Methyl-N-(2-pyrrolyl)-4-(1-methyl-1,2,3,4-tetrazol-5-yl)thio-butyramide
N-Methyl-N-(3-pyrrolidinylmethyl)-4-(1-phenyl-1,2,3,4-tetrazol-5-yl)thio-butyramide
N-(3-Pyrrolin-2-yl)-4-(1-methyl-1,2,3,4-tetrazol-5-yl)thio-butyramide
N-Methyl-N-(3-pyrrolin-2-ylmethyl)-4-(1-cyclohexyl-1,2,3,4-tetrazol-5-yl)thio-butyramide
N-Methyl-N-(2-piperidinyl)-4-(1-methyl-1,2,3,4-tetrazol-5-yl)thio-butyramide
N-Cyclohexyl-N-(4-piperidinylmethyl)-4-(1-cyclohexyl-1,2,3,4-tetrazol-5-yl)thio-butyramide
N-Methyl-N-(2-pyrazolin-4-yl)-4-(1-methyl-1,2,3,4-tetrazol-5-yl)thio-butyramide
N-Methyl-N-(2-imidazolyl)-4-(1-methyl-1,2,3,4-tetrazol-5-yl)thio-butyramide
N-Cyclohexyl-N-(2-imidazolylmethyl)-4-(1-methyl-1,2,3,4-tetrazol-5-yl)thio-butyramide
N-(2-Imidazolidinyl)-5-(1-methyl-1,2,3,4-tetrazol-5-yl)thio-valeramide
N-Cyclohexyl-N-(3-pyrazolylmethyl)-4-(1-methyl-1,2,3,4-tetrazol-5-yl)thio-butyramide
N-(2-Pyrimidinyl)-4-(1-methyl-1,2,3,4-tetrazol-5-yl)thio-butyramide
N-Cyclohexyl-N-(3-pyridazinylmethyl)-4-(1-cyclohexyl-1,2,3,4-tetrazol-5-yl)thio-butyramide
N-(2-Pyrazinyl)-4-(1-cyclohexyl-1,2,3,4-tetrazol-5-yl)thio-butyramide
N-Methyl-N-(2-pyradinylmethyl)-4-(1-methyl-1,2,3,4-tetrazol-5-yl)thio-butyramide
N-Cyclohexyl-N-(2-oxazolyl)-4-(1-cyclohexyl-1,2,3,4-tetrazol-5-yl)thio-butyramide
N-Methyl-N-(2-oxazolylmethyl)-4-(1-methyl-1,2,3,4-tetrazol-5-yl)thio-butyramide
N-Methyl-N-(4-isoxazolyl)-4-(1-methyl-1,2,3,4-tetrazol-5-yl)thio-butyramide
N-(2-Thiazolyl)-4-(1-methyl-1,2,3,4-tetrazol-5-yl)thio-butyramide
N-Methyl-N-(2-furyl)-4-(1-cyclohexyl-1,2,3,4-tetrazol-5-yl)thio-butyramide
N-Furfuryl-4-(1-methyl-1,2,3,4-tetrazol-5-yl)thio-butyramide
N-Methyl-N-(2-tetrahydrofuryl)-4-(1-methyl-1,2,3,4-tetrazol-5-yl)thio-butyramide
N-Methyl-N-(2H-pyran-2-yl)-4-(1-methyl-1,2,3,4-tetrazol-5-yl)thio-butyramide
N-Methyl-N-(2-tetrahydropyranylmethyl)-4-(1-methyl-1,2,3,4-tetrazol-5-yl)thio-butyramide
N-(2-Thienyl)-4-(1-phenyl-1,2,3,4-tetrazol-5-yl)thio-butyramide
N-Methyl-N-(2-thienylmethyl)-4-(1-methyl-1,2,3,4-tetrazol-5-yl)thio-butyramide
N-Methyl-N-(4-thianyl)-4-(1-methyl-1,2,3,4-tetrazol-5-yl)thio-butyramide
N-Ethyl-N-cyclohexyl-5-(1-methyl-1,2,3,4-tetrazol-5-yl)valeramide
N-Butyl-N-cyclooctyl-5-(1-methyl-1,2,3,4-tetrazol-5-yl)valeramide
N-Ethyl-N-cyclohexyl-4-(1-tert-butyl-1,2,3,4-tetrazol-5-yl)butyramide
N-Methyl-N-cyclohexyl-7-(1-methyl-1,2,3,4-tetrazol-5-yl)heptanamide
N-Methyl-N-cyclohexyl-4-(1-methyl-1,2,3,4-tetrazol-5-yl)-3-methylbutyramide
N-Methyl-N-cyclohexyl-4-(1-cyclotridecanyl-1,2,3,4-tetrazol-5-yl)butyramide
N-Ethyl-N-cyclohexyl-5-(1-cyclohexyl-1,2,3,4-tetrazol-5-yl)valeramide
N-Ethyl-N-cyclohexyl-5-(1-phenyl-1,2,3,4-tetrazol-5-yl)valeramide
N,N-Dicyclohexyl-5-(1-phenyl-1,2,3,4-tetrazol-5-yl)valeramide
N,N-Dicyclohexyl-4-(1-cyclohexyl-1,2,3,4-tetrazol-5-yl)butyramide
N-Ethyl-N-cyclohexyl-4-[1-(4-hydroxycyclohexyl)-1,2,3,4-tetrazol-5-yl]butyramide
N-Methyl-N-cyclohexyl-5-[1-(4-acetyloxycyclohexyl)-1,2,3,4-tetrazol-5-yl]valeramide
N-Methyl-N-cyclohexyl-5-[1-(4-methylcyclohexyl)-1,2,3,4-tetrazol-5-yl]valeramide
N-Methyl-N-cyclohexyl-5-[1-(3,4-dimethoxycyclohexyl)-1,2,3,4-tetrazol-5-yl]valeramide
N-Methyl-N-cyclohexyl-4-[1-(2-chlorocyclohexyl)-1,2,3,4-tetrazol-5-yl]butyramide
N-Methyl-N-cyclohexyl-5-[1-(4-(N,N-dimethylamino)cyclohexyl)-1,2,3,4-tetrazol-5-yl]valeramide
N-Ethyl-N-(4-hydroxycyclohexyl)-4-(1-cyclohexyl-1,2,3,4-tetrazol-5-yl)butyramide
N-Methyl-N-(2-hydroxycyclohexyl)-4-(1-phenyl-1,2,3,4-tetrazol-5-yl)butyramide
N-(4-Hydroxycyclohexyl)-5-(1-phenyl-1,2,3,4-tetrazol-5-yl)valeramide
N-Methyl-N-(4-acetyloxycyclohexyl)-4-(1-ethyl-1,2,3,4-tetrazol-5-yl)butyramide
N-Ethyl-N-(2-acetyloxycyclohexyl)-5-(1-phenyl-1,2,3,4-tetrazol-5-yl)valeramide
N-Ethyl-N-(3-acetyloxycyclohexyl)-4-(1-cyclohexyl-1,2,3,4-tetrazol-5-yl)butyramide
N-Ethyl-N-(4-methylcyclohexyl)-4-(1-cyclohexyl-1,2,3,4-tetrazol-5-yl)butyramide
N-Methyl-N-(3,4-dimethylcyclohexyl)-5-(1-phenyl-1,2,3,4-tetrazol-5-yl)valeramide
N-Ethyl-N-(2-methoxycyclohexyl)-5-(1-cyclohexyl-1,2,3,4-tetrazol-5-yl)valeramide
N-Methyl-N-(3,4-dimethoxycyclohexyl)-5-(1-pheny-1,2,3,4-tetrazol-5-yl)valeramide
N,N-Di(4-hydroxycyclohexyl)-4-[1-(4-hydroxycyclohexyl)-1,2,3,4-tetrazol-5-yl]butyramide
N-Methyl-N-(2-chlorocyclohexyl)-5-(1-methyl-1,2,3,4-tetrazol-5-yl)valeramide
N-Methyl-N-[4-(N,N-dimethylamino)cyclohexyl]-4-(1-phenyl-1,2,3,4-tetrazol-5-yl)butyramide
N-Methyl-N-(4-nitrocyclohexyl)-4-(1-methyl-1,2,3,4-tetrazol-5-yl)butyramide
N-Methyl-N-(4-aminosulfonylcyclohexyl)-5-(1-cyclohexyl-1,2,3,4-tetrazol-5-yl)valeramide
N-Methyl-N-(4-hydroxyphenyl)-5-(1-phenyl-1,2,3,4-tetrazol-5-yl)valeramide
N-Ethyl-N-phenyl-4-(1-methyl-1,2,3,4-tetrazol-5-yl)butyramide
N-Methyl-N-phenyl-5-(1-phenyl-1,2,3,4-tetrazol-5-yl)valeramide
N,N-Diphenyl-5-(1-phenyl-1,2,3,4-tetrazol-5-yl)valeramide
N-Phenyl-4-(1-phenyl-1,2,3,4-tetrazol-5-yl)butyramide
N-Methyl-N-(4-methylphenyl)-5-(1-phenyl-1,2,3,4-tetrazol-5-yl)valeramide N-Methyl-N-(2,5-dimethylphenyl)-4-(1-phenyl-1,2,3,4-tetrazol-5-yl)butyramide
N-Methyl-N-(3,4-dimethoxyphenyl)-4-(1-phenyl-1,2,3,4-tetrazol-5-yl)butyramide
N-Methyl-N-(4-methoxyphenyl)-4-[1-(4-methoxyphenyl)-1,2,3,4-tetrazol-5-yl]butyramide
N-Methyl-N-(3,4-dichlorophenyl)-4-(1-cyclohexyl-1,2,3,4-tetrazol-5-yl)butyramide
N-Methyl-N-cyclohexyl-4-[1-(2-methoxyphenyl)-1,2,3,4-tetrazol-5-yl]butyramide
N-Ethyl-N-cyclohexyl-4-[1-(4-chlorophenyl)-1,2,3,4-tetrazol-5-yl]butyramide
N-Methyl-N-phenyl-5-[1-(4-methylphenyl)-1,2,3,4-tetrazol-5-yl]valeramide
N-Methyl-N-cyclohexyl-4-[1-(4-(N,N-dimethylamino)phenyl)-1,2,3,4-tetrazol-5-yl]butyramide
N-Methyl-N-cyclohexyl-4-[1-(4-aminosulfonylphenyl)-1,2,3,4-tetrazol-5-yl]butyramide
N,N-Diethyl-5-(1-ethyl-1,2,3,4-tetrazol-5-yl)valeramide
N-Methyl-N-tert-butyl-4-(1-methyl-1,2,3,4-tetrazol-5-yl)butyramide
N,N-Diethyl-5-(1-cyclohexyl-1,2,3,4-tetrazol-5-yl)valeramide
N,N-Diethyl-5-(1-phenyl-1,2,3,4-tetrazol-5-yl)valeramide
N,N-Diethyl-4-[1-(4-hydroxycyclohexyl)-1,2,3,4-tetrazol-5-yl]butyramide
N,N-Diethyl-5-[1-(3,4-dimethloxyphenyl)-1,2,3,4-tetrazol-5-yl]valeramide
N-tert-Butyl-4-(1-phenyl-1,2,3,4-tetrazol-5-yl)butyramide
5-(1-Phenyl-1,2,3,4-tetrazol-5-yl)valeramide
N-Ethyl-N-cyclohexylmethyl-5-(1-methyl-1,2,3,4-tetrazol-5-yl)valeramide
N,N-Dicyclohexylmethyl-5-(1-cyclohexyl-1,2,3,4-tetrazol-5-yl)valeramide
N-Cyclohexyl-N-cyclohexylmethyl-4-(1-cyclohexyl-1,2,3,4-tetrazol-5-yl)butyramide
N-Cyclohexylmethyl-N-(2-cyclohexylethyl)-4-(1-cyclohexyl-1,2,3,4-tetrazol-5-yl)butyramide
N-Ethyl-N-benzyl-4-(1-phenyl-1,2,3,4-tetrazol-5-yl)butyramide
N-Cyclohexyl-N-benzyl-5-(1-cyclohexyl-1,2,3,4-tetrazol-5-yl)valeramide
N-Ethyl-N-[2-(3,4-dimethoxyphenyl)ethyl]-4-(1-cyclohexyl-1,2,3,4-tetrazol-5-yl)butyramide
N-Benzyl-N-[2-(3,4-dimethoxyphenyl)ethyl]-4-(1-phenyl-1,2,3,4-tetrazol-5-yl)butyramide
N-Phenyl-N-[2-(3,4-dimethoxyphenyl)ethyl]-4-(1-phenyl-1,2,3,4-tetrazol-5-yl)butyramide
N-Ethyl-N-[2-(3,4-diacetyloxyphenyl)ethyl]-4-(1-cyclohexyl-1,2,3,4-tetrazol-5-yl)butyramide
N-Cyclohexyl-N-[2-(3,4-dichlorophenyl)ethyl]-4-(1-cyclohexyl-1,2,3,4-tetrazol-5-yl)butyramide
N-Ethyl-N-[1-(4-nitrophenyl)ethyl]-4-(1-methyl-1,2,3,4-tetrazol-5-yl)butyramide
N-Methyl-N-cyclohexyl-5-(1,2,3,4-tetrazol-5-yl)valeramide
N-Phenyl-N-cyclohexyl-4-(1,2,3,4-tetrazol-5-yl)butyramide
5-(1,2,3,4-Tetrazol-5-yl)valeramide
N-Cyclohexyl-N-(2-hydroxyethyl)-4-(1-cyclohexyl-1,2,3,4-tetrazol-5-yl)butyramide
N-Methyl-N-(2-hydroxyethyl)-5-(1-phenyl-1,2,3,4-tetrazol-5-yl)valeramide
5-(4-Piperidinocarbonybutyl)-1-phenyl-1,2,3,4-tetrazole
5-(4-Piperidinocarbonylbutyl)-1-methyl-1,2,3,4-tetrazole
5-[3-(1-Imidazolyl)carbonylpropyl]-1-cyclohexyl-1,2,3,4-tetrazole
5-[4-(4-Methylpiperazino)carbonylbutyl]-1-phenyl-1,2,3,4-tetrazole
5-[3-(4-Acetylpiperazino)carbonylpropyl]-1-methyl-tetrazole
N-(2-Pyridyl)-5-(1-methyl-1,2,3,4-tetrazol-5-yl)valeramide
N-Ethyl-N-(2-pyridyl)-4-(1-phenyl-1,2,3,4-tetrazol-5-yl)butyramide
N-Methyl-N-(2-pyridylmethyl)-4-(1-cyclohexyl-1,2,3,4-tetrazol-5-yl)butyramide
N-Methyl-N-[2-(3-pyrrolinyl)methyl]-4-(1-cyclohexyl-1,2,3,4-tetrazol-5-yl)butyramide
N-Cyclohexyl-N-(4-piperidinylmethyl)-5-(1-cyclohexyl-1,2,3,4-tetrazol-5-yl)-valeramide
N-Methyl-N-(2-imidazolyl)-5-(1-cyclohexyl-1,2,3,4-tetrazol-5-yl)valeramide
N-Cyclohexyl-N-(3-pyrazolylmethyl)-4-(1-methyl-1,2,3,4-tetrazol-5-yl)butyramide
N-(2-Pyrimidinyl)-4-(1-cyclohexyl-1,2,3,4-tetrazol-5-yl)thio-butyramide
N-Cyclohexyl-N-(3-pyridazinylmethyl)-4-(1-cyclohexyl-1,2,3,4-tetrazol-5-yl)butyramide
N-Methyl-N-(2-oxazolylmethyl)-4-(1-phenyl-1,2,3,4-tetrazol-5-yl)butyramide
N-Cyclohexyl-N-(morpholinomethyl)-4-(1-cyclohexyl-1,2,3,4-tetrazol-5-yl)butyramide
N-(2-Thiazolyl)-4-(1-methyl-1,2,3,4-tetrazol-5-yl)butyramide
N-Methyl-N-(2-furyl)-5-(1-cyclohexyl-1,2,3,4-tetrazol-5-yl)valeramide
N-Methyl-N-(2-tetrahydrofurylmethyl)-4-(1-cyclohexyl-1,2,3,4-tetrazol-5-yl)butyramide
N-(2-Thienyl)-4-(1-phenyl-1,2,3,4-tetrazol-5-yl)butyramide
N-Ethyl-N-[1-(4-nitrophenyl)ethyl]-4-(1-methyl-1,2,3,4-tetrazol-5-yl)thio-butyramide
N-Methyl-N-[2-(4-aminosulfonylphenyl)ethyl]-4-(1-methyl-1,2,3,4-tetrazol-5-yl)thio-butyramide
N-Ethyl-N-cyclohexyl-4-[1-(2-nitrocyclohexyl)-1,2,3,4-tetrazol-5-yl]butyramide
N-Methyl-N-cyclohexyl-4-[1-(4-aminosulfonylcyclohexyl)-1,2,3,4-tetrazol-5-yl]butyramide
N-Phenyl-N-[2-(3,4-dimethylphenyl)ethyl]-4-(1-phenyl-1,2,3,4-tetrazol-5-yl)butyramide
N-Methyl-N-[2-(4-(N,N-dimethylamino)phenyl)ethyl]-4-(1-cyclohexyl-1,2,3,4-tetrazol-5-yl)butyramide
N-Methyl-N-[2-(4-aminosulfonylphenyl)ethyl]-4-(1-phenyl-1,2,3,4-tetrazol-5-yl)butyramide
N,N-Diethyl-3-(1-methyl-1,2,3,4-tetrazol-5-yl)methylthio-propionamide
N,N-Diethyl-3-(1-phenyl-1,2,3,4-tetrazol-5-yl)methylthio-propionamide
N,N-Diethyl-3-(1-cyclohexyl-1,2,3,4-tetrazol-5-yl)methylthio-propionamide
N,N-Diethyl-3-[2-(1-methyl-1,2,3,4-tetrazol-5-yl)ethylthio]propionamide
N-Ethyl-N-cyclohexyl-3-(1-methyl-1,2,3,4-tetrazol-5-yl)methylthio-propionamide
N-Ethyl-N-cyclohexyl-3-(1-phenyl-1,2,3,4-tetrazol-5-yl)methylthio-propionamide
N-Ethyl-N-cyclohexyl-3-(1-cyclohexyl-1,2,3,4-tetrazol-5-yl)methylthio-propionamide
N-Ethyl-N-cyclohexyl-3-[2-methyl-3-(1-methyl-1,2,3,4-tetrazol-5-yl)propylthio]propionamide N,N-dicyclohexyl-3-(1-cyclohexyl-1,2,3,4-tetrazol-5-yl)methylthio-propionamide
N-Ethyl-N-phenyl-3-(1-methyl-1,2,3,4-tetrazol-5-yl)methylthio-propionamide
N-Ethyl-N-phenyl-3-(1-cyclohexyl-1,2,3,4-tetrazol-5-yl)methylthio-propionamide
N-Ethyl-N-phenyl-3-(1-phenyl-1,2,3,4-tetrazol-5-yl)methylthio-propionamide
N,N-Diphenyl-3-(1-phenyl-1,2,3,4-tetrazol-5-yl)methylthio-propionamide
N-Ethyl-N-cyclohexyl-4-(1-methyl-1,2,3,4-tetrazol-5-yl)methylthio-butyramide
N-Ethyl-N-benzyl-3-(1-methyl-1,2,3,4-tetrazol-5-yl)methylthio-propionamide
N-Ethyl-N-cyclohexylmethyl-3-(1-methyl-1,2,3,4-tetrazol-5-yl)methylthio-propionamide
N-Ethyl-N-(4-hydroxycyclohexyl)-3-(1-methyl-1,2,3,4-tetrazol-5-yl)methylthio-propionamide
N-Ethyl-N-[2-(3,4-dimethoxyphenyl)ethyl]-3-(1-methyl-1,2,3,4-tetrazol-5-yl)methylthio-propionamide
N-Ethyl-N-(4-methylphenyl)-3-(1-methyl-1,2,3,4-tetrazol-5-yl)methylthio-propionamide
N-Ethyl-N-cyclohexyl-3-(1-ethyl-1,2,3,4-tetrazol-5-yl)methylthio-propionamide
N,N-Diethyl-3-[1-(4-ethylphenyl)-1,2,3,4-tetrazol-5-yl]methylthio-propionamide
N-Ethyl-N-cyclohexyl-3-[1-(4-hydroxycyclohexyl)-1,2,3,4-tetrazol-5-yl]methylthio-propionamide
N-Ethyl-N-cyclohexyl-3-[1-(3,4-dimethoxyphenyl)-1,2,3,4-tetrazol-5-yl]methylthio-propionamide
N-Ethyl-N-cyclohexyl-3-(1,2,3,4-tetrazol-5-yl)methylthio-propionamide
3-(1-Methyl-1,2,3,4-tetrazol-5-yl)methylthio-propionamide
N-Ethyl-N-(2-hydroxyethyl)-3-(1-methyl-1,2,3,4-tetrazol-5-yl)methylthio-propionamide
N-Ethyl-N-(2-pyridyl)-3-(1-methyl-1,2,3,4-tetrazol-5-yl)methylthio-propionamide
N-Ethyl-N-(2-pyridylmethyl)-3-(1-methyl-1,2,3,4-tetrazol-5-yl)methylthio-propionamide
N-Ethyl-3-(1-methyl-1,2,3,4-tetrazol-5-yl)methylthio-propionamide
N-Cyclohexyl-3-(1-methyl-1,2,3,4-tetrazol-5-yl)methylthio-propionamide
N-Phenyl-3-(1-methyl-1,2,3,4-tetrazol-5-yl)methylthio-propionamide
N-Furyl-3-(1-methyl-1,2,3,4-tetrazol-5-yl)methylthio-propionamide
N-Ethyl-N-(2-thienylmethyl)-3-(1-methyl-1,2,3,4-tetrazol-5-yl)methylthio-propionamide
5-[(2-Piperidinocarbonylethyl)thiomethyl]-1-methyl-1,2,3,4-tetrazole
5-[(2-Morpholinocarbonylethyl)thiomethyl]-1-methyl-1,2,3,4-tetrazole
Methyl 4-(1-methyl-1,2,3,4-tetrazol-5-yl)thio-butyrate
Methyl 4-(1-isopropyl-1,2,3,4-tetrazol-5-yl)thio-butyrate
Methyl 4-(1-phenyl-1,2,3,4-tetrazol-5-yl)thio-butyrate
Ethyl 4-(1-cyclohexyl-1,2,3,4-tetrazol-5-yl)thio-butyrate
Ethyl 4-(1-methyl-1,2,3,4-tetrazol-5-yl)thio-butyrate
Isopropyl 3-(1-ethyl-1,2,3,4-tetrazol-5-yl)thio-propionate
Ethyl 4-(1-cyclooctyl-1,2,3,4-tetrazol-5-yl)thio-butyrate
Methyl 5-(1-phenyl-1,2,3,4-tetrazol-5-yl)valerate
Methyl 5-(1-cyclohexyl-1,2,3,4-tetrazol-5-yl)valerate
Methyl 5-(1-methyl-1,2,3,4-tetrazol-5-yl)valerate
4-(1-Methyl-1,2,3,4-tetrazol-5-yl)thio-butyric acid
4-(1-Phenyl-1,2,3,4-tetrazol-5-yl)thio-butyric acid
4-(1-Cyclohexyl-1,2,3,4-tetrazol-5-yl)thio-butyric acid
5-(1-Methyl-1,2,3,4-tetrazol-5-yl)valeric acid
5-(1-Phenyl-1,2,3,4-tetrazol-5-yl)valeric acid
5-(1-Cyclohexyl-1,2,3,4-tetrazol-5-yl)valeric acid
Methyl 3-(1-methyl-1,2,3,4-tetrazol-5-yl)methylthio-propionate
Ethyl 3-(1-phenyl-1,2,3,4-tetrazol-5-yl)methylthio-propionate
Methyl 3-(1-cyclohexyl-1,2,3,4-tetrazol-5-yl)methylthio-propionate
Methyl 3-[2-(1-methyl-1,2,3,4-tetrazol-5-yl)ethylthio]propionate
Methyl 4-(1-methyl-1,2,3,4-tetrazol-5-yl)methylthio-butyrate
Methyl 3-[2-methyl-3-(1-methyl-1,2,3,4-tetrazol-5-yl)propylthio]propionate
3-(1-Methyl-1,2,3,4-tetrazol-5-yl)methylthio-propionic acid
3-(1-Phenyl-1,2,3,4-tetrazol-5-yl)methylthio-propionic acid
3-(1-Cyclohexyl-1,2,3,4-tetrazol-5-yl)methylthio-propionic acid
3-[2-(1-Methyl-1,2,3,4-tetrazol-5-yl)ethylthio]propionic acid
4-(1-Methyl-1,2,3,4-tetrazol-5-yl)methylthiobutyric acid
Methyl 3-[1-(4-ethylphenyl)-1,2,3,4-tetrazol-5-yl]methylthio-propionate
Methyl 3-[1-(3,4-dimethoxyphenyl)-1,2,3,4-tetrazol-5-yl]methylthio-propionate
Methyl 3-[1-(4-chlorophenyl)-1,2,3,4-tetrazol-5-yl]methylthio-propionate
Methyl 3-[1-(3,4-dihydroxyphenyl)-1,2,3,4-tetrazol-5-yl]methylthio-propionate
Methyl 3-[1-(2-methylcyclohexyl)-1,2,3,4-tetrazol-5-yl]methylthio-propionate
Methyl 3-[1-(4-hydroxycyclohexyl)-1,2,3,4-tetrazol-5-yl]methylthio-propionate
Methyl 3-[1-(4-methoxycyclohexyl)-1,2,3,4-tetrazol-5-yl]methylthio-propionate
Methyl 3-[1-(4-chlorocyclohexyl)-1,2,3,4-tetrazol-5-yl]methylthio-propionate
3-[1-(4-Ethylphenyl)-1,2,3,4-tetrazol-5-yl]methylthio-propionic acid
3-[1-(2-Methoxyphenyl)-1,2,3,4-tetrazol-5-yl]methylthio-propionic acid
3-[1-(4-Hydroxyphenyl)-1,2,3,4-tetrazol-5-yl]methylthio-propionic acid
3-[1-(4-Methylcyclohexyl)-1,2,3,4-tetrazol-5-yl]methylthio-propionic acid
3-[1-(2-Methoxycyclohexyl)-1,2,3,4-tetrazol-5-yl]methylthio-propionic acid
3-[1-(4-Hydroxycyclohexyl)-1,2,3,4-tetrazol-5-yl]methylthio-propionic acid
3-[1-(2-Chlorocyclohexyl)-1,2,3,4-tetrazol-5-yl]methylthio-propionic acid
Methyl 4-[1-(4-methylphenyl)-1,2,3,4-tetrazol-5-yl]thio-butyrate
Methyl 4-[1-(3,4-dimethoxyphenyl)-1,2,3,4-tetrazol-5-yl]thio-butyrate
Methyl 4-[1-(2-hydroxyphenyl)-1,2,3,4-tetrazol-5-yl]thio-butyrate Methyl 4-[1-(2-methylcyclohexyl)-1,2,3,4-tetrazol-5-yl]thio-butyrate Methyl 4-[1-(4-hydroxycyclohexyl)-1,2,3,4-tetrazol-5-yl]thio-butyrate Methyl 4-[1-(3,4-dimethoxycyclohexyl)-1,2,3,4-tetrazol-5-yl]thio-butyrate 4-[1-(2-Methylphenyl)-1,2,3,4-tetrazol-5-yl]thio-butyrate acid 4-[1-(4-Methoxyphenyl)-1,2,3,4-tetrazol-5-yl]thio-butyric acid 4-[1-(3,4-Dimethoxyphenyl)-1,2,3,4-tetrazol-5-yl]thio-butyric acid 4-[1-(4-Methylcyclohexyl)-1,2,3,4-tetrazol-5-yl]thio-butyric acid 4-[1-(2-Hydroxycyclohexyl)-1,2,3,4-tetrazol-5-yl]thio-butyric acid 4-[1-(3,4-Dimethoxycyclohexyl)-1,2,3,4-tetrazol-5-yl]thio-butyric acid 5-[1-(2-Methoxyphenyl)-1,2,3,4-tetrazol-5-yl]valeric acid 5-[1-(4-Hydroxycyclohexyl)-1,2,3,4-tetrazol-5-yl]valeric acid 5-[1-(4-Methylphenyl)-1,2,3,4-tetrazol-5-yl]valeric acid 5-[1-(2-Chlorocyclohexyl)-1,2,3,4-tetrazol-5-yl]valeric acid 4-[1-(4-(N,N-Dimethylamino)phenyl)-1,2,3,4-tetrazol-5-yl]thio-butyric acid 4-[1-(4-Nitrophenyl)-1,2,3,4-tetrazol-5-yl]thio-butyric acid 4-[1-(4-Aminosulfonylphenyl)-1,2,3,4-tetrazol-5-yl]thio-butyric acid 4-[1-(2-Acetyloxyphenyl)-1,2,3,4-tetrazol-5-yl]thio-butyric acid 5-(1,2,3,4-Tetrazol-5-yl)valeric acid Methyl 5-(1,2,3,4-tetrazol-5-yl)valerate Methyl 4-(1,2,3,4-tetrazol-5-yl)thio-butyrate 4-(1,2,3,4-Tetrazol-5-yl)thio-butyric acid 3-(1,2,3,4-Tetrazol-5-yl)methylthio-propionic acid Methyl 3-(1,2,3,4-tetrazol-5-yl)methylthio-propionate The compounds of the present invention can be prepared by various processes. For instance, compounds [Ia] which are the compounds [I] wherein $R^2$ is the group:

can be prepared by a process as shown in the following Reaction Scheme-I:

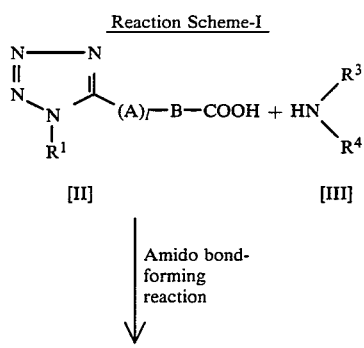

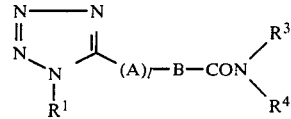

wherein $R^1$, $R^3$, $R^4$, A, B and l are as defined above.

The process as shown in Reaction Scheme-I is carried out by subjecting a carboxylic acid [II] and an amine [III] to an amido bond-forming reaction.

In the above process, a compound having an activated carboxyl group may be used instead of the carboxylic acid [II] and further a compound having an activated amino group instead of the amine [III]. The amido bond-forming reaction includes any conventional processes, such as (i) a mixed acid anhydride method, i.e. a process comprising reacting the carboxylic acid [II] with an alkyl halocarboxylate to give a mixed acid anhydride and reacting the mixed acid anhydride with the amine [III]; (ii) an active ester method, i.e. a process comprising converting the carboxylic acid [II] into an active ester, for example, p-nitrophenyl ester, N-hydroxysuccinimide ester, or N-hydroxybenzotriazole ester, and then reacting the active ester with the amine [III]; (iii) a carbodiimide method, i.e. a process comprising condensing the carboxylic acid [II] with the amine [III] in the presence of a dehydrating agent such as dicyclohexylcarbodiimide or carbonyldiimidazole; (iv) a carboxylic acid halide method, i.e. a process comprising reacting a halide compound of the carboxylic acid [II] with the amine [III]; (v) a process comprising converting the carboxylic acid [II] into an acid anhydride compound thereof by using a dehydrating agent such as acetic anhydride and then reacting the resulting acid anhydride with the amine [III]; and (vi) a process comprising converting the carboxylic acid [II] into an ester with a lower alcohol and reacting the resulting ester with the amine [III] under a high pressure and at a high temperature. Among these process, the mixed acid anhydride method and carboxylic acid halide method are preferable. The alkyl halocarboxylate used in the mixed acid anhydride method includes, for instance, methyl chloroformate, methyl bromoformate, ethyl chloroformate, ethyl bromoformate, isobutyl chloroformate, and the like. The mixed acid anhydride may be prepared by the well-known Schotten-Baumann reaction and can be used to the subsequent reaction with the amine [III] without isolation from the reaction mixture. The Schotten-Baumann reaction can be done in the presence of a basic compound. The basic compound includes all compounds which are usually used in Schotten-Baumann reaction, for example, organic bases such as triethylamine, trimethylamine, pyridine, dimethylaniline, N-methylmorpholine, 1,5-diazabicyclo[4.3.0]nonene-5 (DBN), 1,5-diazabicyclo[5.4.0]undecene-5 (DBU), 1,4-diazabicyclo[2.2.2]octane (DABCO), or the like, and inorganic bases such as potassium carbonate, sodium carbonate, potassium hydrogen carbonate, sodium hydrogen carbonate, or the like. The reaction is usually carried out at a temperature of −20° to 100° C., preferably 10° to 50° C., for about 5 minutes to about 10 hours.

The mixed acid anhydride method is usually carried out in an appropriate solvent. The solvent includes all solvent conventional in this method, for example, halogenated hydrocarbons such as methylene chloride, chloroform or dichloroethane, aromatic hydrocarbons such as benzene, toluene or xylene, ethers such as diethyl ether, tetrahydrofuran or dimethoxyethane, esters such as methyl acetate or ethyl acetate, aprotic polar solvents such as dimethylformamide, dimethylsulfoxide or hexamethylphosphoric triamide, and the like. The carboxylic acid [II], the alkyl halocarboxylate and the amine [III] are usually used in such an amount that the alkyl halocarboxylate and the amine [III] are each at least equimolar to the carboxylic acid [II], preferably 1 to 1.5 mole to 1 mole of the carboxylic acid [II].

The carboxylic acid halide method is carried out by reacting the carboxylic acid [II] with a halogenating agent to obtain a halide compound of the carboxylic acid [II] and then reacting the resulting carboxylic acid halide with the amine [III] after isolating and purifying the halide from the reaction mixture or without isolation.

The reaction of the carboxylic acid [II] and the halogenating agent is carried out in the presence or absence of a solvent. The solvent includes all solvents which do not give undesirable effect to the reaction, for example, aromatic hydrocarbons such as benzene, toluene or xylene, halogenated hydrocarbons such as chlorofrom, methylene chloride or carbon tetrachloride, ethers such as dioxane, tetrahydrofuran or diethyl ether, aprotic polar solvents such as dimethylformamide or dimethylsulfoxide, and the like. The halogenating agent includes any conventional halogenating agent which can convert the hydroxy group of the carboxyl group into halogen, for example, thionyl chloride, phosphorus oxychloride, phosphorus oxybromide, phosphorus pentachloride, phosphorus pentabromide, or the like.

The ratio of amount of the carboxylic acid [II] and the halogenating agent is not critical, but when the reaction is carried out in the absence of a solvent, the latter i.e. the acid [II], is used in a largely excess amount, and when the reaction is carried out in the presence of a solvent, the latter is used in an amount equivalent or more to the former, preferably 2 to 4 moles to 1 mole of the former. The reaction temperature and reaction time are not critical either, but the reaction is usually carried out at a temperature of room temperature to 100° C., preferably 50° to 80° C., for 30 minutes to 6 hours.

The reaction of the carboxylic acid halide with the amine [III] is usually carried out in the presence of a dehydrohalogenating agent. The dehydrohalogenating agent is usually basic compounds. The basic compounds used as the dehydrohalogenating agent include all conventional compounds, for example, inorganic bases such as sodium hydroxide, potassium hydroxide, sodium carbonate, potassium carbonate, sodium hydrogen carbonate, potassium hydrogen carbonate or silver carbonate, alkali metals such as sodium or potassium, alcoholates such as sodium methylate or sodium ethylate, organic bases such as triethylamine, pyridine, N,N-dimethylaminopyridine, 1,5-diazabicyclo[4.3.0]nonene-5 (DBN), 1,5-azabicyclo[5.4.0]undecene-5 (DBU) or 1,4-diazabicyclo[2.2.2]octane (DABCO)], or the like. The amine [III] may be used in a largely excess amount instead of using the dehydrohalogenating agent. The reaction may be carried out in the presence or absence of a solvent. The solvent includes any inert solvent which does not give undesirable effect to the reaction, for example, halogenated hydrocarbons such as chloroform, methylene chloride or carbon tetrachloride, ethers such as diethyl ether, tetrahydrofuran or dioxane, aromatic hydrocarbons such as benzene, toluene or xylene, esters such as methyl acetate or ethyl acetate, aprotic polar solvents such as N,N-dimethylformamide, dimethylsulfoxide or hexamethylphosphoric triamide, and the like.

The ratio of amount of the carboxylic acid halide and the amine [III] is not critical, but when the reaction is carried out in the absence of a solvent, the latter, i.e. the amine [III], is usually used in a largely excess amount, and when the reaction is carried out in the presence of a solvent, the latter is usually used in an amount of equivalent or more to the former, preferably 1 to 2 moles to 1 mole of the former. The reaction temperature and reaction time are not critical either, but the reaction is usually carried out at a temperature of $-30°$ to $100°$ C., preferably $0°$ to $50°$ C., for 30 minutes to 12 hours.

The compounds [Ib] which are the compounds [I] wherein l is 1 can be prepared by a process as shown in the following Reaction Scheme-II:

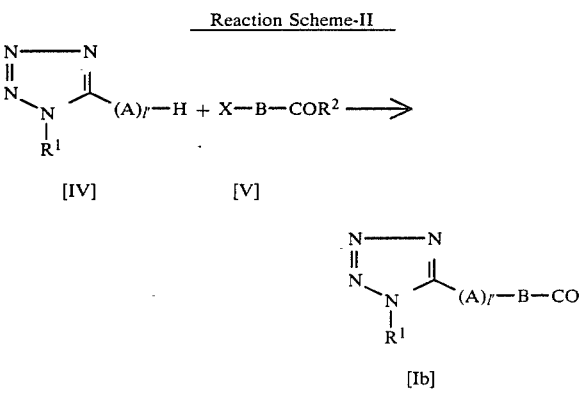

wherein l' is 1, X is a halogen, and $R^1$, $R^2$ and A are as defined above.

The dehydrohalogenation reaction of a 5-mercaptotetrazole derivative [IV] and a haloalkanecarboxylic acid derivative [V] in the above Reaction Scheme-II is usually carried out in the presence of the same dehydrohalogenating agent as used in the above Reaction Scheme-I. The reaction may be carried out in the presence or absence of a solvent. The solvent includes all inert solvents which do not give undesirable effect to the reaction, for example, alcohols such as methanol, ethanol, propanol, butanol or ethylene glycol, ethers such as diethyl ether, tetrahydrofuran, dioxane, monoglyme or diglyme, ketones such as acetone or methyl ethyl ketone, aromatic hydrocarbons such as benzene, toluene or xylene, esters such as methyl acetate or ethyl acetate, aprotic polar solvents such as N,N-dimethylformamide, dimethylsulfoxide or hexamethylphosphoric triamide, and the like. Besides, it is preferable to do the reaction in the presence of a metal iodide such as sodium iodide or potassium iodide.

The ratio of amount of the compound [IV] and the compound [V] is not critical, but when the reaction is carried out in the absence of a solvent, the latter, i.e. the compound [V], is used in a largely excess amount, and when the reaction is carried out in the presence of a solvent, the latter is used in an amount of 1 to 5 moles, preferably 1 to 2 moles, to 1 mole of the former. The reaction temperature and reaction time are not critical either, but the reaction is usually carried out at a temperature of −30° to 200° C., preferably 0° to 160° C., for about 1 to 30 hours.

Compounds [Ic] which are the compounds [I] wherein l is 0 and $R^2$ is a lower alkoxy can be prepared by a process as shown in the following Reaction Scheme-III:

Reaction Scheme-III

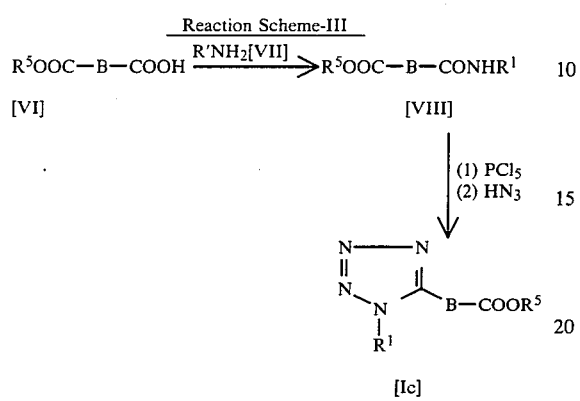

wherein $R^1$ and B are as defined above, and $R^5$ is a lower alkyl.

The reaction of a carboxylic acid [VI] and an amine [VII] in the above Reaction Scheme-III may preferably be carried out under the same conditions as shown in the mixed acid anhydride method and carboxylic acid halide method as mentioned in the above Reaction Scheme-I.

The reaction of a haloamide [VIII] with phosphorus pentachloride: $PCl_5$ is usually carried out in a solvent. The solvent includes all inert solvents which do not give undesirable effect to the reaction, for example, aromatic hydrocarbons such as benzene, toluene or xylene, halogenated aromatic hydrocarbons such as chlorobenzene or bromobenzene, ethers such as diethyl ether or dioxane, aliphatic hydrocarbons such as n-hexane or n-heptane, and the like. The ratio of amount of the haloamide [VIII] and $PCl_5$ is not critical, but usually, the latter, i.e. $PCl_5$, is used in an amount of 1 to 2 moles, preferably 1 to 1.2 mole, to 1 mole of the former. The reaction temperature and reaction time are not critical either, but the reaction is usually carried out at a temperature of −20° to 50° C., preferably 0° to 25° C., for 30 minutes to 5 hours.

The above reaction of the haloamide [VIII] with $PCl_5$, there is formed a haloimine derivative, and this compound is subsequently reacted with hydrogen azide: $HN_3$ without isolation from the reaction mixture. The reaction is usually carried out in an appropriate solvent such as benzene, xylene, diethyl ether, n-hexane, or the like. The hydrogen azide is usually used in an amount of 1 to 5 moles, preferably 1 to 3 moles, to 1 mole of the haloimine derivative. The reaction is usually carried out at a temperature of 0° to 150° C. for 3 hours to 2 days.

Compounds [Id] which are the compounds [I] wherein A is a lower alkylenethio can be prepared by a process as shown in the following Reaction Scheme-IV:

Reaction Scheme-IV

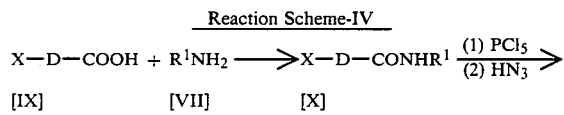

-continued
Reaction Scheme-IV

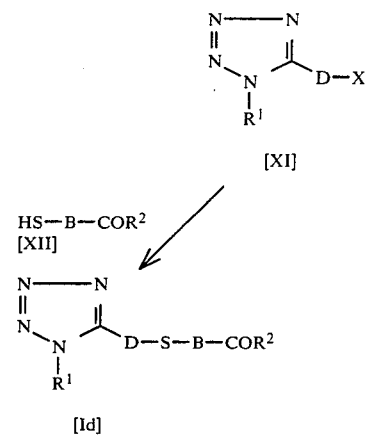

wherein X, $R^1$, $R^2$, and B are as defined above, and D is a lower alkylene.

In Reaction Scheme-IV, the reaction of a compound [IX] and a compound [VII] and the reaction of a compound [X] and $PCl_5$ followed by the reaction with $HN_3$ are carried out under the same reaction conditions as in the reaction of the compound [VI] and the compound [VII] and the reaction of the compound [VIII] and $PCl_5$ followed by the reaction with $HN_3$ in the above Reaction Scheme-III, respectively. Besides, the reaction of a compound [XI] and a compound [XII] is carried out under the same reaction conditions as in the reaction of the compound [IV] and the compound [V] in the above Reaction Scheme-II.

Moreover, Compounds [Ie] which are the compounds [I] wherein $R^2$ is a lower alkoxy can be converted into compounds [If] which are the compounds [I] wherein $R^2$ is hydroxy by hydrolysis thereof, as shown in the following Reaction Scheme-V:

Reaction Scheme-V

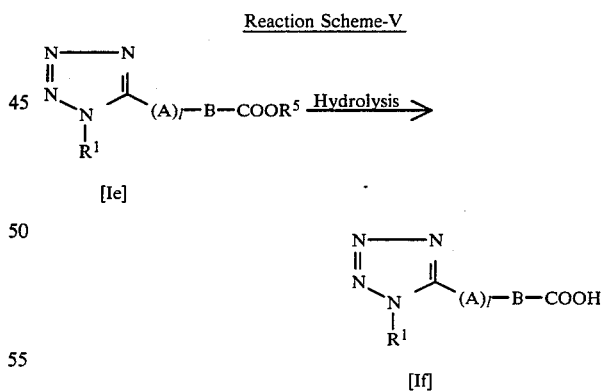

wherein A, l, B, $R^1$, are as defined above.

Hydrolysis of the compound [Ie] can be carried out by conventional methods, for instance, in the presence of a basic compound such as sodium hydroxide, potassium hydroxide or barium hydroxide, or a mineral acid such as sulfuric acid, hydrochloric acid or boric acid. This hydrolysis is preferably carried out in an appropriate solvent. The solvent includes all conventional solvents which do not give undesirable effect to the reaction, and suitable examples are water and lower alcohols such as methanol, ethanol, isopropanol, or the like.

The reaction temperature and reaction time are not critical, but the hydrolysis is usually carried out at a temperature of room temperature to 150° C., preferably 50° to 110° C., for about 30 minutes to 10 hours.

The starting compounds used in the above Reaction Scheme-I to V are partially known and are partially novel. For instance, the compounds [II] used in Reaction Scheme-I are novel and can be prepared by the processes as shown in Reaction Schemes-II, III, IV and V. Another starting compounds [III] are partially known and include novel compounds, which are prepared by the processes as shown in the following Reaction Schemes-VI and VII:

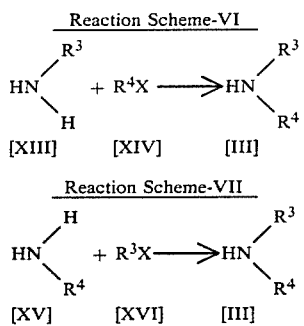

wherein $R^3$ and $R^4$ are as defined above, and X is a halogen.

In the above Reaction Schemes-VI and VII, the reaction of an amine [XIII] and a halogen compound [XIV] and the reaction of an amine [XV] and a halogen compound [XVI] are carried out under the same reaction conditions as used in the dehydrohalogenation reaction in Reaction Scheme-II.

The compounds [IV] used in Reaction Scheme-II are known and another starting compounds [V] are partially known and are partially novel. For example, compounds [Va] which are the compounds [V] wherein $R^2$ is

are prepared by a process as shown in the following Reaction Scheme-VIII:

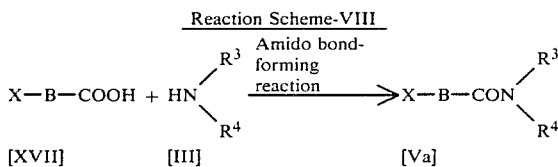

wherein X, B, $R^3$ and $R^4$ are as defined above.

The reaction of a known halocarboxylic acid [XVII] and an amine [III] can be carried out under the same reaction conditions as used in the amido bond-forming reaction in Reaction Scheme-I.

The starting compounds used in Reaction Schemes-III and VI are known. The starting compounds used in Reaction Scheme-V can be prepared by the same process as used in Reaction Schemes-II to IV.

The compounds [I] having an acidic group may be converted into a salt thereof with a pharmaceutically acceptable basic compound. The basic compound includes metal hydroxides such as sodium hydroxide or potassium hydroxide, alkali metal alcoholates such as sodium methylate or potassium ethylate, and the like. The compounds [I] having a basic group may also be converted into a salt with a pharmaceutically acceptable acid. The pharmaceutically acceptable acid includes inorganic acids such as sulfuric acid, nitric acid, hydrochloric acid or hydrobromic acid, and organic acids such as acetic acid, p-toluenesulfonic acid, ethanesulfonic acid, oxalic acid, maleic acid, succinic acid or benzoic acid.

The compounds obtained in the above processes can easily be isolated from the reaction mixture and purified by conventional methods. For instance, the isolation can be carried out by precipitation, extraction, recrystallization, distillation, column chromatography, preparative thin layer chromatography, and the like.

The compounds [I] or their pharmaceutically acceptable salts of the present invention are useful for the treatment of peptic ulcers and duodenal ulcers and usually used in the form of conventional pharmaceutical preparations. The pharmaceutical preparations can be prepared by using conventional diluents and carriers; such as fillers, bulking agents, binding agents, wetting agents, disintegrators, surface active agents, lubricants, or the like. The preparations may be in various forms, such as tablets, pills, powders, solutions, suspensions, emulsions, granules, capsules, suppositories, injections (solution, suspension, etc.), and the like. The tablets can be prepared by using conventional carriers, such as excipients (e.g. lactose, sucrose, sodium chloride, glucose, urea, starches, calcium carbonate, kaolin, crystalline cellulose, silicic acid, etc.), binding agents (e.g. water, ethanol, propanol, simple syrup, aqueous glucose solution, aqueous solution of starches, aqueous gelatine solution, carboxymethyl cellulose, shellac, methyl cellulose, potassium phosphate, polyvinyl pyrrolidone, etc.), disintegrators (e.g. dry starches, sodium arginate, agar powder, laminaran powder, sodium hydrogen carbonate, calcium carbonate, polyoxyethylene sorbitan fatty acid esters, sodium laurylsulfate, monoglyceryl stearate, starches, lactose, etc.), disintegration inhibitors (e.g. sucrose, stearin, cacao butter, hydrogenated oils, etc.), absorption accelerators (e.g. quaternary ammonium salt, sodium laurylsulfate, etc.), humectants (e.g. glycerin, starches, etc.), adsorbents (e.g. starches, lactose, kaolin, bentonite, colloidal silica, etc.), lubricants (e.g. purified talc, stearic acid salts, boric acid powder, polyethylene glycol, etc.), and the like. The tablets may be in the form of sugar coating tablets, genlatin coating tablets, enteric coating tablets, film coating tablets, double or multiple layers tablets, and the like. The pills can be prepared by using conventional carriers, such as excipients (e.g. glucose, lactose, starches, cacao butter, hardened vegetable oils, kaolin, talc, etc.), binding agents (e.g. gum arabic powder, tragacanth powder, gelatin, ethanol, etc.), disintegrators (e.g. laminaran, agar, etc.), and the like. The suppositories can be prepared by using conventional carriers, such as polyethylene glycol, cacao butter, higher alcohols or their esters, gelatin, semisynthetic glycerides, or the like. When the active compounds are prepared in the form of an injection, a solution or suspension containing the active compounds is sterilized and made isotonic to blood. The injections in the form of a solution, emulsion or suspension can be prepared by using conventional diluents, such as water, ethyl alcohol, propylene glycol, ethoxylated isostearyl alcohol, polyoxy-isostearyl alcohol, polyoxyethylene sorbitan fatty esters, or the like. The injection preparation may be made isotonic by adding thereto a sufficient amount of sodium chloride, glucose, glycerin, or the like and may optionally be incorporated with conventional solubilizers, buffer solutions, pain killers, colorants, preservatives, perfumes, flavors, sweetening agents, and other medicaments.

The anti-ulcer preparations of the present invention may contain a wide range of amount of the active compounds and contains usually about 1 to 70% by weight, preferably 5 to 50% by weight, of the active compounds of the present invention based on the total weight of the preparations.

The administration route of the anti-ulcer preparations of the present invention is not restricted, and suitable administration route is determined by the forms of the preparations, age, sex and other conditions of patients to be treated, severity of disease, and the like. Tablets, pills, solutions, suspensions, emulsions, granules and capsules are usually administered in oral route. Injections are usually administered in intravenous route alone or optionally together with an appropriate adjuvant such as glucose or amino acids or may be administered alone in intramuscular, intracutaneous, subcutaneous, or intraperitoneal route.

The dose of the active compounds of the present invention may vary with the usage, age, sex and other conditions of patients to be treated, severity of diseases, or the like, but is usually in the range of 0.6 to 50 mg/kg of body weight per day. The active compounds of the present invention is preferably contained in the anti-ulcer preparations in a dosage unit of 10 to 1000 mg.

The compounds of the present invention and preparation thereof are illustrated by the following Reference Examples and Examples, but are not limited thereto.

REFERENCE EXAMPLE 1

To ethyl acetate (400 ml) is added N-methylcyclohexylamine (26 ml), and to the mixture are added dropwise with stirring 4-chlorobutyryl chloride (25 ml) and triethylamine (33.5 ml) over a period of 20 minutes with keeping the inner temperature at 10° to 20° C. by ice-cooling. The mixture is further stirred at room temperature for one hour. After the reaction, water is added to the reaction mixture. The organic layer is separated and washed with water an aqueious saturated potassium carbonate solution, 10% aqueous hydrochloric acid and water in order, and then dried over anhydrous sodium sulfate. After filtering off sodium sulfate, the mother liquor is concentrated and distilled under reduced pressure to give N-methyl-N-cyclohexyl-4-chlorobutyramide (41.5 g), b.p. 133°–136° C./2 mm Hg.

REFERENCE EXAMPLE 2

N-Ethyl-cyclohexylamine (2.6 g) is dissolved in dry benzene (20 ml). To the solution are added dropwise with stirring chloroacetyl chloride (2.6 g) and triethylamine (2.4 g) under ice-cooling. The mixture is stirred under ice-cooling for one hour and further at room temperature for one hour. The reaction mixture is poured onto ice-water and extracted with ether. The ether layer is washed with an aqueous sodium hydrogen carbonate solution and an aqueous saturated sodium chloride solution and dried over anhydrous magnesium sulfate. After distilling off the solvent, the resulting residue is distilled under reduced pressure to give N-ethyl-N-cyclohexyl-chloroacetamide (3 g), b.p. 118°–120° C./0.2 mmHg.

REFERENCE EXAMPLES 3 AND 4

In the same manner as described in Reference Example 2, the following compounds are prepared. N-Ethyl-N-cyclohexyl-4-chlorobutyramide, b.p. 120°–130° C./1.5 mmHg N-Ethyl-N-cyclohexyl-3-chloropropionamide, b.p. 103°–110° C./0.15 mmHg

REFERENCE EXAMPLE 5

To monomethyl adipate (6 g) is added thionyl chloride (10 ml), and the mixture is refluxed for one hour. Excess thionyl chloride is distilled off, and benzene is added to the residue and thionyl chloride is further removed by azeotropic distillation.

Separately, aniline (4.2 g) and potassium carbonate (5.2 g) are dissolved in acetone (100 ml) and water (15 ml). To the mixture is added dropwise with stirring the chloride compound obtained above under ice-cooling. The mixture is stirred under ice-cooling for one hour and further at room temperature for 2 hours. After distilling off acetone, water is added to the residue, and the mixture is extracted with chloroform. The chloroform layer is washed with an aqueous saturated sodium chloride solution and dried over magnesium sulfate. Chloroform is distilled off to give methyl phenyladipinamate (9 g).

NMR: $\delta_{ppm}^{CDCl_3}$ 1.40–1.90 (4H, m), 2.10–2.50 (4H, m), 3.66 (3H, s), 6.80–7.70 (5H, m), 8.55 (1H, br.s)

REFERENCE EXAMPLES 6 AND 7

In the same manner as described in Reference Example 5, the following compounds are obtained.

Methyl N-cyclohexyladipinamate, faint brown prisms (recrystallized from methanol-water), m.p. 72°–74° C.

Methyl N-methyladipinamate, colorless liquid, b.p. 136°–140° C./0.7 mmHg

REFERENCE EXAMPLE 8

A 40% aqueous methylamine solution (46.5 ml) is dissolved in acetone (300 ml). To the solution are added potassium carbonate (45.6 g) and water (100 ml), and thereto is added dropwise with stirring chloroacetyl chloride (24.3 ml) under ice-cooling. The mixture is stirred under ice-cooling for one hour and further at room temperature for 2 hours. After distilling off acetone, water is added to the residue, and the mixture is extracted with chloroform. The chloroform layer is washed with an aqueous saturated sodium chloride solution and dried over magnesium sulfate. After distilling off chloroform, the residue is distilled under reduced pressure to give N-methyl-chloroacetamide (15.5 g), colorless liquid, b.p. 107°–109° C./27 mmHg.

REFERENCE EXAMPLE 9

N-Methyl-chloroacetamide (10.8 g) is dissolved in benzene (100 ml), and thereto is added with stirring phosphorus pentachloride (10.8 g) at below 15° C. The mixture is stirred at room temperature for one hour and then allowed to staand overnight. The mixture is slowly refluxed for 2 hours. The reaction mixture is concentrated, and thereto is added ice-water, and the mixture is extracted with chloroform. The chloroform layer is washed with water, a dilute aqueous sodium hydroxide solution and water, dried over magnesium sulfate and distilled to remove chloroform. The resulting residue is subjected to column chromatography (Wakogel C-200, made by Wako Pure Chemical Industry, eluting agent, chloroform:methanol=50:1, V/V) to isolate 1-methyl-5-chloromethyl-1,2,3,4-tetrazole (8.5 g).

EXAMPLE 1

4-(1-Methyl-1,2,3,4-tetrazol-5-yl)thio-butyric acid (2 g) is dissolved in dry tetrahydrofuran (30 ml), and thereto is added triethylamine (1.1 g). To the mixture is added dropwise with stirring isobutyl chloroformate (1.5 g) under ice-cooling. The mixture is stirred at room temperature for 30 minutes. To the mixture is further added dropwise with stirring diethylamine (0.9 g) at room temperature, and the mixture is stirred for 2 hours. The mixture is concentrated under reduced pressure, and the resulting residue is purified by subjecting it to column chromatography (Kieselgel 60, made by Merck & Co.). By eluting with n-hexane-ethyl acetate (1:1), there is obtained N,N-diethyl-4-(1-methyl-1,2,3,4-tetrazol-5-yl)thio-butyramide (1.4 g), colorless liquid, $n_D^{17.5} = 1.5227$ NMR: $\delta_{ppm}^{CDCl_3}$ 1.04 (3H, t, J=7 Hz), 1.12 (3H, t, J=7 Hz), 1.90–2.70 (4H, m), 3.00–3.60 (6H, m), 3.88 (3H,s)

Elementary analysis for $C_{10}H_{19}N_5OS$: Calcd. (%): C,46.67; H,7.44; N,27.21 Found (%): C,46.78; H,7.51; N,27.29

EXAMPLES 2 TO 5

In the same manner as described in Example 1, the following compounds are obtained from appropriate starting materials.

(2) N-Ethyl-N-cyclohexyl-4-(1-methyl-1,2,3,4-tetrazol-5-yl)thio-butyramide, colorless liquid, $n_D^{17.5} = 1.5327$ NMR: $\delta_{ppm}^{CDCl_3}$ 0.90–1.40 (3H, m), 1.20–2.00 (10H, m), 2.00–2.80 (4H, m), 3.00–3.60 (6H, m), 3.95 (3H, s), 3.50–4.50 (1H, m)

(3) N-Ethyl-N-phenyl-4-(1-methyl-1,2,3,4-tetrazol-5-yl)thio-butyramide, pale yellow liquid, $n_D^{26} = 1.5534$ NMR: $\delta_{ppm}^{CDCl_3}$ 1.12 (3H, t, J=7 Hz), 1.70–2.40 (4H, m), 3.32 (2H, t, J=7 Hz), 3.74 (2H, q, J=14 Hz, 7 Hz), 3.90 (3H, s), 7.00–7.60 (5H, m)

(4) 5-(3-Morpholinocarbonylpropylthio)-1-methyl-1,2,3,4-tetrazole, white needles (recrystallized from petroleum ether-ethanol), m.p. 71°–73° C.

(5) 5-[3-(4-Acetylpiperadinocarbonyl)propylthio]-1-methyl-1,2,3,4-tetrazole, white crystalline powder (recrystallized from ligroine-acetone), m.p. 90°–91.5° C.

EXAMPLE 6

4-(1-Methyl-1,2,3,4-tetrazol-5-yl)thio-butyric acid (45 mmole) is dissolved in tetrahydrofuran (50 ml), and thereto is added DBU (50 mmole). To the mixture is added dropwise with stirring isobutyl chloroformate (50 mmole) under ice-cooling and the mixture is stirred at room temperature for 30 minutes. To the mixture is added dropwise 2-(3,4-dimethoxyphenyl)ethylamine (54 mmole) and the mixture is further stirred at room temperature for 2 hours. After the solvent is distilled off under reduced pressure, the resulting residue is extracted with chloroform. The chloroform layer is washed with 5% aqueous hydrochloric acid, an aqueous saturated sodium hydrogen carbonate solution and an aqueous saturated sodium chloride solution and dried over anhydrous sodium sulfate. After distilling off chloroform, the residue is subjected to column chromatography (Wakogel C-200, eluting agent, chloroform) to isolate N-[2-(3,4-dimethoxyphenyl)ethyl]-4-(1-methyl-1,2,3,4-tetrazol-5-yl)thio-butyramide (yield: 41%) which is recrystallized from hexane-chloroform, colorless flaks, m.p. 70.5°–71.5° C.

Elementary analysis for $C_{16}H_{23}N_5O_3S$: Calcd. (%): C,52.59; H,6.34; N,19.16 Found (%): C,52.51; H,6.16; N,19.10

EXAMPLES 7 TO 58

In the same manner as described in Example 6, the following compounds are prepared from appropriate starting materials.

(7) N-Hexyl-4-(1-methyl-1,2,3,4-tetrazol-5-yl)-thio-butyramide, colorless flaks (recrystallized from hexane-ether), m.p. 41°–42° C.

(8) N-Cyclohexyl-4-(1-methyl-1,2,3,4-tetrazol-5-yl)thio-butyramide, colorless needles (hexane-ethyl acetate), m.p. 116.5°–117.5° C.

(9) N-Cyclooctyl-4-(1-methyl-1,2,3,4-tetrazol-5-yl)thio-butyramide, colorless liquid, $n_D^{14} = 1.5323$

(10) N-Cyclododecanyl-4-(1-methyl-1,2,3,4-tetrazol-5-yl)thio-butyramide, colorless needles (hexane-ethyl acetate), m.p. 119°–120° C.

(11) N-Butyl-4-(1-methyl-1,2,3,4-tetrazol-5-yl)thio-butyramide, colorless liquid, $n_D^{16.5} = 1.5198$

(12) N-(2-Hydroxyethyl)-4-(1-methyl-1,2,3,4-tetrazol-5-yl)thio-butyramide, colorless liquid, $n_D^{14.5} = 1.5350$

(13) N-Ethyl-N-benzyl-4-(1-methyl-1,2,3,4-tetrazol-5-yl)thio-butyramide, colorless liquid, $n_D^{19} = 1.5596$

(14) N-Butyl-N-cyclohexyl-4-(1-methyl-1,2,3,4-tetrazol-5-yl)thio-butyramide, colorless liquid, $n_D^{19} = 1.5222$

(15) N,N-Dibutyl-4-(1-methyl-1,2,3,4-tetrazol-5-yl)thio-butyramide, colorless liquid, $n_D^{19} = 1.5049$

(16) N,N-Dibenzyl-4-(1-methyl-1,2,3,4-tetrazol-5-yl)thio-butyramide, colorless liquid, $n_D^{19} = 1.5773$

(17) N,N-Diisopropyl-4-(1-methyl-1,2,3,4-tetrazol-5-yl)thio-butyramide, colorless liquid, $n_D^{19.5} = 1.5111$

(18) N,N-Dicyclohexyl-4-(1-methyl-1,2,3,4-tetrazol-5-yl)thio-butyramide, colorless needles (hexane), m.p. 91°–92° C.

(19) N-Benzyl-N-tert-butyl-4-(1-methyl-1,2,3,4-tetrazol-5-yl)thio-butyramide, colorless needles (hexane), m.p. 86.5°–87.5° C.

(20) N-Cyclohexyl-N-[2-(3,4-dimethoxyphenyl)ethyl]-4-(1-methyl-1,2,3,4-tetrazol-5-yl)thio-butyramide, colorless liquid, $n_D^{16}=1.5470$

(21) N-Methyl-N-(2-thienylmethyl)-4-(1-methyl-1,2,3,4-tetrazol-5-yl)thio-butyramide, colorless liquid, $n_D^{16}=1.5706$

(22) N-Benzyl-N-[2-(3,4-dimethoxyphenyl)ethyl]-4-(1-methyl-1,2,3,4-tetrazol-5-yl)thio-butyramide, colorless liquid, $n_D^{16}=1.5659$

(23) N-Cyclohexyl-N-(2-hydroxyethyl)-4-(1-methyl-1,2,3,4-tetrazol-5-yl)thio-butyramide, colorless liquid, $n_D^{14.5}=1.5372$

(24) N,N-Dihexyl-4-(1-methyl-1,2,3,4-tetrazol-5-yl)thio-butyramide, colorless liquid, $n_D^{15}=1.5011$

(25) N-Ethyl-N-[2-(3,4-dimethoxyphenyl)ethyl]-4-(1-methyl-1,2,3,4-tetrazol-5-yl)thio-butyramide, colorless liquid, $n_D^{14}=1.5451$

(26) N-tert-Butyl-4-(1-methyl-1,2,3,4-tetrazol-5-yl)thio-butyramide, colorless plates (hexane-ethyl acetate), m.p. 71°–73° C.

(27) N-Ethyl-4-(1-methyl-1,2,3,4-tetrazol-5-yl)thio-butyramide, colorless liquid, $n_D^{15}=1.5319$

(28) N-Benzyl-4-(1-methyl-1,2,3,4-tetrazol-5-yl)thio-butyramide, colorless needles (hexane-ethyl acetate), m.p. 65°–66° C.

(29) N-Hexyl-N-cyclohexyl-4-(1-methyl-1,2,3,4-tetrazol-5-yl)thio-butyramide, colorless liquid, $n_D^{16}=1.5182$

(30) N-Cyclohexyl-N-(2-hydroxyethyl)-4-(1-methyl-1,2,3,4-tetrazol-5-yl)thio-butyramide, colorless liquid, $n_D^{14.5}=1.5372$

(31) N-Phenyl-4-(1-methyl-1,2,3,4-tetrazol-5-yl)thio-butyramide, colorless needles (hexane-ethyl acetate), m.p. 106°–107° C.

(32) N-(2-Pyridyl)-4-(1-methyl-1,2,3,4-tetrazol-5-yl)thio-butyramide, colorless needles (hexane-ethyl acetate), m.p. 95°–96° C.

(33) N-(3-Pyridyl)-4-(1-methyl-1,2,3,4-tetrazol-5-yl)thio-butyramide, colorless plates (ethyl acetate), m.p. 110.5°–113° C.

(34) N-(2-Pyrimidyl)-4-(1-methyl-1,2,3,4-tetrazol-5-yl)thio-butyramide, colorless granules (hexane-ethyl acetate), m.p. 108°–110° C.

(35) N-Furfuryl-4-(1-methyl-1,2,3,4-tetrazol-5-yl)thio-butyramide, colorless flaks (hexane-ethyl acetate), m.p. 71°–73° C.

(36) N-(4-Aminosulfonylphenyl)-4-(1-methyl-1,2,3,4-tetrazol-5-yl)thio-butyramide, colorless needles (methanol), m.p. 169.5°–170.5° C.

(37) N-[4-(N,N-Dimethylamino)phenyl]-4-(1-methyl-1,2,3,4-tetrazol-5-yl)thio-butyramide, colorless prisms (hexane-ethyl acetate), m.p. 144°–147° C.

(38) N-(2-Methyl-3-chlorophenyl)-4-(1-methyl-1,2,3,4-tetrazol-5-yl)thio-butyramide, colorless needles (hexane-ethyl acetate), m.p. 104.5°–105.5° C.

(39) N-(4-Nitrophenyl)-4-(1-methyl-1,2,3,4-tetrazol-5-yl)thio-butyramide, colorless needles (ethyl acetate), m.p. 194°–195° C.

(40) N-(2-Methoxyphenyl)-4-(1-methyl-1,2,3,4-tetrazol-5-yl)thio-butyramide, colorless needles (hexane-ethyl acetate), m.p. 79.5°–82° C.

(41) N-Methyl-N-(2-tetrahydropyranyl)-4-(1-methyl-1,2,3,4-tetrazol-5-yl)thio-butyramide, colorless liquid, $n_D^{14}=1.5273$

(42) N-Ethyl-N-(2-pyridyl)-4-(1-methyl-1,2,3,4-tetrazol-5-yl)thio-butyramide, colorless liquid, $n_D^{16}=1.5623$

(43) N-Ethyl-N-(3-pyridyl)-4-(1-methyl-1,2,3,4-tetrazol-5-yl)thio-butyramide, colorless liquid, $n_D^{16}=1.5618$

(44) N-Ethyl-N-cyclopentyl-4-(1-methyl-1,2,3,4-tetrazol-5-yl)thio-butyramide, colroless liquid, $n_D^9=1.5384$

(45) N-Ethyl-N-cyclohexylmethyl-4-(1-methyl-1,2,3,4-tetrazol-5-yl)thio-butyramide, colorless liquid, $n_D^{11}=1.5293$

(46) N-Isopropyl-N-cyclohexyl-4-(1-methyl-1,2,3,4-tetrazol-5-yl)thio-butyramide, colorless liquid, $n_D^{15}=1.5238$

(47) N-Ethyl-N-(4-hydroxycyclohexyl)-4-(1-methyl-1,2,3,4-tetrazol-5-yl)thio-butyramide, colorless liquid, $n_D^9=1.5363$

(48) N-Ethyl-N-(2-hydroxycyclohexyl)-4-(1-methyl-1,2,3,4-tetrazol-5-yl)thio-butyramide, colorless needles (hexane-ethyl acetate), m.p. 132°–133° C.

(49) N-Ethyl-N-(2-acetyloxycyclohexyl)-4-(1-methyl-1,2,3,4-tetrazol-5-yl)thio-butyramide, colorless liquid, $n_D^{11}=1.5218$

(50) N,N-Dipropyl-4-(1-methyl-1,2,3,4-tetrazol-5-yl)thio-butyramide, colorless liquid $n_D^{15}=1.5151$

(51) N-Butyl-N-phenyl-4-(1-methyl-1,2,3,4-tetrazol-5-yl)thio-butyramide, colorless liquid, $n_D^{15}=1.5509$

(52) N-Methyl-N-cyclohexyl-4-(1-methyl-1,2,3,4-tetrazol-5-yl)thio-butyramide, pale yellow liquid NMR: $\delta_{ppm}^{CCl_4}$ 1.00–2.00 (10H, br.), 1.80–2.70 (4H, m), 2.73 (3H, d, J=6 Hz), 3.28 (2H, t, J=6 Hz), 3.85 (3H, s), 3.20–4.50 (1H, m)

(53) N,N-Dimethyl-4-(1-methyl-1,2,3,4-tetrazol-5-yl)thio-butyramide, colorless liquid, $n_D^{16}=1.5327$

(54) N-Ethyl-N-cyclooctyl-4-(1-methyl-1,2,3,4-tetrazol-5-yl)thio-butyramide, colorless liquid, $n_D^{16}=1.5309$

(55) 5-[3-(4-Methylpiperazinocarbonyl)propyl-thio]-1-methyl-1,2,3,4-tetrazol, colorless flaks (hexane-ethyl acetate), m.p. 65°–68° C.

(56) 5-(3-Piperidinocarbonylpropylthio)-1-methyl-1,2,3,4-tetrazole, colorless liquid, $n_D^{25}=1.5310$

(57) N-Ethyl-N-cycloheptyl-4-(1-methyl-1,2,3,4-tetrazol-5-yl)thio-butyramide, colorless liquid, $n_D^{18}=1.5290$

EXAMPLE 58

4-(1-Phenyl-1,2,3,4-tetrazol-5-yl)thio-butyric acid (45 mmole) is dissolved in tetrahydrofuran (50 ml) and thereto is added DBU (50 mmole). To the mixture is added dropwise with stirring isobutyl chloroformate (50 mmole) under ice-cooling. The mixture is stirred at room temperature for 30 minutes. To the mixture is added dropwise N-ethylcyclohexylamine (54 mmole) and the mixture is further stirred at room temperature for 2 hours. After distilling off the solvent under reduced pressure, the residue is extracted with chloroform. The chloroform layer is washed with 5% aqueous hydrochloric acid, an aqueous saturated sodium hydrogen carbonate solution and an aqueous saturated sodium chloride solution and dried over anhydrous sodium sulfate. Chloroform is distilled off and the resulting residue is subjected to column chromatography (Wakogel C-200, eluting solvent, chloroform) to isolate N-ethyl-N-cyclohexyl-4-(1-phenyl-1,2,3,4-tetrazol-5-yl)thio-butyramide (yield: 43%), colorless liquid, $n_D^{18}=1.5590$.

Elementary analysis for $C_{19}H_{27}N_5OS$:
Calcd. (%): C,61.10; H,7.29; N,18.75
Found (%): C,61.28; H,7.38; N,18.86

EXAMPLE 59

In the same manner as described in Example 58 except that N,N-diethylamine is used instead of N-ethyl-N-cyclohexylamine, there is obtained N,N-diethyl-4-(1-phenyl-1,2,3,4-tetrazol-5-yl)thio-butyramide, colorless liquid, $n_D^{18} = 1.5592$.

EXAMPLE 60

2-(1-Methyl-1,2,3,4-tetrazol-5-yl)thio-acetic acid (45 mmole) is dissolved in tetrahydrofuran (50 ml) and thereto is added DBU (50 mmole). To the mixture is added dropwise with stirring isobutyl chloroformate (50 mmole) under ice-cooling and the mixture is stirred at room temperature for 30 minutes. To the mixture is added dropwise N-ethyl-cyclohexylamine under ice-cooling, and the mixture is further stirred at room temperature for 2 hours. After distilling off the solvent under reduced pressure, the resulting residue is extracted with chloroform. The chloroform layer is washed with 5% aqueous hydrochloric acid, an aqueous saturated sodium hydrogen carbonate solution and an aqueous saturated sodium chloride solution and dried over anhydrous sodium sulfate. Chloroform is distilled off and the residue is subjected to column chromatograpy (Wakogel C-200, eluting solvent, benzene:chloroform=4:1, V/V) to isolate N-ethyl-N-cyclohexyl-2-(1-methyl-1,2,3,4-tetrazol-5-yl)thio-acetamide (yield: 52%) which is recrystallized from ether-petroleum ether, white prisms, m.p. 69°–71° C.

Elementary analysis for $C_{12}H_{21}N_5OS$: Calcd. (%): C,50.86; H,7.47; N,24.71 Found (%): C,50.75; H,7.55; N,24.78

EXAMPLES 61 AND 62

In the same manner as described in Example 60, the following compounds are prepared by using appropriate starting materials. (61) N-Ethyl-N-cyclohexyl-3-(1-methyl-1,2,3,4-tetrazol-5-yl)thio-propionamide, pale yellow liquid, $n_D^{26} = 1.5273$
(62) N-Ethyl-N-cyclohexyl-5-(1-methyl-1,2,3,4-tetrazol-5-yl)thio-valeramide, pale yellow liquid, $n_D^{25} = 1.5227$

EXAMPLE 63

4-(1-Cyclohexyl-1,2,3,4-tetrazol-5-yl)thio-butyric acid (45 mmole) is dissolved in tetrahydrofuran (50 ml) and thereto is added DBU (50 mmole). To the mixture is added dropwise with stirring isobutyl chloroformate under ice-cooling, and the mixture is stirred at room temperature for 30 minutes. To the mixture is added dropwise N-ethyl-cyclohexylamine (54 mmole), and the mixture is further stirred at room temperature for 2 hours. After distilling off the solvent under reduced pressure, the residue is extracted with chloroform. The chloroform layer is washed with 5% aqueous hydrochloric acid, an aqueous saturated sodium hydrogen carbonate and an aqueous saturated sodium chloride solution and dried over anhydrous sodium sulfate. Chloroform is distilled off and the resulting residue is subjected to column chromatography (Wakogel C-200, eluting solvent, benzene:chloroform=4:1, V/V) to isolate N-ethyl-N-cyclohexyl-4-(1-cyclohexyl-1,2,3,4-tetrazol-5-yl)thio-butyramide (yield: 47%), colorless liquid, $n_D^{18} = 1.5290$.

Elementary analysis for $C_{19}H_{33}N_5OS$: Calcd. (%): C,60.12; H,8.76; N,18.45 Found (%): C,59.95; H,8.62; N,18.55

EXAMPLE 64

To methylene chloride (50 ml) are added 4-(1-methyl-1,2,3,4-tetrazol-5yl)thio-butyric acid (45 mmole) and N-methylmorpholine (50 mmole). To the mixture is added dropwise with stirring methyl chloroformate (50 mmole) with keeping the inner temperature at 10°–20° C. by ice-cooling, and thereafter, the mixture is stirred at room temperature for 30 minutes. To the mixture is added 2-methoxycyclohexylamine (54 mmole), and the mixture is stirred at the same temperature for 4 hours. After the reaction, water is added to the reaction mixture. The organic layer is separated and washed with dilute aqueous sodium hydroxide solution, diluted hydrochloric acid and water in order, and dried over sodium sulfate. Inorganic materials are filtered off, and the mother liquor is concentrated. The resulting residue is subjected to column chromatograpy (Wakogel C-200, eluting solvent, benzene:chloroform=4:1, V/V) to isolate N-(4-methoxycyclohexyl)-4-(1-methyl-1,2,3,4-tetrazol-5-yl)thio-butyramide (yield: 43%), colorless liquid, $n_D^{11} = 1.5263$.

Elementary analysis for $C_{13}H_{23}N_5O_2S$: Calcd. (%): C,52.50; H,7.79; N,23.55 Found (%): C,52.56; H,7.71; N,23.63

EXAMPLE 65

To tetrahydrofuran (50 ml) are added 4-(1-methyl-1,2,3,4-tetrazol-5-yl)thio-butyric acid (45 mmole) and pyridine (50 mmole), and thereto is added dropwide with stirring methyl bromoformate (50 mmole) with keeping the inner temperature at 5°–15° C. by ice-cooling, and thereafter, the mixture is stirred at room temperature for one hour. To the mixture is added 4-methylcyclohexylamine (55 mmole), and the mixture is further stirred for 3 hours. After the reaction, the solvent is distilled off under reduced pressure, and the residue is dissolved in chloroform. The chloroform layer is washed with dilute aqueous sodium hydroxide solution, diluted hydrochloric acid and water in order, and dried over sodium sulfate. Inorganic materials are filtered off and the mother liquor is concentrated. The resulting residue is subjected to column chromatography (Wakogel C-200, eluting solvent, benzene:chloroform=4:1, V/V) to isolate N-(4-methylcyclohexyl)-4-(1-methyl-1,2,3,4-tetrazol-5-yl)thio-butyramide (yield: 45%).

Elementary analysis for $C_{13}H_{23}N_5OS$: Calcd. (%): C,52.50; H,7.79; N,23.55 Found (%): C,52.31; H,7.65; N,23.80

EXAMPLE 66

4-(1-Methyl-1,2,3,4-tetrazol-5-yl)thio-butyric acid (45 mmole) is dissolved in tetrahydrofuran (50 ml), and thereto is added DBU (50 mmole). To the mixture is added dropwise with stirring isobutyl chloroformate (50 mmole) under ice-cooling, and the mixture is stirred at room temperature for 30 minutes. To the mixture is added dropwise 4-(N,N-dimethylamino)cyclohexylamine (54 mmole), and the mixture is further stirred at room temperature for 2 hours. After distilling off the solvent under reduced pressure, the resulting residue is extracted with chloroform. The chloroform layer is washed with 5% aqueous hydrochloric acid, an aqueous saturated sodium hydrogen carbonate solution and an aqueous saturated sodium chloride solution and then dried over anhydrous sodium sulfate. Chloroform is distilled off, and the resulting residue is subjected to silica gel column chromatography (Wakogel C-200, eluting solvent, benzene:chloroform=4:1, V/V) to isolate N-[4-(N,N-dimethylamino)cyclohexyl]-4-(1-methyl-1,2,3,4-tetrazol-5-yl)thio-butyramide (yield: 47%).

Elementary analysis for $C_{14}H_{26}N_6OS$: Calcd. (%): C,51.51; H,8.03; N,25.74 Found (%): C,51.60; H,8.22; N,26.05

EXAMPLE 67

4-[1-(2-Methoxycyclohexyl)-1,2,3,4-tetrazol-5-yl]thio-butyric acid (45 mmole) is dissolved in tetrahydrofuran (50 ml), and thereto is added DBU (50 mmole). To the mixture is added dropwise with stirring isobutyl chloroformate (50 mmole) under ice-cooling, and the mixture is stirred at room temperature for 30 minutes. To the mixture is added dropwise N-ethyl-cyclohexylamine (54 mmole), and the mixture is further stirred at room temperature for 2 hours. The solvent is distilled off under reduced pressure, and the residue is extracted with chloroform. The chloroform layer is washed with 5% aqueous hydrochloric acid, an aqueous saturated sodium hydrogen carbonate solution and an aqueous saturated sodium chloride solution and then dried over anhydrous sodium sulfate. After distilling off chloroform, the resulting residue is subjected to column chromatography (Wakogel C-200, eluting solvent, benzene:chloroform=4:1, V/V) to isolate N-ethyl-N-cyclohexyl-4-[1-(2-methoxycyclohexyl)-1,2,3,4-tetrazol-5-yl]thio-butyramide (yield: 45%).

Elementary analysis for $C_{20}H_{35}N_5O_2S$: Calcd. (%): C,58.65; H,8.61; N,17.10 Found (%): C,58.25; H,8.34; N,17.20

EXAMPLE 68

4-[1-(4-Ethylphenyl)-1,2,3,4-tetrazol-5-yl]thio-butyric acid (45 mmole) is dissolved in tetrahydrofuran (50 ml), and thereto is added DBU (50 mmole). To the mixture is added dropwise with stirring isobutyl chloroformate (50 mmol) under ice-cooling, and the mixture is stirred at room temperature for 30 minutes. To the mixture is added dropwise N-ethyl-cyclohexylamine (54 mmole), and the mixture is further stirred at room temperature for 2 hours. The solvent is distilled off under reduced pressure and the resulting residue is extracted with chloroform. The chloroform layer is washed with 5% aqueous hydrochloric acid, an aqueous saturated sodium hydrogen carbonate solution and an aqueous saturated sodium chloride solution and then dried over anhydrous sodium sulfate. Chloroform is distilled off and the resulting residue is subjected to column chromatography (Wakogel C-200, eluting solvent, benzene:chloroform=4:1, V/V) to isolate N-ethyl-N-cyclohexyl-4-[1-(4-ethylphenyl)-1,2,3,4-tetrazol-5-yl]thio-butyramide (yield: 43%), colorless liquid, $n_D^{19}=1.5533$.

Elementary analysis for $C_{21}H_{31}N_5OS$: Calcd. (%): C,62.81; H,7.78; N,17.44 Found (%): C,63.05; H,7.84; N,17.81

EXAMPLE 69

5-(1-Phenyl-1,2,3,4-tetrazol-5-yl)valeric acid (2.5 g) is dissolved in dimethylformamide (50 ml), and thereto is added triethylamine (1.1 g). To the mixture is added dropwise with stirring isobutyl chloroformate (1.5 g) under ice-cooling, and the mixture is stirred at room temperature for 30 minutes. To the mixture is added dropwise with stirring diethylamine (0.9 g) at room temperature, and the mixture is stirred for 2 hours. After distilling off dimethylformamide under reduced pressure, acetone is added to the resulting residue, and the insoluble materials are filtered off. The mother liquor is concentrated and then purified by column chromatography (Kieselgel 60, made by Merck & Co.). By eluting with chloroform, there is obtained N,N-diethyl-5-(1-phenyl-1,2,3,4-tetrazol-5-yl)valeramide (1.2 g), colorless liquid, $n_D^{25}=1.5303$.

Elementary analysis for $C_{16}H_{23}N_5O$: Calcd. (%): C,56.40; H,6.63; N,21.92 Found (%): C,56.69; H,6.80; N,21.71

EXAMPLE 70

5-(1-Cyclohexyl-1,2,3,4-tetrazol-5-yl)valeric acid (2.5 g) is dissolved in tetrahydrofuran (50 ml), and thereto is added triethylamine (1.1 g). To the mixture is added dropwise with stirring isobutyl chloroformate (1.5 g) under ice-cooling, and the mixture is stirred at room temperature for 30 minutes. To the mixture is added dropwise with stirring N-ethyl-cyclohexylamine (1.5 g) at room temperature, and the mixture is further stirred for 2 hours. After distilling off tetrahydrofuran, water is added to the residue, and the mixture is extracted with chloroform. The chloroform layer is washed with an aqueous saturated sodium chloride solution and dried over magnesium sulfate. Chloroform is distilled off, and the resulting residue is subjected to column chromatography (Kieselgel 60, made by Merck & Co., eluting solvent, chloroform) to isolate N-ethyl-N-cyclohexyl-5-(1-cyclohexyl-1,2,3,4-tetrazol-5-yl)valeramide (2.6 g), white crystalline powder (ether), m.p. 92°–95° C.

Elementary analysis for $C_{20}H_{35}N_5O$: Calcd. (%): C,66.44; H,9.76; N,19.37 Found (%): C,66.78; H,9.56; N,19.52

EXAMPLE 71

5-(1-Methyl-1,2,3,4-tetrazol-5-yl)valeric acid (1.8 g) is dissolved in dimethylformamide (50 ml), and thereto is added triethylamine (1.1. g). To the mixture is added dropwise with stirring isobutyl chloroformate (1.5 g) under ice-cooling, and the mixture is stirred at room temperature for 30 minutes. To the mixture is added dropwise with stirring diethylamine (0.9 g) at rood temperature, and the mixture is stirred for 2 hours. Dimethylformamide is distilled off under reduced pressure, and the residue is purified by column chromatography (Wakogel C-200). After eluting with benzene-chloroform (1:1), the eluate is distilled under reduced pressure to give N,N-diethyl-5-(1-methyl-1,2,3,4-tetrazol-5-yl)-valeramide (0.7 g), colorless liquid, b.p. 190°–200° C. (bath temperature)/0.07 mmHg, $n_D^{25}=1.4907$.

Elementary analysis for $C_{11}H_{21}N_5O$: Calcd. (%): C,55.20; H,8.85; H,29.27 Found (%): C,55.48; H,8.98; N,29.43

EXAMPLES 72 TO 76

In the same manner as described in Example 71, the following compounds are prepared by using appropriate starting materials.

(72) N,N-Diethyl-5-(1-cyclohexyl-1,2,3,4-tetrazol-5-yl)valeramide, colorless liquid, $n_D^{25}=1.4970$

(73) N,N-Diethyl-5-(1,2,3,4-tetrazol-5-yl)-valeramide, colorless liquid, $n_D^{25}=1.4867$

(74) N-Ethyl-N-cyclohexyl-5-(1-methyl-1,2,3,4-tetrazol-5-yl)valeramide, colorless liquid, $N_D^{18}=1.5085$

(75) N-Ethyl-N-cyclohexyl-5-(1-cyclohexyl-1,2,3,4-tetrazol-5-yl)valeramide, white crystalline powder (ether), m.p. 92°–95° C.

(76) N-Ethyl-N-cyclohexyl-5-(1-phenyl-1,2,3,4-tetrazol-5-yl)valeramide, white prisms (ether), m.p. 73°–75° C.

EXAMPLE 77

3-(1-Methyl-1,2,3,4-tetrazol-5-yl)methylthiopropionic acid (2 g) is dissolved in tetrahydrofuran (50 ml), and thereto is added triethylamine (1.1 g). To the mixture is added dropwise with stirring isobutyl chloroformate (1.5 g) under ice-cooling, and the mixture is stirred at room temperature for 30 minutes. To the mixture is added dropwise with stirring diethylamine (0.9 g) at the same temperature, and the mixture is further stirred for 3 hours. After distilling off the solvent, the resulting residue is subjected to column chromatography (Kieselgel 60, made by Merck & Co., eluting solvent, chloroform:methanol=50:1, V/V) to isolate N,N-diethyl-3-(1-methyl-1,2,3,4-tetrazol-5-yl)methylthio-propionamide (1.5 g), colorless liquid, $n_D^{25}=1.5200$.

Elementary analysis for $C_{10}H_{19}N_5OS$: Calcd. (%): C,46.67; H,7.44; N,27.21 Found (%): C,46.85; H,7.61; N,27.39

EXAMPLES 78 TO 80

In the same manner as described in Example 77, the following compounds are prepared by using appropriate starting materials.

(78) N,N-Diethyl-3-(1-ethyl-1,2,3,4-tetrazol-5-yl)methylthio-propionamide, colorless needles (recrystallized from ether), m.p. 58°–59° C.

(79) N,N-Diethyl-3-[1-(4-ethylphenyl)-1,2,3,4-tetrazol-5-yl)]methylthio-propionamide, colorless liquid, $n_D^{25}=1.5499$

(80) N-Ethyl-N-cyclohexyl-3-(1-ethyl-1,2,3,4-tetrazol-5-yl)methylthio-propionamide, pale yellow liquid, $n_D^{18}=1.5277$

EXAMPLE 81

Thionyl chloride (10 ml) is added to 4-(1-methyl-1,2,3,4-tetrazol-5-yl)thio-butyric acid (2 g) and the mixture is refluxed for 1 hour. After excess thionyl chloride is distilled off under reduced pressure, dry benzene is added to the residue and the remaining small amount of thionyl chloride is removed as the benzene azeotrope. The residue is dissolved in dry benzene (50 ml) and thereto is added dropwise with stirring N-methyl-cyclohexylamine (2.8 g) under ice-cooling. The mixture is stirred at room temperature for 1 hour and benzene is added to the reaction mixture. The mixture is washed with dilute hydrochloric acid, aqueous saturated sodium bicarbonate solution and them, saturated aqueous sodium chloride solution and dried over sodium sulfate. After benzene is distilled off, the residue is subjected to column chromatography (Wakogel C-200) by eluting the column with benzene-chloroform (4:1, V/V) to give N-methyl-N-cyclohexyl-4-(1-methyl-1,2,3,4-tetrazol-5-yl)thio-butyramide (2.3 g), pale yellow liquid.

NMR: $\delta_{ppm}^{CCL_4}$ 1.00–2.00 (10H, br), 1.80–2.70 (4H, m), 2.73 (3H, d, J=6 Hz), 3.28 (2H, t, J=6 Hz), 3.85 (3H, s), 3.20–4.50 (1H, m)

Elementary analysis for $C_{13}H_{23}N_5OS$: Calcd. (%): C,52.50; H,7.79; N,23.55 Found (%): C,52.69; H,7.83; N,23.51

EXAMPLES 82 TO 100

According to the same procedure as described in Example 81, the following compounds are obtained.

(82) N-Ethyl-N-cyclohexyl-4-(1-methyl-1,2,3,4-tetrazol-5-yl)thio-butyramide, colorless liquid, $n_D^{17.5}=1.5327$

(83) N-Ethyl-N-phenyl-4-(1-methyl-1,2,3,4-tetrazol-5-yl)thio-butyramide, pale yellow liquid, $n_D^{26}=1.5534$

(84) 5-(3-Morpholinocarbonylpropylthio)-1-methyl-1,2,3,4-tetrazole, white needles (recrystallized from petroleum ether-ethanol), m.p. 71°–73° C.

(85) 5-[3-(4-Acethylpiperazinocarbonyl)propylthio]-1-methyl-1,2,3,4-tetrazole, white crystalline powder (recrystallized from ligroine-acetone), m.p. 90°–91.5° C.

(86) N-[2-(3,4-Dimethoxyphenylethyl]-4-(1-methyl-1,2,3,4-tetrazol-5-yl)thio-butyramide, colorless flaks (recrystallized from hexane-ethyl acetate), m.p. 70.5°–71.5° C.

(87) N-(2-Hydroxyethyl)-4-(1-methyl-1,2,3,4-tetrazol-5-yl)thio-butyramide, colorless liquid, $n_D^{14.5}=1.5350$

(88) N-Ethyl-N-benzyl-4-(1-methyl-1,2,3,4-tetrazol-5-yl)thio-butyramide, colorless liquid, $n_D^{19}=1.5596$

(89) N-Cyclohexyl-N-[2-(3,4-dimethoxyphenyl)ethyl]-4-(1-methyl-1,2,3,4-tetrazol-5-yl)thio-butyramide, colorless liquid, $n_D^{16}=1.5470$

(90) N-Methyl-N-(2-thienylmethyl)-4-(1-methyl-1,2,3,4-tetrazol-5-yl)thio-butyramide, colorless liquid, $n_D^{16}=1.5706$

(91) N-(2-Pyridyl)-4-(1-methyl-1,2,3,4-tetrazol-5-yl)thio-butyramide, colorless needles (hexane-ethyl acetate), m.p. 95°–96° C.

(92) N-Furfuryl-4-(1-methyl-1,2,3,4-tetrazol-5-yl)thio-butyramide, colorless flaks (hexane-ethyl acetate), m.p. 71°–73° C.

(93) N-[4-(N,N-Dimethylamino)phenyl]-4-(1-methyl-1,2,3,4-tetrazol-5-yl)thio-butyramide, colorless prisms (hexane-ethyl acetate), m.p. 144°–147° C.

(94) N-(2-Methyl-3-chlorophenyl)-4-(1-methyl-1,2,3,4-tetrazol-5-yl)thio-butyramide, colorless needles (hexane-ethyl acetate), m.p. 104.5°–105.5° C.

(95) N-Methyl-N-(2-tetrahydropyranyl)-4-(1-methyl-1,2,3,4-tetrazol-5-yl)thio-butyramide, colorless liquid, $n_D^{14}=1.5273$

(96) N-Ethyl-N-cyclohexylmethyl-4-(1-methyl-1,2,3,4-tetrazol-5-yl)thio-butyramide, colorless liquid, $n_D^{11}=1.5293$

(97) N-Ethyl-N-(4-hydroxycyclohexyl)-4-(1-methyl-1,2,3,4-tetrazol-5-yl)thio-butylamide, colorless liquid, $n_D^9=1.5363$

(98) N-Ethyl-N-(2-acetyloxycyclohexyl)-4-(1-methyl-1,2,3,4-tetrazol-5-yl)thio-butyramide, colorless liquid, $n_D^{11}=1.5218$

(99) 5-(3-Piperidinocarbonylpropylthio)-1-methyl-1,2,3,4-tetrazole, colorless liquid, $n_D^{25}=1.5310$ (100) N-Ethyl-N-cyclohexyl-4-(1-phenyl-1,2,3,4-tetrazol-5-yl)thio-butyramide, colorless liquid, $n_D^{18}=1.5590$

EXAMPLE 101

Thionyl chloride (10 ml) is added to 5-(1-phenyl-1,2,3,4-tetrazol-5-yl)valeric acid (1.8 g) and the mixture is refluxed for 1 hour. After excess thionyl chloride is distilled off under reduced pressure, dry benzene is added to the residue and the remaining small amount of thionyl chloride is removed as the benzene azeotrope. The resulting residue is dissolved in dry pyridine (50 ml)

and thereto is added dropwise with stirring N,N-Diethylamine (1.5 g) under ice-cooling. The mixture is stirred at room temperature for 1 hour and benzene is added to the reaction mixture. The mixture is washed with diluted hydrochloric acid, aqueous saturated sodium bicarbonate solution and aqueous saturated sodium chloride solution and dried over sodium sulfate. After benzene is distilled off, the residue is subjected to column chromatography (Kieselgel 60 produced by Merck) by eluting the column with chloroform to give N,N-di-ethyl-5-(1-phenyl-1,2,3,4-tetrazol-5-yl)valeramide (2.1 g), colorless liquid, $n_D^{25} = 1.5303$.

Elementary analysis for $C_{16}H_{23}N_5O$: Calcd. (%): C,63.76; H,7.69; N,23.24 Found (%): C,63.88; H,7.79; N,23.31

EXAMPLES 102 TO 104

According to the same procedure as described in Example 101, the following compounds are obtained.

(102) N-Ethyl-N-cyclohexyl-5-(1-cyclohexyl-1,2,3,4-tetrazol-5-yl)valeramide, white crystalline powder (recrystallized from ether), m.p. 92°-95° C.

(103) N-Ethyl-N-cyclohexyl-5-(1-methyl-1,2,3,4-tetrazol-5-yl)valeramide, colorless liquid, $n_D^{18} = 1.5085$ (104) N-Ethyl-N-cyclohexyl-5-(1-phenyl-1,2,3,4-tetrazol-5-yl)valeramide, white prisms (ether), m.p. 73°-75° C.

EXAMPLE 105

1-Methyl-5-mercapto-1,2,3,4-tetrazole (11.6 g) is dissolved in acetone (100 ml) and thereto are added methyl 4-bromobutyrate (21.7 g) and potassium carbonate (15 g). The mixture is refluxed for 4 hours. After acetone is distilled off under reduced pressure, water is added to the resulting residue and the aqueous mixture is extracted with chloroform. The chloroform solution is washed with aqueous saturated sodium chloride solution and dried over magnesium sulfate. After chloroform is distilled off, the residue is subjected to column chromatography (Wakogel C-200) by eluting the column with benzene-ether (5:1, V/V). The eluate is distilled under reduced pressure to give methyl 4-(1-methyl-1,2,3,4-tetrazol-5-yl)thio-butyrate (20 g), colorless liquid, b.p. 175°-177° C./0.8 mmHg, $n_D^{26} = 1.5083$.

Elementary analysis for $C_7H_{12}N_4OS$: Calcd.(%): C,38,88; H,5.59; N,25.91 Found (%): C,38.98; H,5.67; N,25.83

EXAMPLES 106 AND 107

Substitution of 1-phenyl- or 1-cyclohexyl-5-mercapto-1,2,3,4-tetrazole for 1-methyl-5-mercapto-1,2,3,4-tetrazole in the procedure of Example 105 produces the following compounds.

(106) Methyl 4-(1-phenyl-1,2,3,4-tetrazol-5-yl)thio-butyrate, colorless liquid, $n_D^{18} = 1.5654$ (107) Methyl 4-(1-cyclohexyl-1,2,3,4-tetrazol-5-yl)thio-butyrate, pale yellow liquid, $n_D^{18} = 1.5162$

EXAMPLE 108

3-Mercaptopropionic acid (1.6 g) is dissolved in 1N aqueous sodium hydroxide solution (45 ml) and thereto is added dropwise a solution of 1-methyl-5-chloromethyl-1,2,3,4-tetrazole (15.2 g) in acetone (20 ml) with stirring under ice-cooling. Stirring is continued for 3 hours under ice-cooling. Acetone is distilled off and the residue is acidified with concentrated hydrochloric acid, saturated with sodium chloride and then, extracted with chloroform. The chloroform solution is dried over magnesium sulfate. After chloroform is distilled off, the residue is subjected to column chromatography (Kieselgel 60, made by Merck) by eluting the column with chloroform-methanol (10:1, V/V) to give 3-(1-methyl-1,2,3,4-tetrazol-5-yl)methylthio-propionic acid (2.1 g) as a colorless liquid.

MNR $\delta_{ppm}^{CDCl_3}$ 2.40-3.00 (4H, m), 4.05 (2H, s), 4.12 (3H, s), 9.79 (1H, s)

Elementary analysis for $C_6H_{10}N_4O_2S$: Calcd. (%): C,35.63; H,4.98; N,27.70 Found (%): C,35.81; H,4.83; N,27.83

EXAMPLES 109 AND 110

According to the same procedure as described in Example 108, the following compounds are obtained by using appropriate starting materials.

(109) 3-(1-Ethyl-1,2,3,4-tetrazol-5-yl)methyl-thio-propionic acid, colorless prisms (acetone-ether), m.p. 68°-70° C.

(110) 3-[1-(4-Ethylphenyl)-1,2,3,4-tetrazol-5-yl]methylthio-propionic acid, colorless liquid, NMR: $\delta_{ppm}^{CDCl_3}$ 1.28 (3H, t, J=7 Hz), 2.40-3.10 (6H, m), 3.97 (2H, s), 7.43 (4H, br.s), 10.02 (1H, br.s)

EXAMPLE 111

Methyl N-phenyladipinamate (9 g) is dissolved in benzene (70 ml) and thereto is added phosphorous pentachloride (9 g) with stirring at below 15° C. The mixture is stirred at room temperature for 1.5 hours and concentrated to 1/3 by volume under reduced pressure. A solution of hydrogen azide in benzene (0.0172 mol/10 ml, 44.2 ml) is added dropwise to the resulting iminochloride solution with stirriing under ice-cooling. The mixture is stirred at room temperature for 1 hour, allowed to stand overnight and thereafter gently refluxed for 2 hours. The reaction mixture is concentrated, and thereto is added ice-water (50 ml) and the mixture is extracted with chloroform. The chloroform solution is washed with water, aqueous dilute sodium hydroxide solution and water and then dried over magnesium sulfate. Chloroform is distilled off and the residue is subjected to column chromatography (Wakogel C-200) by eluting the column with benzene-ether (5:1, V/V) to give methyl 5-(1-phenyl-1,2,3,4-tetrazol-5-yl)-valerate (7.3 g) as a colorless liquid.

NMR: $\delta_{ppm}^{CDCl_3}$ 1.50-2.10 (4H, m), 2.30 (2H, t, J=6 Hz), 2.90 (2H, t, J=6 Hz), 3.62 (3H, s), 7.30-7.70 (5H, m)

Elementary analysis for $c_{13}H_{16}N_4O_2$: Calcd (%): C,59.98; H,6.20; N,21.53 Found (%): C,60.19; H,6.32; N,21.71

EXAMPLES 112 TO 114

According to the same procedure as described in Example 111, the following compounds are obtained by using appropriate staring materials.

(112) Methyl 5-(1-methyl-1,2,3,4-tetrazol-5-yl)valerate, colorless liquid, NMR: $\delta_{ppm}^{CDCl_3}$ 1.50-2.20 (4H, m), 2.36 (2H, t, J=6 Hz), 2.90 (2H, t, J=6 Hz), 3.65 (3H, s), 4.05 (3H, s)

(113) Methyl 5-(1-cyclohexyl-1,2,3,4-tetrazol-5-yl)valerate, colorless liquid, NMR: $\delta_{ppm}^{CDCl_3}$ 1.00-2.20 (14H, m), 2.38 (2H, t, J=6 Hz), 2.90 (2H, t, J=6 Hz), 3.70 (3H, s), 3.90-4.50 (1H, m)

(114) Methyl 5-(1,2,3,4-tetrazol-5-yl)valerate, colorless liquid, NMR: $\delta_{ppm}^{CDCl_3}$ 1.50-2.20 (4H, m), 2.34 (2H, t, J=6 Hz), 3.02 (2H, t, J=6 Hz), 3.60 (3H, s)

EXAMPLE 115

20 % aqueous Hydrochloric acid (100 ml) is added to methyl 5-(1-phenyl-1,2,3,4-tetrazol-5-yl)valerate (9.3 g) and the mixture is refluxed for 4 hours. After cooling, water is added and the mixture is extracted with chloroform. The chloroform solution is extracted with aqueous saturated sodium bicarbonate solution. The aqueous layer is acidified with concentrated hydrochloric acid and again extracted with chloroform. The latter chloroform extract is washed with aqueous saturated sodium chloride solution and dried over magnesium sulfate. Chloroform is distilled off to give 5-(1-phenyl-1,2,3,4-tetrazol-5-yl)valeric acid (8.2 g), pale yellow liquid.

NMR: $\delta_{ppm}^{CDCl_3}$ 1.40–2.10 (4H, m), 2.33 (2H, t, J=6 Hz), 2.92 (2H, t, J=6 Hz), 7.30–7.70 (5H, m), 10.56 (1H, s)

Elementary analysis for $C_{12}H_{14}N_4O_2$: Calcd. (%): C,58.52; H,5.73; N,22.75 Found (%): C,58.61; H,5.85; N,22.88

EXAMPLES 116 TO 118

According to the same procedure as described in Example 115, the following compounds are obtained by using the compounds of Examples 200 to 202 as the starting material.

(116) 5-(1-Methyl-1,2,3,4-tetrazol-5-yl)valeric acid, colorless prisms (ether-ethanol), m.p. 107°–109° C., NMR: $\delta_{ppm}^{CDCl_3}$ 1.40–2.20 (4H, m), 2.28 (2H, t, J=2.87 (2H, t, J=6 Hz), 4.02 (3H, s), 9.30 (1H, br.s)

(117) 5-(1-Cyclohexyl-1,2,3,4-tetrazol-5-yl)valeric acid, colorless prisms (recrystallized from ethanol-water), m.p. 100°–102° C.

(118) 5-(1,2,3,4-Tetrazol-5-yl)valeric acid, colorless liquid, NMR: $\delta_{ppm}^{d6-DMSO}$ 1.30–2.00 (4H, m), 2.30 (2H, t, J=6 Hz), 2.87 (2H, t, J=6 Hz).

EXAMPLE 119

20% aqueous Hydrochloric acid (150 ml) is added to methyl 4-(1-methyl-1,2,3,4-tetrazol-5-yl)thio-valerate (17 g) and the mixture is refluxed for 2 hours. After cooling, the reaction mixture is diluted with water and extracted with chloroform. The chloroform solution is washed with aqueous saturated sodium chloride solution and dried over magnesium sulfate. Chloroform is distilled off to give 4-(1-methyl-1,2,3,4-tetrazol-5-yl)thio-valeric acid, colorless liquid, $n_D^{26}$=1.5133.

NMR: $\delta_{ppm}^{CDCl_3}$ 1.80–2.80 (6H, m), 3.42 (2H, t, J=7 Hz), 3.96 (3H, s), 11.18 (1H, s)

Elementary analysis for $C_6H_{10}N_4O_2S$: Calcd. (%): C,35.63; H,4.98; N,27.70 Found (%): C,35.76; H,5.11; N,27.81

EXAMPLES 120 AND 121

Substitution of methyl 4-(1-phenyl- or cyclohexyl-1,2,3,4-tetrazol-5-yl)thio-valerate for methyl 4-(1-methyl-1,2,3,4-tetrazol-5-yl)thio-valerate in the procedure of Example 119 produces the following compounds.

(120) 4-(1-Phenyl-1,2,3,4-tetrazol-5-yl)thio-valeric acid, pale yellow liquid, NMR: $\delta_{ppm}^{CDCl_3}$ 2.00–2.70 (4H, m), 3.44 (2H, t, J=7 Hz), 7.55 (5H, s), 10.98 (1H, br.s)

(121) 4-(1-Cyclohexyl-1,2,3,4-tetrazol-5-yl)thio-valeric acid, colorless prisms (ether), m.p. 67.5°–69.5° C.

EXAMPLE 122

In the same manner as described in Example 63, there is obtained N,N-diethyl-4-(1-cyclohexyl-1,2,3,4-tetrazol-5-yl)thio-butyramide, colorless liquid, $n_D^{20}$=1.5237.

EXAMPLE 123

In the same manner as described in Example 105, there is obtained methyl 4-[1-(4-ethylphenyl)-1,2,3,4-tetrazol-5-yl]thio-butyrate, pale yellow liquid, $n_D^{14}$=1.5581.

EXAMPLE 124

In the same manner as described in Example 119, there is obtained 4-[1-(4-ethylphenyl)-1,2,3,4-tetrazol-5-yl)thio-butyric acid, pale yellow liquid, NMR: $\delta_{ppm}^{CDCl_3}$ 1.28 (3H, t, J=7.5 Hz), 2.00–2.90 (6H, m), 3.44 (2H, t, J=7 Hz), 7.36 (2H, d, J=9 Hz), 7.48 (2H, d, J=9 Hz), 10.60 (1H, br.s).

EXAMPLES 125 TO 130

According to the same procedure as described in Example 71, the following compounds are obtained.

(125) N-Hexyl-5-(1-phenyl-1,2,3,4-tetrazol-5-yl)valeramide, colorless needles (ethyl acetate-hexane), m.p. 80.5°–82.5° C.

(126) N-Isopropyl-N-cyclohexyl-5-(1-phenyl-1,2,3,4-tetrazol-5-yl)valeramide, colorless needles (ether), m.p. 91°–92.5° C.

(127) N-Ethyl-N-cyclohexyl-4-(1-phenyl-1,2,3,4-tetrazol-5-yl)butyramide, colorless needles (ether), m.p. 77.5°–80° C.

(128) N-Butyl-4-(1-phenyl-1,2,3,4-tetrazol-5-yl)butyramide, colorless needles (ethyl acetate-hexane), m.p. 76.5°–78.5° C.

(129) N-Cyclohexyl-5-(1-phenyl-1,2,3,4-tetrazol-5-yl)valeramide, colorless needles (ethyl acetate-hexane), m.p. 100°–102° C.

(130) N-Methyl-N-cyclohexyl-5-(1-phenyl-1,2,3,4-tetrazol-5-yl)valeramide, colorless oily substance, $n_D^{21}$=1.5396

EXAMPLES 131–179

According to the same procedure as described in Examples 6 and 81, the following compounds are obtained (131) N-Ethyl-3-(1-methyl-1,2,3,4-tetrazol-5-yl)methylthio-propionamide, colorless flakes (hexane-ethyl acetate), m.p. 61.5°–62.5° C.

(132) N-Ethyl-3-(1-ethyl-1,2,3,4-tetrazol-5-yl)methylthio-propionamide, pale yellow liquid, $n_D^{27}$=1.5253

(133) N-Ethyl-3-(1-isopropyl-1,2,3,4-tetrazol-5-yl)methylthio-propionamide, colorless liquid, $n_D^{22}$=1.5179

(134) N-Ethyl-3-(1-butyl-1,2,3,4-tetrazol-5-yl)methylthio-propionamide, pale yellow liquid, $n_D^{18}$=1.5149

(135) N-Ethyl-3-(1-cyclohexyl-1,2,3,4-tetrazol-5-yl)methylthio-propionamide, colorless needles (hexane-ethyl acetate), m.p. 131°–132° C.

(136) N-Ethyl-3-(1-phenyl-1,2,3,4-tetrazol-5-yl)methylthio-propionamide, colorless needles (hexane-ethyl acetate), m.p. 88°–89.5° C.

(137) N-Ethyl-3-[1-(4-ethylphenyl)-1,2,3,4-tetrazol-5-yl]methylthio-propionamide, colorless needles (hexane-ethyl acetate), m.p. 88°–89.5° C.

(138) N,N-Diethyl-3-(1-butyl-1,2,3,4-tetrazol-5-yl)methylthio-propionamide, reddish brown liquid, $n_D^{26}$=1.5107

(139) N,N-Diethyl-3-(1-phenyl-1,2,3,4-tetrazol-5-yl)methylthio-propionamide, yellowish brown liquid, $n_D^{26}$=1.5625

(140) N-Ethyl-4-(1-ethyl-1,2,3,4-tetrazol-5-yl)methylthio-butyramide, pale yellow liquid, $n_D^{26}=1.5224$ (141) N-Ethyl-2-(1-ethyl-1,2,3,4-tetrazol-5-yl)methylthio-acetamide, pale yellow liquid, $n_D^{22}=1.5305$ (142) N-Ethyl-2-(1-ethyl-1,2,3,4-tetrazol-5-yl)ethylthio-acetamide, pale yellow liquid, $n_D^{22}=1.5274$ (143) N-Ethyl-2-(1-ethyl-1,2,3,4-tetrazol-5-yl)propylthio-acetamide, pale yellow liquid, $n_D^{23}=1.5210$ (144) N,N-Diethyl-4-(1-ethyl-1,2,3,4-tetrazol-5-yl)methylthio-butyramide, pale yellow liquid, $n_D^{25}=1.5128$ (145) N-Methyl-3-(1-ethyl-1,2,3,4-tetrazol-5-yl)methylthio-propionamide, colorless liquid, $n_D^{24}=1.5320$ (146) N-Butyl-3-(1-ethyl-1,2,3,4-tetrazol-5-yl)methylthio-propionamide, pale yellow liquid, $n_D^{21}=1.5111$ (147) N-Methyl-N-(2-thienylmethyl)-3-(1-ethyl-1,2,3,4-tetrazol-5-yl)methylthio-propionamide, colorless liquid, $n_D^{27}=1.5697$ (148) N-(2-Thiazolyl)-3-(1-ethyl-1,2,3,4-tetrazol-5-yl)methylthio-propionamide, pale yellow prisms (hexane-ethyl acetate), m.p. 113°–114° C.

(149) N,N-Diethyl-4-(1-phenyl-1,2,3,4-tetrazol-5-yl)thio-butyramide, colorless liquid, $n_D^{18}=1.5592$ (150) N,N-Diethyl-4-(1-cyclohexyl-1,2,3,4-tetrazol-5-yl)thio-butyramide, colorless liquid, $n_D^{20}=1.5237$ (151) N-Pentyl-4-(1-methyl-1,2,3,4-tetrazol-5-yl)thio-butyramide, colorless crystal (hexane-ether), m.p. 67.5°–68.5° C.

(152) N-(4-Methoxyphenyl)-5-(1-phenyl-1,2,3,4-tetrazol-5-yl)valeramide, colorless crystal (ethanol), m.p. 148°–150.5° C.

(153) N-Butyl-5-(1-phenyl-1,2,3,4-tetrazol-5-yl)valeramide, colorless crystal (ethyl acetate-hexane), m.p. 71°–73° C.

(154) N-(2-Thiazolyl)-4-(1-methyl-1,2,3,4-tetrazol-5-yl)thio-butyramide, colorless crystal (methanol), m.p. 175°–176.5° C.

(155) N-(4-Methoxyphenyl)-4-(1-methyl-1,2,3,4-tetrazol-5-yl)thio-butyramide, colorless crystal (hexane-ethyl acetate), m.p. 122.5°–124° C.

(156) N-(3-Methoxyphenyl)-4-(1-methyl-1,2,3,4-tetrazol-5-yl)thio-butyramide, colorless crystal (hexane-ethyl acetate), m.p. 122.5°–124° C.

(157) N-(1-Methylpropyl)-4-(1-methyl-1,2,3,4-tetrazol-5-yl)thio-butyramide, colorless liquid, $n_D^{20}=1.5066$ (158) N-Butyl-4-(1-phenyl-1,2,3,4-tetrazol-5-yl)thio-butyramide, colorless liquid, $n_D^{22.5}=1.5590$ (159) N-Butyl-3-(1-methyl-1,2,3,4-tetrazol-5-yl)thio-propionamide, colorless crystal (ethyl acetate-hexane), m.p. 80.5°–82.5° C.

(160) N-Butyl-5-(1-methyl-1,2,3,4-tetrazol-5-yl)thio-valeramide, colorless crystal (ether), m.p. 53.5°–55° C.

(161) N-Ethyl-N-cyclohexyl-5-[1-(4-methoxyphenyl)-1,2,3,4-tetrazol-5-yl]valeramide, colorless liquid, $n_D^{16}=1.5343$ (162) N-Ethyl-N-phenyl-5-(1-phenyl-1,2,3,4-tetrazol-5-yl)valeramide, colorless liquid, $n_D^{16}=1.5640$ (163) N-Ethyl-N-cyclohexyl-5-[1-(4-acetyloxyphenyl)-1,2,3,4-tetrazol-5-yl]valeramide, white powdery crystal (ethyl acetate-hexane), m.p. 88°–90° C.

(164) N-Ethyl-N-cyclohexyl-5-[1-(4-hydroxyphenyl)-1,2,3,4-tetrazol-5-yl]valeramide, colorless granules (ethanol), m.p. 181.5°–183° C.

(165) N-Ethyl-N-cyclohexyl-5-[1-(4-ethylphenyl)-1,2,3,4-tetrazol-5-yl]valeramide, colorless needles (ethyl acetate-hexane), m.p. 54°–55.5° C.

(166) N-Ethyl-N-cyclohexyl-5-(1-butyl-1,2,3,4-tetrazol-5-yl)valeramide, colorless liquid, $n_D^{20.5}=1.5013$ (167) 5-[3-(4-Methylpiperazinylcarbonyl)propyl]-1-phenyl-1,2,3,4-tetrazole, pale yellow needles (ethyl acetate-hexane), m.p. 62°–64° C.

(168) N-Ethyl-N-cyclohexyl-3-(1-phenyl-1,2,3,4-tetrazol-5-yl)propionamide, colorless prisms (ethanol), m.p. 137°–138° C.

(169) 5-[4-(4-Methylpiperazinylcarbonyl)butyl]-1-phenyl-1,2,3,4-tetrazole, pale yellow liquid, $n_D^{15.5}=1.5543$ (170) N-(4-Methoxycyclohexyl)-5-(1-phenyl-1,2,3,4-tetrazol-5-yl)valeramide, colorless needles (hexane-ethyl acetate), m.p. 89°–90.5° C.

(171) N-Ethyl-N-(2-hydroxycyclohexyl)-5-(1-phenyl-1,2,3,4-tetrazol-5-yl)valeramide, colorless liquid, $n_D^{16}=1.5501$ (172) N,N-Dipropyl-5-(1-phenyl-1,2,3,4-tetrazol-5-yl)valeramide, colorless liquid, $n_D^{15.5}=1.5311$ (173) N-Methyl-N-(2-furylmethyl)-5-(1-phenyl-1,2,3,4-tetrazol-5-yl)valeramide, colorless liquid, $n_D^{16.5}=1.5490$ (174) N-Ethyl-N-cyclooctyl-5-(1-phenyl-1,2,3,4-tetrazol-5-yl)valeramide, colorless liquid, $n_D^{16.5}=1.5418$ (175) N-Ethyl-N-(4-hydroxycyclohexyl)-5-(1-phenyl-1,2,3,4-tetrazol-5-yl)valeramide, colorless liquid, $n_D^{15.5}=1.5505$ (176) N-Ethyl-N-cyclopentyl-5-(1-phenyl-1,2,3,4-tetrazol-5-yl)valeramide, colorless liquid, $n_D^{20}=1.5446$ (177) N-(2-Thiazolyl)-5-(1-phenyl-1,2,3,4-tetrazol-5-yl)valeramide, colorless needles (ethanol), m.p. 166°–168° C.

(178) N-Ethyl-5-(1-phenyl-1,2,3,4-tetrazol-5-yl)valeramide, colorless flakes (ethyl acetate-hexane), m.p 60°–61.5° C.

(179) N,N-Diethyl-3-(1-phenyl-1,2,3,4-tetrazol-5-yl)methylthio-propionamide, yellowish brown liquid, $n_D^{26}=1.5625$

EXAMPLES 180–185

According to the same procedure as described in Example 108, the following compounds are obtained.

(180) 3-(1-Methyl-1,2,3,4-tetrazol-5-yl)methylthio-propionic acid, colorless prisms (hexane-ethyl acetate), m.p. 80.5°–82.5° C.

(181) 3-(1-Isopropyl-1,2,3,4-tetrazol-5-yl)methylthio-propionic acid, colorless prisms (hexane-ethyl acetate), m.p. 56°–59° C.

(182) 3-(1-Butyl-1,2,3,4-tetrazol-5-yl)methylthio-propionic acid, pale yellow prisms (ether-hexane), m.p. 33°–35° C.

(183) 3-(1-Cyclohexyl-1,2,3,4-tetrazol-5-yl)methylthio-propionic acid, colorless needles (ethyl acetate), m.p. 108°–110° C.

(184) 3-(1-Phenyl-1,2,3,4-tetrazol-5-yl)methylthio-propionic acid, colorless prisms (hexane-ethyl acetate), m.p. 102°–103° C.

(185) 3-(1-Ethyl-1,2,3,4-tetrazol-5-yl)methylthio-propionic acid, colorless prisms (acetone-ether), m.p. 68°–70° C.

EXAMPLE 186

According to the same procedure as described in Example 105, the following compound is obtained.

Methyl 4-[1-(4-ethylphenyl)-1,2,3,4-tetrazol-5-yl]thio-butyrate, colorless liquid, $n_D^{14}=1.5581$

EXAMPLES 187-192

According to the same procedure as described in Example 115, the following compounds are obtained.

(187) 5-[1-(4-Methoxyphenyl)-1,2,3,4-tetrazol-5-yl]valeric acid, colorless needles (ethanol-water), m.p. 105°-107° C.

(188) 5-(1-Butyl-1,2,3,4-tetrazol-5-yl)valeric acid, colorless prisms (ether), m.p. 66.5°-68° C.

(189) 4-(1-Phenyl-1,2,3,4-tetrazol-5-yl)butyric acid, colorless prisms (ethanol-water), m.p. 82.5°-84.5° C.

(190) 5-[1-(4-Acetyloxyphenyl)-1,2,3,4-tetrazol-5-yl]valeric acid, colorless flakes (ethanol), m.p. 109°-110° C.

(191) 3-(1-Phenyl-1,2,3,4-tetrazol-5-yl)propionic acid, colorless needles (ethyl acetate), m.p. 120°-122.5° C.

(192) 5-[1-(2-Hydroxyphenyl)-1,2,3,4-tetrazol-5-yl]valeric acid, pale brown prisms (acetone-water), m.p. 180°-183° C.

EXAMPLE 193

To 3-(1-ethyl-1,2,3,4-tetrazol-5-yl)methylthio-propionic acid (20 g) is added thionyl chloride (30 ml), and the mixture is stirred at 50 ° C. for 30 minutes. Excess amount of thionyl chloride is distilled off and further it is completely removed by azeotropic distillation with benzene.

Separately, 25% aqueous ammonia (20 ml) and potassium carbonate (12.8 g) are dissolved in acetone-water (150 ml-30 ml ). To the solution is added dropwise a solution of the acid chloride obtained above in acetone (30 ml) with stirring under ice-cooling, and the mixture is stirred for 2 hours. After acetone is distilled off, the aqueous phase is saturated with sodium chloride and then is extracted with chloroform. The chloroform solution is dried over magnesium sulfate and concentrated under reduced pressure. The resulting residue is recrystallized from ethyl acetate to give 3-(1-ethyl-1,2,3,4-tetrazol-5-yl)methylthio-propionamide (9.2 g) as colorless flakes. m.p. 74°-76° C.

EXAMPLE 194

In the same manner as described in Example 193, 3-(1-phenyl-1,2,3,4-tetrazol-5-yl)methylthio-propionamide is obtained as colorless prisms (recrystallized from ethyl acetate). m.p. 91°-92° C.

EXAMPLE 195

In the same manner as described in Example 71, N-cyclohexyl-N-(2-hydroxyethyl)-5-(1-phenyl-1,2,3,4-tetrazol-5-yl)valeramide as colorless liquid. $n_D^{16.5} = 1.5470$

| Preparation 1 | |
|---|---|
| Ingredients | Amounts |
| N—Ethyl-N—(2-hydroxycyclohexyl)-4-(1-methyl-1,2,3,4-tetrazol-5-yl)thio-butyramide | 150 g |
| Avicel (trade mark of microcrystalline cellulose produced by Asahi-kasei Co., Ltd.) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

The compound of the present invention, Avicel, corn starch and magnesium stearate are mixed, ground and then, compressed into tablets with a punch having a diameter of 10 mm. The tablets thus obtained are coated with the film coating solution consisting of hydroxypropylmethyl cellulose, polyethylene glycol-6000, castor oil and methanol to obtain film coated tablets.

| Preparation 2 | |
|---|---|
| Ingredients | Amounts |
| N—(2-Pyridyl)-4-(1-methyl-1,2,3,4-tetrazol-5-yl)thio-butyramide | 150 g |
| Citric acid | 1 g |
| Lactose | 33.5 g |
| Dipotassium hydrogen phosphate | 70 g |
| Pluronic F-68 | 30 g |
| Sodium lauryl sulfate | 15 g |
| Polyvinyl pyrrolidone | 15 g |
| Polyethylene glycol (Carbowax 1500) | 4.5 g |
| Polyethylene glycol (Carbowax 6000) | 45 g |
| Corn starch | 30 g |
| Dry sodium lauryl sulfate | 3 g |
| Dry magnesium stearate | 3 g |
| Ethanol | appropriate amount |

The compound of the present invention, citric acid, lactose, dipotassium hydrogen phosphate, Pluronic F-68 and sodium lauryl sulfate are mixed and passed through No. 60 screen. The resulting mixture is granulated with an alcoholic solution containing polyvinyl pyrrolidone, Carbowax 1500 and Carbowax 6000. The powdery mixture is made into paste by adding alcohol, if necessary. Corn starch is added to the wet mass and mixing is continued until uniform granules are formed. The wet granules are passed through No. 10 screen, placed in a try and dried in an oven at 100° C. for 12-14 hours. The dried granules are passed through No. 16 screen, mixed with dry sodium lauryl sulfate and dry magnesium stearate and then, compressed into a desired shape.

The core tablets thus obtained are treated with varnish and thereto is spreaded talc in order to prevent absorption of moisture. Subcoating is applied about the resulting tablets. The tablets are again treated enough times with varnish for oral administration. Further, subcoating and smooth layers are applied about the tablets so as to make them round and smooth. Coloring layer is applied so as to be the tablets in desired color. After drying, polishing produces the tablets having homogeneous gloss.

| Preparation 3 | |
|---|---|
| Ingredients | Amounts |
| N—Ethyl-N—cyclohexyl-4-(1-methyl-1,2,3,4-tetrazol-5-yl)thio-butyramide | 5 g |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved in an about half amount of the distilled water with stirring at 80° C. The resulting solution is cooled to 40° C. and the above compound of the present invention, polyethylene glycol and polyoxyethylene sorbitan monooleate are dissolved in the solution. The remaining distilled water is added to the solution to adjust the volume. The solution is sterilized by filtration with a suitable filter paper to obtain a preparation for injection.

Pharmacological tests

The pharmacological activities of the compounds [I] of the present invention were tested by conventional methods as mentioned hereinafter with respect to the following compounds:

1. N,N-Diethyl-4-(1-methyl-1,2,3,4-tetrazol-5-yl)thio-butyramide
2. N-Ethyl-N-cyclohexyl-4-(1-methyl-1,2,3,4-tetrazol-5-yl)thio-butyramide
3. N-Ethyl-N-cyclohexyl-5-(1-methyl-1,2,3,4-tetrazol-5-yl)thio-valeramide
4. N-Ethyl-N-cyclohexyl-5-(1-phenyl-1,2,3,4-tetrazol-5-yl)valeramide
5. N,N-Diethyl-5-(1-cyclohexyl-1,2,3,4-tetrazol-5-yl)valeramide
6. N-Cyclohexyl-4-(1-methyl-1,2,3,4-tetrazol-5-yl)thio-butyramide
7. N-[4-(N,N-dimethylamino)phenyl]-4-(1-methyl-1,2,3,4-tetrazol-5-yl)thio-butyramide
8. N-Ethyl-N-(2-hydroxycyclohexyl)-4-(1-methyl-1,2,3,4-tetrazol-5-yl)thio-butyramide
9. N-Ethyl-N-phenyl-4-(1-methyl-1,2,3,4-tetrazol-5-yl)thio-butyramide
10. N-Ethyl-N-(2-pyridyl)-4-(1-methyl-1,2,3,4-tetrazol-5-yl)thio-butyramide
11. N-Cyclohexyl-N-[2-(3,4,-dimethoxyphenyl)ethyl]-4-(1-methyl-1,2,3,4-tetrazol-5-yl)thio-butyramide
12. N,N-Diethyl-3-[1-(4-ethylphenyl)-1,2,3,4-tetrazol-5-yl]methylthio-propionamide
13. N-Furfuryl-4-(1-methyl-1,2,3,4-tetrazol-5-yl)thio-butyramide
14. N,N-Diethyl-3-(1-ethyl-1,2,3,4-tetrazol-5-yl)methylthio-propionamide
15. N-Ethyl-3-(1-butyl-1,2,3,4-tetrazol-5-yl)methylthio-propionamide
16. N-Ethyl-3-(1-phenyl-1,2,3,4-tetrazol-5-yl)methylthio-propionamide
17. N-Ethyl-4-(1-ethyl-1,2,3,4-tetrazol-5-yl)methylthio-butyramide
18. N,N-Diethyl-4-(1-ethyl-1,2,3,4-tetrazol-5-yl)methylthio-butyramide
19. 3-(1-Ethyl-1,2,3,4-tetrazol-5-yl)methylthio-propionamide
20. N-Ethyl-N-cycloheptyl-4-(1-methyl-1,2,3,4-tetrazol-5-yl)thio-butyramide
21. N,N-Diisopropyl-4-(1-methyl-1,2,3,4-tetrazol-5-yl)thio-butyramide
22. N,N,-Dibenzyl-4-(1-methyl-1,2,3,4-tetrazol-5-yl)thio-butyramide
23. N-Ethyl-N-cyclohexyl-5-(1-cyclohexyl-1,2,3,4-tetrazol-5-yl)valeramide
24. N-Isopropyl-N-cyclohexyl-4-(1-methyl-1,2,3,4-tetrazol-5-yl)thio-butyramide
25. 1-Methyl-5-(3-piperidylcarbonylpropyl)thio-1,2,3,4-tetrazole
26. N-[2-(3,4-Dimethoxyphenyl)ethyl]-4-(1-methyl-1,2,3,4-tetrazol-5-yl)thio-butyramide
27. N-(2-Pyridyl)-4-(1-methyl-1,2,3,4-tetrazol-5-yl)thio-butyramide
28. N,N-Dimethyl-4-(1-methyl-1,2,3,4-tetrazol-5-yl)thio-butyramide
29. N-Ethyl-N-cyclopentyl-4-(1-methyl-1,2,3,4-tetrazol-5-yl)thio-butyramide
30. N-Ethyl-N-cyclohexylmethyl-4-(1-methyl-1,2,3,4-tetrazol-5-yl)thio-butyramide
31. N-Ethyl-N-cyclohexyl-4-(1-phenyl-1,2,3,4-tetrazol-5-yl)thio-butyramide
32. 1-Methyl-5-[3-(4-acetyl-1-piperazinylcarbonyl)-propyl]thio-1,2,3,4-tetrazole
33. 1-Methyl-5-(3-morpholinocarbonylpropyl)thio-1,2,3,4-tetrazole
34. N,N-Diethyl-5-(1-methyl-1,2,3,4-tetrazol-5-yl)valeramide
35. N,N-Diethyl-5-(1-phenyl-1,2,3,4-tetrazol-5-yl)valeramide
36. N-Ethyl-N-cyclohexyl-3-(1-ethyl-1,2,3,4-tetrazol-5-yl)methylthio-propionamide
37. Methyl 4-(1-methyl-1,2,3,4-tetrazol-5-yl)thio-butyrate
38. 4-(1-methyl-1,2,3,4-tetrazol-5-yl)thio-butyric acid
39. N-Methyl-N-(2-thienylmethyl)-4-(1-methyl-1,2,3,4-tetrazol-5-yl)thio-butyramide
40. N-(2-Hydroxyethyl)-N-phenyl-4-(1-methyl-1,2,3,4-tetrazol-5-yl)thio-butyramide
41. N-(4-Sulfamoylphenyl)-4-(1-methyl-1,2,3,4-tetrazol-5-yl)thio-butyramide
42. N-(2-Methyl-3-chlorophenyl)-4-(1-methyl-1,2,3,4-tetrazol-5-yl)thio-butyramide
43. N-(4-Nitrophenyl)-4-(1-methyl-1,2,3,4-tetrazol-5-yl)thio-butyramide
44. N,N,-Diethyl-3-(1-ethyl-1,2,3,4-tetrazol-5-yl)methylthio-propionamide
45. N-(4-Methoxycyclohexyl)-4-(1-methyl-1,2,3,4-tetrazol-5-yl)thio-butyramide
46. N-Ethyl-N-cyclohexyl-4-(1-phenyl-1,2,3,4-tetrazol-5-yl)butyramide
47. N-(n-Butyl)-5-(1-phenyl-1,2,3,4-tetrazol-5-yl)valeramide
48. N-(n-Hexyl)-5-(1-phenyl-1,2,3,4-tetrazol-5-yl)valeramide
49. N-(4-Methoxyphenyl)-5-(1-phenyl-1,2,3,4-tetrazol-5-yl)valeramide
50. N-Isopropyl-N-cyclohexyl-5-(1-phenyl-1,2,3,4-tetrazol-5-yl)valeramide
51. N-Ethyl-N-cyclohexyl-5-(1-methyl-1,2,3,4-tetrazol-5-yl)valeramide
52. N,N-Diethyl-5-(1,2,3,4-tetrazol-5-yl)valeramide
53. 3-[1-(4-Ethylphenyl)-1,2,3,4-tetrazol-5-yl]methylthio-propionic acid
54. Methyl 5-(1-cyclohexyl-1,2,3,4-tetrazol-5-yl)valerate
55. N-Cyclohexyl-N-butyl-5-(1-methyl-1,2,3,4-tetrazol-5-yl)thio-butyramide
56. N-Ethyl-N-cyclooctyl-5-(1-methyl-1,2,3,4-tetrazol-5-yl)thio-butyramide
57. N-[4-(N,N-Dimethylamino)phenyl]-5-(1-methyl-1,2,3,4-tetrazol-5-yl)thio-butyramide
58. N,N-Dicyclohexyl-5-(1-methyl-1,2,3,4-tetrazol-5-yl)thio-butyramide Pharmacological Test 1

The pharmacological activities of the compouns (I) were tested by a Shay rat pylorus ligation method (cf. H. Shay et al: Gastroenterol., Vol. 5, page 43, 1945) which is the most popular method for testing of gastric juice secretion-inhibiting activity. The test was carried out by using male Wistar rats, weighing about 170 g and fasting for 24 hours.

Test compounds were administered 30 minutes before the pylorus ligation in a dose of 100 mg/kg in subcutaneous route, and the volume, total acidity and/or pepsin activity of the gastric juice were measured 4 hours after the ligation. As a control, a saline solution was administered instead of the test compound. The inhibitory ratio (%) of the test compounds was calculated when the inhibitory activities of the control were counted as zero (0). The results are shown in Table 1.

In the table, the inhibitory ratio (%) was evaluated as follows:
—: less than 10%
+: 10 to less than 50%
++: more than 50%

TABLE 1

| Test compound No. | Inhibitory ratio | | |
|---|---|---|---|
| | Volume of gastric juice | Total acidity | Pepsin activity |
| 1 | ++ | ++ | ++ |
| 2 | ++ | ++ | ++ |
| 3 | ++ | + | + |
| 4 | + | + | + |
| 5 | + | + | + |
| 6 | + | + | + |
| 7 | ++ | + | + |
| 8 | + | + | + |
| 9 | ++ | + | ++ |
| 10 | + | + | + |
| 11 | + | + | + |
| 12 | + | + | + |
| 13 | + | + | + |
| 20 | ++ | + | — |
| 21 | ++ | + | — |
| 22 | + | + | — |
| 23 | + | + | — |
| 24 | ++ | + | — |
| 25 | + | + | + |
| 26 | ++ | + | — |
| 27 | + | + | + |
| 28 | ++ | ++ | + |
| 29 | ++ | ++ | + |
| 30 | ++ | + | + |
| 31 | ++ | + | + |
| 32 | + | + | + |
| 33 | + | + | + |
| 34 | + | + | + |
| 35 | + | + | + |
| 36 | ++ | | |
| 37 | + | | |
| 38 | + | | |
| 39 | ++ | | |
| 40 | + | | |
| 41 | + | | |
| 42 | + | | |
| 43 | + | | |
| 44 | + | | |
| 45 | + | | |
| 46 | + | + | — |
| 51 | + | | |
| 52 | + | | |
| 53 | + | | |
| 54 | + | | |

Pharmacological Test 2: Stress ulcer

After male Wistar rats weighing about 170 g was fasted for 24 hours, the rats were restrained in a stress cage and dipped in water bath at 23° C. till chest of the animals. After 7 hours, the rats were killed and the stomach was isolated. Into the isolated stomach 10% formalin (8 ml) was poured and settled. The stomach was cut open at the greater curvature, and the length of each ulcer on the membrane was measured. Sum of the length of all ulcers was shown as ulcer index (UI). The test compound was orally administered to the rats before restraint in a stress cage in the form of 0.5% CMC suspension in a concentration of $1\times10^{-3}$ mole. As a control, only the solvent (CMC) was administered likewise.

The inhibitory ratio (%) of stress ulcer of the test compounds was calculated by the following equation:

$$\text{Inhibitory ratio} = \frac{(UI \text{ of rats of control}) - (UI \text{ of rats administered test compound})}{UI \text{ of rats of control}} \times 100$$

The results are shown in Table 2. In the table, the inhibitory ratio (%) was evaluated as follows:
+: 30 to less than 60%
++: more than 60%.

TABLE 2

| Test comp. No. | Inhibitory ratio | Test comp. No. | Inhibitory ratio | Test comp. No. | Inhibitory ratio |
|---|---|---|---|---|---|
| 1 | ++ | 17 | + | 48 | + |
| 4 | ++ | 18 | + | 49 | + |
| 7 | ++ | 23 | + | 50 | ++ |
| 8 | ++ | 34 | + | 51 | + |
| 14 | ++ | 35 | + | 52 | + |
| 15 | ++ | 46 | ++ | 44 | ++ |
| 16 | + | 47 | + | | |

Pharmacological Test 3: Acetic acid-induced ulcer

Male Wistar rats were used. Under anestherization, the abdomen of rats were opened to expose stomach, and then 30% aqueous acetic acid (0.015 ml) was injected below serous membrane which was loacated at boundary area of true gastric gland and pyloric glands and thereafter the abdomen was closed, by which an experimental ulcer was induced.

The test compound was orally administered in the dose as shown in Table 3 in the form of 0.5% CMC suspension or solution twice a day for 12 days after the acetic acid-induced ulcer was produced. As a control, only the solvent (CMC solution) was administered likewise.

After the reproduced mucous membrane was removed around the ulcers, the open area of ulcers was measured with a micrometer, and the sum of ulcer area was shown as ulcer index (UI). The inhibitory ratio (%) of acetic acid-induced ulcer of the test compounds was calculated in the same manner as in Pharmacological Test 2.

The results are shown in Table 3. In the table, the inhibitory ratio (%) was evaluated as follows:
+: 30 to less than 60%
++: more than 60%

TABLE 3

| Test compound No. | Dose | Inhibitory ratio |
|---|---|---|
| 19 | $3 \times 10^{-5}$ mole/kg · day | + |
| 2 | 20 mg/kg · day | + |
| 9 | " | + |
| 26 | " | + |
| 28 | " | + |
| 37 | " | + |
| 55 | " | + |
| 56 | " | + |
| 57 | " | + |
| 58 | " | + |

Pharmacological Test 4: Indomethacin-induced ulcer

After male Wistar rats weighing about 160 g was fasted for 24 hours, indomethacin was subcutaneously administered to the rats in a dose of 20 mg/kg in the form of a suspension in a mixture of 0.5% CMC and a small amount of Tween 80 (i.e. polyoxyethylene sorbitan monooleate). After 5 hours, the rats were killed and the stomach was isolated. Into the isolated stomach 10% formalin (8 ml) was poured and settled. The stomach was cut open at the greater curvature, and the length of each ulcer on the membrane was measured, based on which results the inhibitory ratio of the indomethacin-induced ulcer of the test compounds was calculated in the same manner as in Pharmacological Test 2. The test compound was orally administered to the rats in a concentration of $3 \times 10^{-4}$ mole in the form of 0.5% CMC suspension 30 minutes before the administration of indomethacin.

The results are shown in Table 4. In the table, the inhibitory ratio (%) was evaluated as follows:

+: 30 to less than 60%
++: more than 60%.

TABLE 4

| Test compound No. | Inhibitory ratio | Test compound No. | Inhibitory ratio |
|---|---|---|---|
| 39 | + | 47 | + |
| 45 | ++ | 49 | + |
| 46 | ++ | | |

Acute toxicity

The test compounds were orally administered to male Wistar rats, and the half lethal dose ($LD_{50}$) was measured. The results are shown in Table 5.

TABLE 5

| Test compound No. | $LD_{50}$(mg/kg, p.o.) |
|---|---|
| 1 | >500 |
| 2 | >500 |
| 3 | >500 |
| 4 | >500 |
| 5 | >500 |
| 6 | >500 |
| 7 | >500 |
| 8 | >500 |
| 9 | >500 |
| 10 | >500 |
| 11 | >500 |
| 12 | >500 |
| 13 | >500 |
| 16 | >500 |
| 17 | >500 |
| 19 | >500 |

What is claimed is:

1. A tetrazole derivative of the formula:

$$\begin{array}{c} N\text{------}N \\ \| \quad \| \\ N\diagdown_{N}\diagup (A)_l\text{---}B\text{---}COR^2 \\ | \\ R^1 \end{array}$$

wherein $R^1$ is hydrogen, an alkyl having from 1 to 6 carbon atoms, a cycloalkyl having from 3 to 12 carbon atoms or phenyl; A is sulfur or an alkylene-thio having from 1 to 6 carbon atoms; l is 1, B is an alkylene having from 1 to 6 carbon atoms; $R^2$ is hydroxy, an alkoxy having from 1 to 6 carbon atoms, or a group:

$$-N\diagup^{R^3}_{\diagdown R^4}$$

wherein $R^3$ and $R^4$ are the same or different and are each hydrogen, an alkyl having from 1 to 6 carbon atoms, a cycloalkyl having from 3 to 12 carbon atoms, phenyl, a cycloalkyl-alkyl having from 1 to 6 carbon atoms in the alkyl moiety and from 3 to 8 carbon atoms in the cycloalkyl moiety, a phenylalkyl having from 1 to 6 carbon atoms in the alkyl moiety, a hydroxy alkyl having from 1 to 6 carbon atoms, said cycloalkyl, phenyl and phenyl alkyl may have on the cycloalkyl or phenyl ring one or two substituents selected from the group consisting of an alkoxy having from 1 to 6 carbon atoms, an alkyl having from 1 to 6 carbon atoms, a halogen, an N,N-dialkylamino having from 1 to 6 carbon atoms in each alkyl moiety, nitro, aminosulfonyl, hydroxy and an alkanoyloxy having from 1 to 6 carbon atoms; or a pharmaceutically-acceptable salt thereof.

2. A compound according to claim 1, wherein $R^2$ is hydroxy or an alkoxy having from 1 to 6 carbon atoms.

3. A compound according to claim 1, wherein $R^2$ is a group:

$$-N\diagup^{R^3}_{\diagdown R^4}$$

wherein $R^3$ and $R^4$ are as defined above.

4. A compound according to claim 3, wherein A is an alkylenethio having 1 to 6 carbon atoms.

5. A compound according to claim 3, wherein A is sulfur.

6. A compound according to claim 4 or 5, wherein $R^3$ and $R^4$ are each hydrogen.

7. A compound according to claim 4 or 5, wherein one of $R^3$ and $R^4$ is hydrogen and another one of them is a member selected from the group consisting of an alkyl having 1 to 6 carbon atoms, a hydroxyalkyl having 1 to 6 carbon atoms, a cycloalkyl-alkyl having 1 to 6 carbon atoms in the alkyl moiety and 3 to 8 carbon atoms in the cycloalkyl moiety and a substituted or unsubstituted cycloalkyl having 3 to 12 carbon atoms.

8. A compound according to claim 4 or 5, wherein one of $R^3$ and $R^4$ is hydrogen and another one of them is a member selected from the group consisting of a substituted or unsubstituted phenyl and a substituted or unsubstituted phenylalkyl having 1 to 6 carbon atoms in the alkyl moiety.

9. A compound according to claim 4 or 5, wherein one of $R^3$ or $R^4$ is an alkyl having 1 to 6 carbon atoms and another one of them is a member selected from the group consisting of an alkyl having 1 to 6 carbon atoms and a hydroxyalkyl having 1 to 6 carbon atoms.

10. A compound according to claim 4 or 5, wherein one of $R^3$ and $R^4$ is an alkyl having 1 to 6 carbon atoms and another one of them is a member selected from the group consisting of a substituted or unsubstituted cycloalkyl having 3 to 12 carbon atoms and a cycloalkylalkyl having 1 to 6 carbon atoms in the alkyl moiety and 3 to 8 carbon atoms in the cycloalkyl moiety.

11. A compound according to claim 4 or 5, wherein one of $R^3$ and $R^4$ is an alkyl having 1 to 6 carbon atoms and another one of them is a member selected from the group consisting of a substituted or unsubstituted phenyl and a substituted or unsubstituted phenyl alkyl having 1 to 6 carbon atoms in the alkyl moiety.

12. A compound according to claim 4 or 5, wherein one of $R^3$ and $R^4$ is a substituted or unsubstituted cycloalkyl having 3 to 12 carbon atoms and another one of them is a member selected from the group consisting of a substituted or unsubstituted cycloalkyl having 3 to 12 carbon atoms and a cycloalkyl-alkyl having 1 to 6 carbon atoms in the alkyl moiety and 3 to 8 carbon atoms in the cycloalkyl moiety.

13. A compound according to claim 4 or 5, one of $R^3$ and $R^4$ is a substituted or unsubstituted cycloalkyl having 3 to 12 carbon atoms and another one of them is a member selected from the group consisting a hydroxyalkyl having 1 to 6 carbon atoms, a substituted or unsubstituted phenyl and a substituted or unsubstituted phenylalkyl having 1 to 6 carbon atoms in the alkyl moiety.

14. A compound according to claim 4 or 5, wherein one of $R^3$ and $R^4$ is a substituted or unsubstituted phenyl and another one of them is a member selected from the group consisting of a substituted or unsubstituted phenyl, a substituted or unsubstituted phenylalkyl having 1 to 6 carbon atoms in the alkyl moiety, a cycloalkyl-alkyl having 1 to 6 carbon atoms in the alkyl moiety and 3 to 8 carbon atoms in the cycloalkyl moiety and a hydroxyalkyl having 1 to 6 carbon atoms.

15. A compound according to claim 4 or 5, wherein one of $R^3$ and $R^4$ is a substituted or unsubstituted phenylalkyl having 1 to 6 carbon atoms in the alkyl moiety and another one of them is a member selected from the group consisting of a substituted or unsubstituted phenylalkyl having 1 to 6 carbon atoms in the alkyl moiety, a cycloalkyl-alkyl having 1 to 6 carbon atoms in the alkyl moiety and 3 to 8 carbon atoms in the cycloalkyl moiety and a hydroxyalkyl having 1 to 6 carbon atoms.

16. A compound according to claim 4 or 5, wherein one of $R^3$ and $R^4$ is a cycloalkyl-alkyl having 1 to 6 carbon atoms in the alkyl moiety and 3 to 8 carbon atoms in the cycloalkyl moiety and another one of them is a member selected from the group consisting of a cycloalkyl-alkyl having 1 to 6 carbon atoms in the alkyl moiety and 3 to 8 carbon atoms in the cycloalkyl moiety and a hydroxy alkyl having 1 to 6 carbon atoms.

17. A compound according to claim 1, wherein the compound is N,N-dimethyl-4-(1-methyl-1,2,3,4-tetrazol-5-yl)thio-butyramide.

18. A compound according to claim 1, wherein the compound is N,N-diethyl-4-(1-methyl-1,2,3,4-tetrazol-5-yl)thio-butyramide.

19. A compound according to claim 1, wherein the compound is N-ethyl-N-(2-hydroxycyclohexyl)-4-(1-methyl-1,2,3,4-tetrazol-5-yl)thio-butyramide.

20. A compound according to claim 1, wherein the compound is N-ethyl-N-(4-hydroxycyclohexyl)-4-(1-methyl-1,2,3,4-tetrazol-5-yl)thio-butyramide.

21. A compound according to claim 1, wherein the compound is N-ethyl-N-cyclohexyl-3-(1-methyl-1,2,3,4-tetrazol-5-yl)thio-propionamide.

22. A compound according to claim 1, wherein the compound is N-ethyl-N-cyclohexyl-5-(1-methyl-1,2,3,4-tetrazol-5-yl)thio-valeramide.

23. A compound according to claim 1, wherein the compound is N,N-diethyl-4-(1-phenyl-1,2,3,4-tetrazol-5-yl)-thio-butyramide.

24. A compound according to claim 1, wherein the compound is N-ethyl-N-cyclohexyl-4-(1-phenyl-1,2,3,4-tetrazol-5-yl)thio-butyramide.

25. A compound according to claim 1, wherein the compound is N-ethyl-N-cyclohexyl-4-(1-cyclohexyl-1,2,3,4-tetrazol-5-yl)thio-butyramide.

26. A compound according to claim 1, wherein the compound is 3-(1-ethyl-1,2,3,4-tetrazol-5-yl)methylthio-propionamide.

27. A compound according to claim 1, wherein the compound is 3-(1-phenyl-1,2,3,4-tetrazol-5-yl)methyl-thiopropionamide.

28. A compound according to claim 1, wherein the compound is N-[2-(3,4-dimethoxyphenyl)ethyl]-4-(1-methyl-1,2,3,4-tetrazol-5-yl)thio-butyramide.

29. A compound according to claim 1, wherein the compound is methyl 4-(1-methyl-1,2,3,4-tetrazol-5-yl)thiobutyrate.

30. An anti-ulcer composition diluent or carrier and, which comprises as an essential active ingredient, a therapeutically effective amount of a compound of claim 17.

31. A method for the treatment of peptic and duodenal ulcers by administering an anti-ulcer composition which comprises a compound of claim 1 or a pharmaceutically acceptable salt thereof in admixture with a pharmaceutically acceptable diluent or carrier.

32. A method according to claim 31, wherein $R^2$ is hydroxy or an alkoxy having 1 to 6 carbon atoms.

33. A method according to claim 31, wherein $R^2$ is a group:

wherein $R^3$ and $R^4$ are as defined above.

34. A method according to claim 33, wherein A is an alkylenethio having 1 to 6 carbon atoms.

35. A method according to claim 34, wherein $R^3$ and $R^4$ are the same or different and are each hydrogen, an alkyl having 1 to 6 carbon atoms, or a substituted or unsubstituted cycloalkyl having 3 to 12 carbon atoms.

36. A method according to claim 33, wherein A is sulfur.

37. A method according to claim 36, wherein $R^3$ and $R^4$ are the same or different and are each hydrogen, an alkyl having 1 to 6 carbon atoms or a substituted or unsubstituted cycloalkyl having 3 to 12 carbon atoms.

38. A tetrazole derivative according to claim 1 wherein $R^3$ and $R^4$ are the same or different and are each hydrogen; an alkyl having from 1 to 6 carbon atoms; a cycloalkyl having from 3 to 12 carbon atoms which is unsubstituted or substituted by one or two substituents selected from the group consisting of hydroxy, an alkanoyloxy having from 1 to 6 carbon atoms and an alkoxy having from 1 to 6 carbon atoms; a phenyl unsubstituted or substituted by one or two substituents selected from the group consisting of an alkoxy having from 1 to 6 carbon atoms, an alkyl having from 1 to 6 carbon atoms, a halogen, an N,N-dialkylamino having from 1 to 6 carbon atoms in each alkyl moiety, nitro and aminosulfonyl; a cycloalkyl-alkyl having from 1 to 6 carbon atoms in the alkyl moiety and from 3 to 8 carbon atoms in the cycloalkyl moiety; a phenylalkyl having from 1 to 6 carbon atoms in the alkyl moiety which is unsubstituted or substituted by one or two alkoxys having from 1 to 6 carbon atoms; and a hydroxyalkyl having from 1 to 6 carbon atoms; or a pharmaceutically-acceptable salt thereof.

39. A tetrazole derivative of the formula:

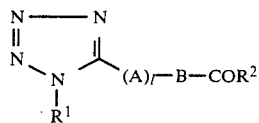

wherein $R^1$ is hydrogen, an alkyl having 1 to 6 carbon atoms, a cycloalkyl having 3 to 12 carbon atoms or phenyl; l is 0; B is an alkylene having 1 to 6 carbon atoms; $R^2$ is hydroxy, an alkoxy having 1 to 6 carbon atoms, or a group:

wherein $R^3$ and $R^4$ are the same or different and are each hydrogen, an alkyl having 1 to 6 carbon atoms, a cycloalkyl having 3 to 12 carbon atoms, phenyl, a cycloalkyl-alkyl having 1 to 6 carbon atoms in the alkyl moiety and 3 to 8 carbon atoms in the cycloalkyl moiety, a phenylalkyl having 1 to 6 carbon atoms in the alkyl moiety, a hydroxyalkyl having 1 to 6 carbon atoms in the alkyl moiety; said cycloalkyl, phenyl and phenyl alkyl optionally have on the cycloalkyl or phenyl ring one or two substituents selected from the group consisting of an alkoxy having 1 to 6 carbon atoms, an alkyl having 1 to 6 carbon atoms, a halogen, an N,N-dialkylamino having 1 to 6 carbon atoms in each alkyl moiety, nitro, aminosulfonyl, hydroxy and an alkanoyloxy having 1 to 6 carbon atoms; provided that, (a) when l is 0, B is —CRR'—(CH$_2$)$_p$— (wherein R and R' are each hydrogen, methyl or ethyl, and p is 0 or 1) and $R^1$ is methyl, ethyl, n-butyl, cyclohexyl or an unsubstituted phenyl, $R^2$ is other than hydroxy, or ethoxy, and (b) when l is 0, B is —CR"R'"—(CH$_2$)$_q$— (wherein R" and R'" are each hydrogen or methyl, and q is 0 or 1) and $R^1$ is cyclohexyl, n-butyl or an unsubstituted phenyl, $R^2$ is other than —NR$^{3'}$R$^{4'}$ (wherein one of R$^{3'}$ and R$^{4'}$ is hydrogen, methyl, ethyl or benzyl, and another one of them is hydrogen or ethyl);
or a pharmaceutically-acceptable salt thereof.

40. A compound according to claim 39 wherein the group $R^2$ is a group:

wherein $R^3$ is hydrogen, an alkyl having 1 to 6 carbon atoms, a substituted or unsubstituted cycloalkyl having 3 to 12 carbon atoms, a substituted or unsubstituted phenyl, a cycloalkyl-alkyl having 1 to 6 carbon atoms in the alkyl moiety and 3 to 8 carbon atoms in the cycloalkyl moiety, a substituted or unsubstituted phenylalkyl having 1 to 6 carbon atoms in the alkyl moiety or a hydroxyalkyl having 1 to 6 carbon atoms in the alkyl moiety; $R^4$ is a substituted or unsubstituted cycloalkyl having 3 to 12 carbon atoms, a substituted or unsubstituted phenyl, a cycloalkyl-alkyl having 1 to 6 carbon atoms in the alkyl moiety and 3 to 8 carbon atoms in the cycloalkyl moiety, a substituted phenylalkyl having 1 to 6 carbon atoms in the alkyl moiety or a hydroxyalkyl having 1 to 6 carbon atoms; said substituted cycloalkyl, phenyl and phenylalkyl have on the cycloalkyl or phenyl ring one or two substituents selected from the group consisting of an alkoxy having 1 to 6 carbon atoms, an alkyl having 1 to 6 carbon atoms, a halogen, an N,N-dialkylamino having 1 to 6 carbon atoms in each alkyl moiety, nitro, aminosulfonyl, hydroxy and an alkanoyloxy having 1 to 16 carbon atoms;
or a pharmaceutically-acceptable salt thereof.

41. A compound according to claim 40, wherein $R^3$ is hydrogen, an alkyl having 1 to 6 carbon atoms or a cycloalkyl having 3 to 12 carbon atoms; and $R^4$ is a cycloalkyl having 3 to 12 carbon atoms; said cycloalkyl having one or two substituents selected from the group consisting of an alkoxy having 1 to 6 carbon atoms, an alkyl having 1 to 6 carbon atoms, a halogen, an N,N-dialkylamino having 1 to 6 carbon atoms in each alkyl moiety, nitro, aminosulfonyl, hydroxy and an alkanoyloxy having 1 to 6 carbon atoms.

42. A compound according to claim 40, wherein $R^3$ is hydrogen or an alkyl having 1 to 6 carbon atoms and $R^4$ is a member selected from the group consisting of hydroxyalkyl having 1 to 16 carbon atoms and a cycloalkyl-alkyl having 1 to 6 carbon atoms in the alkyl moiety and 3 to 8 carbon atoms in the cycloalkyl moiety.

43. A compound according to claim 40, wherein $R^3$ is hydrogen or an alkyl having 1 to 6 carbon atoms and $R^4$ is a member selected from the group consisting of a substituted or unsubstituted phenyl and a substituted phenylalkyl having 1 to 6 carbon atoms in the alkyl moiety, said substituted phenyl or phenylalkyl having one or two ring substituents selected from the group consisting of an alkoxy having 1 to 6 carbon atoms, an alkyl having 1 to 6 carbon atoms, a halogen, an N,N-dialkylamino having 1 to 6 carbon atoms in each alkyl moiety, nitro, aminosulfonyl, hydroxy and an alkanoyloxy having 1 to 6 carbon atoms.

44. A compound according to claim 40 wherein $R^3$ is a substituted or unsubstituted cycloalkyl having 3 to 12 carbon atoms in the cycloalkyl moiety and $R^4$ is a member selected from the group consisting of a hydroxyalkyl having from 1 to 6 carbon atoms, a substituted or unsubstituted phenyl and a substituted phenylalkyl having 1 to 6 carbon atoms in the alkyl moiety; said substituted cycloalkyl, phenyl or phenylalkyl having one or two ring substituents selected from the group consisting of an alkoxy having 1 to 6 carbon atoms, an alkyl having 1 to 16 carbon atoms, a halogen, an N,N-dialkylamino having 1 to 6 carbon atoms in each alkyl moiety, nitro, aminosulfonyl, hydroxy and an alkonoyloxy having from 1 to 6 carbon atoms.

45. A compound according to claim 39, wherein the compound is N-methyl-N-cyclohexyl-5-(1-phenyl-1,2,3,4-tetrazol-5-yl)valeramide.

46. A compound according to claim 39, wherein the compound is N-isopropyl-N-cyclohexyl-5-(1-phenyl-1,2,3,4-tetrazol-5-yl)valeramide.

47. A compound according to claim 39, wherein the compound is N-ethyl-N-cyclohexyl-5-(1-phenyl-1,2,3,4-tetrazol-5-yl)butyramide.

48. A compound according to claim 39, wherein the compound is N,N-diethyl-5-(1-phenyl-1,2,3,4-tetrazol-5-yl)-valeramide.

49. A compound according to claim 39, wherein the compound is N-ethyl-N-cyclohexyl-5-(1-phenyl-1,2,3,4-tetrazol-5-yl)valeramide.

50. A compound according to claim 39, wherein the compound is N-ethyl-N-cyclohexyl-5-(1-cyclohexyl-1,2,3,4-tetrazol-5-yl)valeramide.

51. An anti-ulcer composition which comprises, as an essential active ingredient, a therapeutically-effective amount of a tetrazole derivative of the formula:

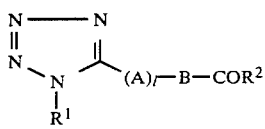

wherein $R^1$ is hydrogen, an alkyl having 1 to 6 carbon atoms, a cycloalkyl having 3 to 12 carbon atoms or phenyl; l is 0; B is an alkylene having 1 to 6 carbon atoms; $R^2$ is hydroxy, an alkoxy having 1 to 6 carbon atoms, or a group:

wherein $R^3$ and $R^4$ are the same or different and are each hydrogen, an alkyl having 1 to 6 carbon atoms, a cycloalkyl having 3 to 12 carbon atoms, phenyl, a cycloalkyl-alkyl having 1 to 6 carbon atoms in the alkyl moiety and 3 to 8 carbon atoms in the cycloalkyl moiety, a phenylalkyl having 1 to 6 carbon atoms in the alkyl moiety or a hydroxyalkyl having 1 to 6 carbon atoms in the alkyl moiety; said cycloalkyl, phenyl and phenyl alkyl optionally have on the cycloalkyl or phenyl ring one or two substituents selected from the group consisting of an alkoxy having 1 to 6 carbon atoms, an alkyl having 1 to 6 carbon atoms, a halogen, an N,N-dialkylamino having 1 to 6 carbon atoms in each alkyl moiety, nitro, aminosulfonyl, hydroxy and an alkanoyloxy having 1 to 6 carbon atoms; provided that, (a) when l is 0, B is —CRR'—(CH$_2$)$_p$— (wherein R and R' are each hydrogen, methyl or ethyl, and p is 0 or 1) and $R^1$ is methyl, ethyl, n-butyl, cyclohexyl or an unsubstituted phenyl, $R^2$ is other than hydroxy or ethoxy and, (b) when l is 0, B is —CR''R'''—(CH$_2$)$_q$— (wherein R'' and R''' are each hydrogen or methyl, and q is 0 or 1) and $R^1$ is cyclohexyl, n-butyl or an unsubstituted phenyl, $R^2$ is other than —NR$^{3'}$R$^{4'}$ (wherein one of R$^{3'}$ and R$^{4'}$ is hydrogen, methyl, ethyl or benzyl, and another of them is hydrogen or ethyl), or a pharmaceutically-acceptable salt thereof; in admixture with a pharmaceutically-acceptable diluent or carrier.

52. A composition according to claim 51, wherein the group $R^2$ is a group:

wherein $R^3$ is hydrogen, an alkyl having 1 to 6 carbon atoms, a substituted or unsubstituted cycloalkyl having 3 to 12 carbon atoms, a substituted or unsubstituted phenyl, a cycloalkyl-alkyl having 1 to 6 carbon atoms in the alkyl moiety and 3 to 8 carbon atoms in the cycloalkyl moiety, a substituted or unsubstituted phenylalkyl having 1 to 6 carbon atoms in the alkyl moiety or a hydroxyalkyl having 1 to 6 carbon atoms in the alkyl moiety; $R^4$ is a substituted or unsubstituted cycloalkyl having 3 to 12 carbon atoms, a substituted or unsubstituted phenyl, a cycloalkyl-alkyl having 1 to 6 carbon atoms in the alkyl moiety and 3 to 8 carbon atoms in the cycloalkyl moiety, a substituted phenylalkyl having 1 to 6 carbon atoms in the alkyl moiety or a hydroxyalkyl having 1 to 6 carbon atoms; said substituted cycloalkyl, phenyl and phenylalkyl have on the cycloalkyl or phenyl ring one or two substituents selected from the group consisting of an alkyl having 1 to 6 carbon atoms, an alkoxy having 1 to 6 carbon atoms, a halogen, an N,N-dialkylamino having 1 to 6 carbon atoms in each alkyl moiety, nitro, aminosulfonyl, hydroxy and an alkanoyloxy having 1 to 16 carbon atoms, or a pharmaceutically-acceptable salt thereof.

* * * * *